United States Patent
Danitz et al.

(10) Patent No.: US 11,590,345 B2
(45) Date of Patent: Feb. 28, 2023

(54) TREATMENT OF TISSUE BY THE APPLICATION OF ENERGY

(71) Applicant: PULSE BIOSCIENCES, INC., Hayward, CA (US)

(72) Inventors: David J. Danitz, San Jose, CA (US); Cameron D. Hinman, Thurmond, NC (US); Edward Ebbers, San Carlos, CA (US); Richard L. Nuccitelli, Millbrae, CA (US); Kevin L. Moss, Tracy, CA (US); Darrin R. Uecker, San Mateo, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 484 days.

(21) Appl. No.: 16/765,661

(22) PCT Filed: Aug. 6, 2018

(86) PCT No.: PCT/US2018/045433
§ 371 (c)(1),
(2) Date: May 20, 2020

(87) PCT Pub. No.: WO2019/032474
PCT Pub. Date: Feb. 14, 2019

(65) Prior Publication Data
US 2020/0297998 A1    Sep. 24, 2020

Related U.S. Application Data

(63) Continuation-in-part of application No. 15/973,254, filed on May 7, 2018, now Pat. No. 10,850,095.
(Continued)

(51) Int. Cl.
*A61N 1/32* (2006.01)
*A61N 1/05* (2006.01)
(Continued)

(52) U.S. Cl.
CPC ............ *A61N 1/328* (2013.01); *A61N 1/025* (2013.01); *A61N 1/0502* (2013.01);
(Continued)

(58) Field of Classification Search
None
See application file for complete search history.

(56) References Cited

U.S. PATENT DOCUMENTS 5,688,253 A    11/1997 Paradis
5,702,359 A    12/1997 Hofmann et al.
(Continued)

FOREIGN PATENT DOCUMENTS

CA        2838411 A1      1/2005
WO    WO2013/143603 A1   10/2013
WO    WO2016/087289 A1    6/2016

OTHER PUBLICATIONS

European Supplemental Search Report dated Apr. 23, 2021 for European Patent Application No. 18843413.8-1113; 7 pages.
(Continued)

*Primary Examiner* — Paula J Stice
(74) *Attorney, Agent, or Firm* — Shay Glenn LLP

(57) ABSTRACT

Methods and apparatuses for treating a tissue with an electric treatment by rotating a pattern of electrodes partway through a treatment is disclosed. Also described herein are methods and apparatuses to treat tissue, including treating skin disorders, by selectively de-nucleating epidermal cells without provoking a significant inflammatory response, e.g., without increasing the density of leukocytes in the treated skin, and without affecting the non-cellular components of the dermis.

34 Claims, 24 Drawing Sheets

Related U.S. Application Data

(60) Provisional application No. 62/542,711, filed on Aug. 8, 2017.

(51) Int. Cl.
  *A61N 1/36* (2006.01)
  *A61N 1/02* (2006.01)
  *A61B 34/30* (2016.01)

(52) U.S. Cl.
  CPC ..... *A61N 1/36017* (2013.01); *A61N 1/36034* (2017.08); *A61B 34/30* (2016.02)

(56) References Cited

U.S. PATENT DOCUMENTS

| | | | |
|---|---|---|---|
| 5,718,246 A | 2/1998 | Vona | |
| 5,735,827 A | 4/1998 | Adwers et al. | |
| 5,769,827 A | 6/1998 | Demichele et al. | |
| 5,792,122 A | 8/1998 | Brimhall et al. | |
| 5,798,579 A | 8/1998 | McPhee | |
| 5,902,272 A | 5/1999 | Eggers et al. | |
| 6,009,347 A | 12/1999 | Hofmann | |
| 6,010,487 A | 1/2000 | Demichele et al. | |
| 6,017,354 A | 1/2000 | Culp et al. | |
| 6,181,964 B1 | 1/2001 | Hofmann et al. | |
| 6,190,381 B1 | 2/2001 | Olsen et al. | |
| 6,221,056 B1 | 4/2001 | Silverman | |
| 6,326,177 B1 | 12/2001 | Schoenbach et al. | |
| 6,508,786 B2 | 1/2003 | Huitema et al. | |
| 6,633,093 B1 | 10/2003 | Rim et al. | |
| 6,654,636 B1 | 11/2003 | Dev et al. | |
| 6,697,670 B2 | 2/2004 | Chomenky et al. | |
| 6,743,211 B1 | 6/2004 | Prausnitz et al. | |
| 6,831,377 B2 | 12/2004 | Yampolsky et al. | |
| 7,395,112 B2 | 7/2008 | Keisari et al. | |
| 7,767,433 B2 | 8/2010 | Kuthi et al. | |
| RE42,277 E | 4/2011 | Jaafar et al. | |
| 7,938,824 B2 | 5/2011 | Chomenky et al. | |
| 8,000,813 B2 | 8/2011 | Schoenbach et al. | |
| 8,512,334 B2 | 8/2013 | Nuccitelli et al. | |
| 8,814,833 B2 | 8/2014 | Farrell et al. | |
| 8,822,222 B2 | 9/2014 | Beebe et al. | |
| 8,979,912 B2 | 3/2015 | Na et al. | |
| 9,101,337 B2 | 8/2015 | Hoegerle et al. | |
| 9,101,764 B2 | 8/2015 | Nuccitelli et al. | |
| 9,414,881 B2 | 8/2016 | Callas et al. | |
| 9,656,055 B2 | 5/2017 | Weissberg et al. | |
| 9,724,155 B2 | 8/2017 | Nuccitelli et al. | |
| 9,895,520 B2 | 2/2018 | Burton et al. | |
| 9,931,161 B2 | 4/2018 | Willis | |
| 9,953,815 B2 | 4/2018 | Griebeler | |
| 9,956,391 B2 | 5/2018 | Weissberg et al. | |
| 9,960,763 B2 | 5/2018 | Miller et al. | |
| 10,020,800 B2 | 7/2018 | Prager et al. | |
| 10,022,695 B2 | 7/2018 | Zhang et al. | |
| 10,154,869 B2 | 12/2018 | Onik et al. | |
| 10,154,876 B2 | 12/2018 | Callas et al. | |
| 2003/0229316 A1 | 12/2003 | Hwang et al. | |
| 2003/0233087 A1 | 12/2003 | Chen et al. | |
| 2004/0181237 A1 | 9/2004 | Forde et al. | |
| 2004/0186466 A1 | 9/2004 | Chornenky et al. | |
| 2005/0119627 A1 | 6/2005 | Crawford | |
| 2005/0119649 A1 | 6/2005 | Swanson | |
| 2005/0171534 A1 | 8/2005 | Habib | |
| 2006/0015147 A1 | 1/2006 | Persson et al. | |
| 2006/0062074 A1 | 3/2006 | Gundersen et al. | |
| 2007/0060989 A1* | 3/2007 | Deem | A61B 18/1477 607/99 |
| 2008/0015516 A1 | 1/2008 | Lavi | |
| 2008/0200861 A1* | 8/2008 | Shalev | A61Q 9/04 604/20 |
| 2009/0012513 A1 | 1/2009 | Utley et al. | |
| 2009/0247944 A1 | 10/2009 | Kirschenman et al. | |
| 2009/0299417 A1 | 12/2009 | Schoenbach et al. | |
| 2010/0042095 A1 | 2/2010 | Bigley et al. | |
| 2010/0049194 A1 | 2/2010 | Hart et al. | |
| 2010/0240995 A1 | 9/2010 | Nuccitelli et al. | |
| 2011/0092973 A1 | 4/2011 | Nuccitelli et al. | |
| 2011/0112527 A1 | 5/2011 | Hamilton et al. | |
| 2012/0109263 A1 | 5/2012 | Kolb et al. | |
| 2012/0191085 A1* | 7/2012 | Eckhouse | A61B 17/50 606/133 |
| 2012/0277624 A1 | 11/2012 | Cucin | |
| 2013/0012937 A1 | 1/2013 | Mulier et al. | |
| 2013/0018441 A1 | 1/2013 | Childs | |
| 2013/0190836 A1 | 7/2013 | McCreery | |
| 2013/0289358 A1 | 10/2013 | Melsky et al. | |
| 2014/0005658 A1 | 1/2014 | Rosenbegr | |
| 2014/0052126 A1 | 2/2014 | Long et al. | |
| 2014/0155963 A1 | 6/2014 | Ko | |
| 2014/0364797 A1 | 12/2014 | Schoenbach et al. | |
| 2015/0201991 A1 | 7/2015 | Zemlin | |
| 2015/0230855 A1 | 8/2015 | Chornenky et al. | |
| 2015/0318846 A1 | 11/2015 | Prager et al. | |
| 2016/0192999 A1 | 7/2016 | Stulen et al. | |
| 2016/0271380 A1 | 9/2016 | Poon et al. | |
| 2016/0296269 A1 | 10/2016 | Rubinsky et al. | |
| 2016/0317216 A1* | 11/2016 | Hermes | A61B 34/30 |
| 2016/0338761 A1 | 11/2016 | Chornenky et al. | |
| 2016/0361109 A1 | 12/2016 | Weaver et al. | |
| 2016/0367310 A1 | 12/2016 | Onik et al. | |
| 2017/0072193 A1 | 3/2017 | Heller et al. | |
| 2017/0112577 A1* | 4/2017 | Bonutti | G06T 7/194 |
| 2017/0127987 A1 | 5/2017 | Hezi-Yamit et al. | |
| 2017/0209695 A1 | 7/2017 | Solomon | |
| 2017/0216353 A1 | 8/2017 | Nuccitelli et al. | |
| 2017/0245928 A1 | 8/2017 | Xiao et al. | |
| 2017/0281274 A1 | 10/2017 | Santana | |
| 2017/0326361 A1 | 11/2017 | Kreis et al. | |
| 2017/0348525 A1 | 12/2017 | Sano et al. | |
| 2018/0078755 A1 | 3/2018 | Kreis et al. | |
| 2018/0154141 A1 | 6/2018 | Ahn | |
| 2018/0177543 A1 | 6/2018 | You et al. | |
| 2019/0009084 A1 | 1/2019 | Stadelmann et al. | |
| 2019/0046791 A1 | 2/2019 | Ebbers et al. | |
| 2019/0109591 A1 | 4/2019 | Miller et al. | |
| 2019/0217080 A1 | 7/2019 | Moss et al. | |
| 2021/0085967 A1 | 3/2021 | Ebbers et al. | |

OTHER PUBLICATIONS

Yin et al.; Nanosecond pulsed electric field (nsPEF) treatment for hepatocellular carcinoma: A novel locoregional ablation decreasing lung metastasis; Cancer Letters; 346 (2014); pp. 285-291; Jan. 15, 2014.

International Search Report and Written Opinion dated Dec. 11, 2018 for PCT/US2018/045433; 16 pages.

Canadian Office Action dated Apr. 7, 2021 for Canadian Patent Application No. 3,072,499; 3 pages.

\* cited by examiner

Untreated Control
Epidermal cells
with dark nuclei

601

1 Day post

SIN#2, TL4, 1 Day Post
"Ghost cells" missing nuclei
Non-viable epidermis
Minimal inflammation

603

7 Days Later

SIN#2, TL4, 5 Day Post
(Actual =7 days)
Original necrotic
epidermis peeling
New epidermis layer,
healthy nuclei
Minimal inflammation

607

605 Necrotic crust

609 New Epidermis

SIN 005, TL6, 15 days post
Some change in elastin near surface

SIN 005, TL6, 60 days post
Restoration of normal elastic orientation and density

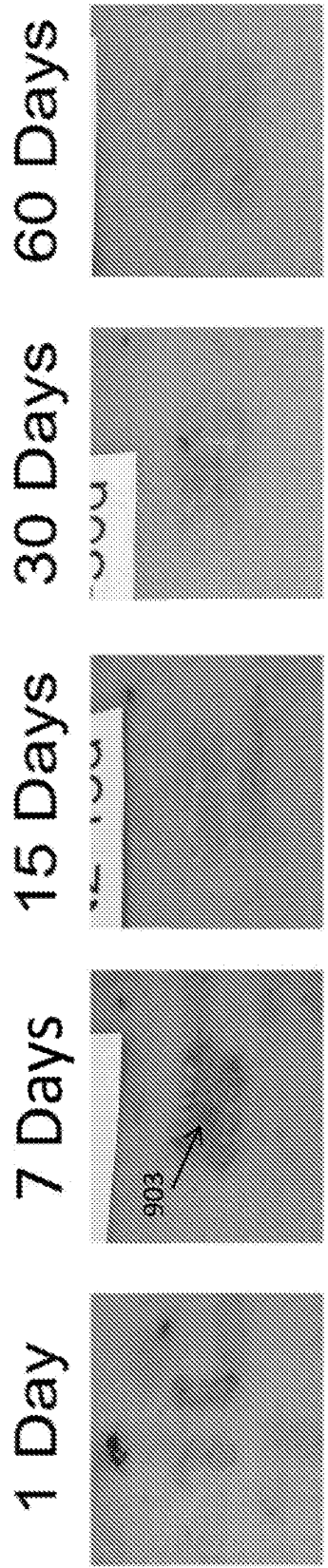

<u>1 day post</u>
All cells in treated epidermis are "ghost" cells

<u>7 days post</u>
original epidermal layer is peeling away, with emerging new epidermis below

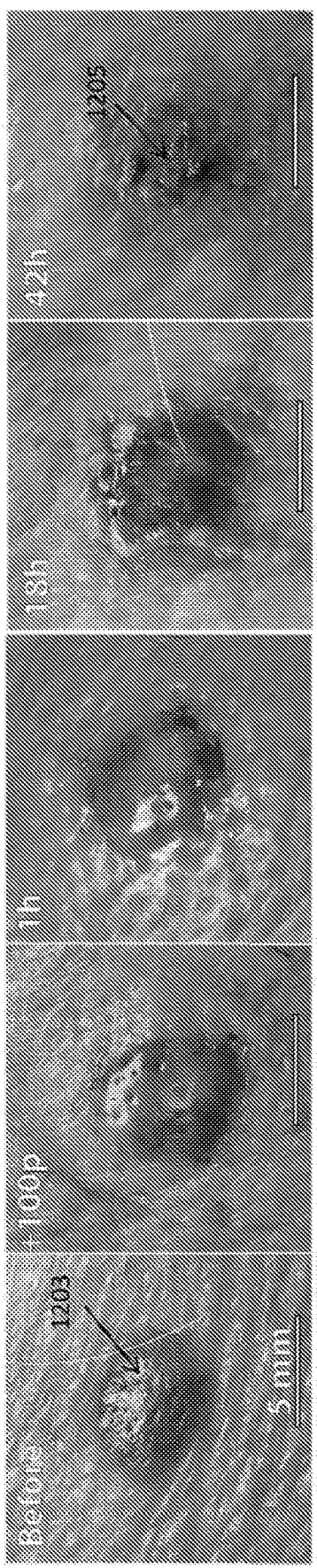
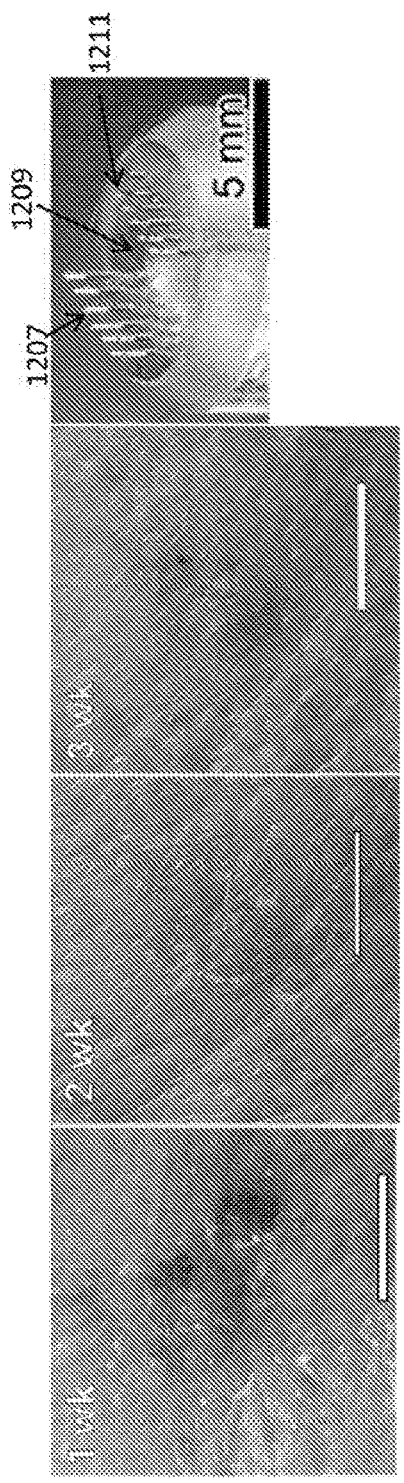
Seborrheic Keratosis: 100 pulses, 100 ns, 30 kV/cm (50 seconds)
FIG. 12A FIG. 12B FIG. 12C FIG. 12D FIG. 12E
FIG. 12F FIG. 12G FIG. 12H FIG. 12I Common Skin Lesion Pre-Treatment Cryosurgery
90 days
Post-Treatment PulseTx
15 days Post-Treatment[1]

PulseTx
60 days Post-Treatment[1]

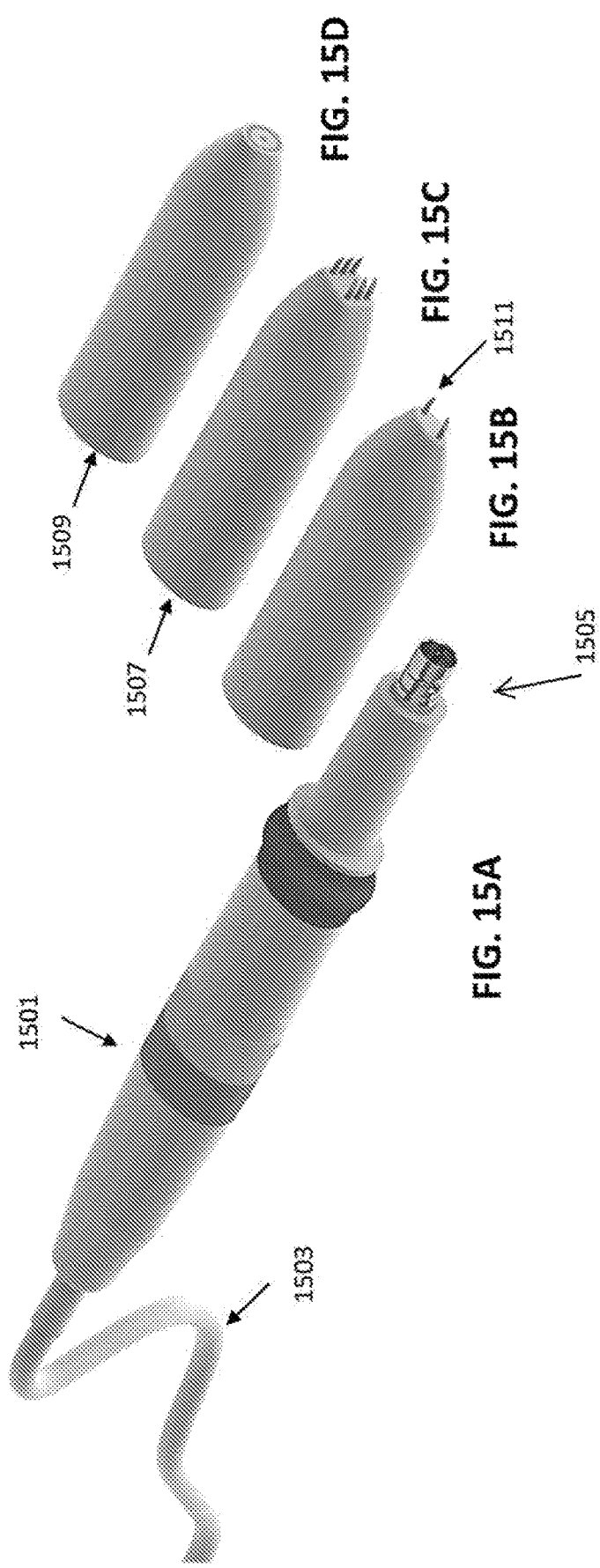

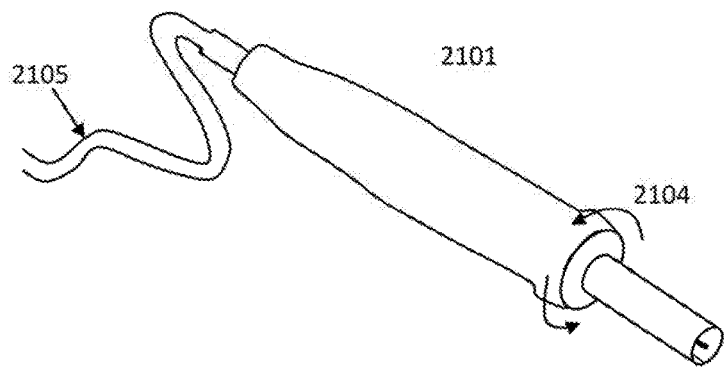
FIG. 21A
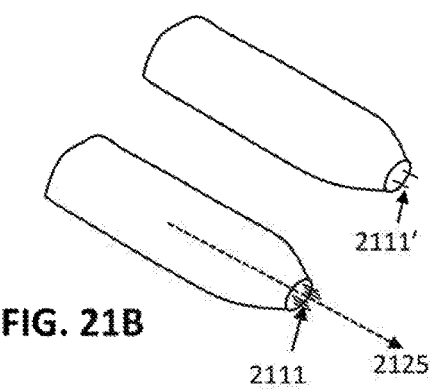
FIG. 21C
FIG. 21B
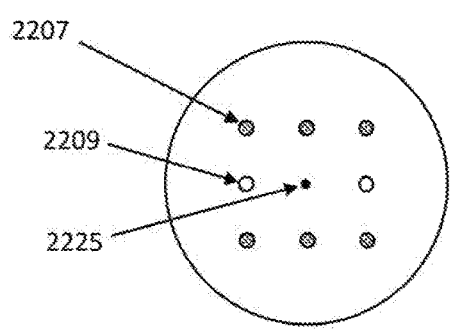
FIG. 22A
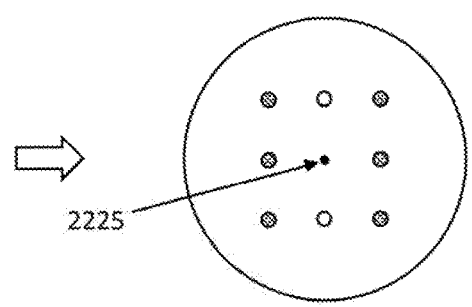
FIG. 22B
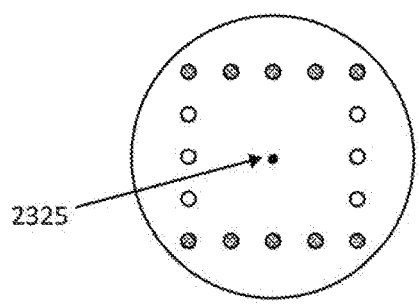
FIG. 23A
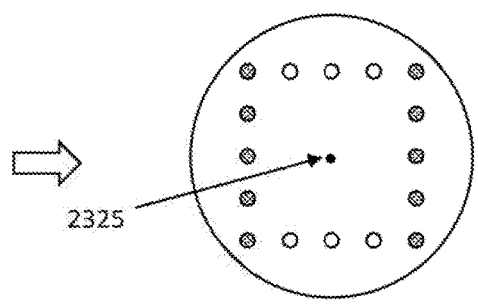
FIG. 23B

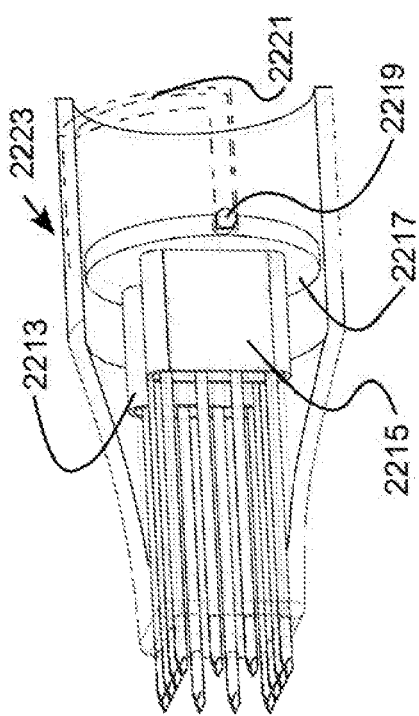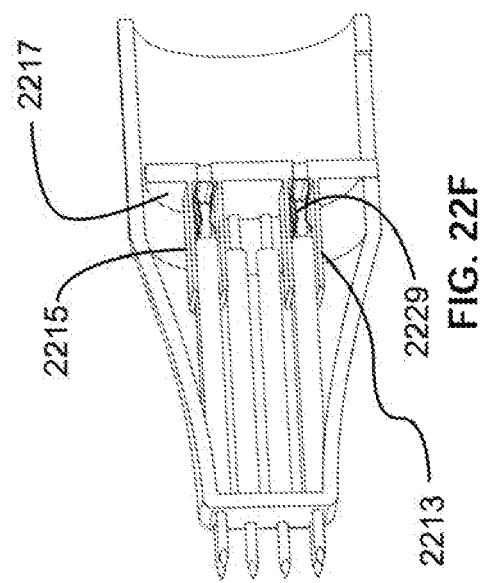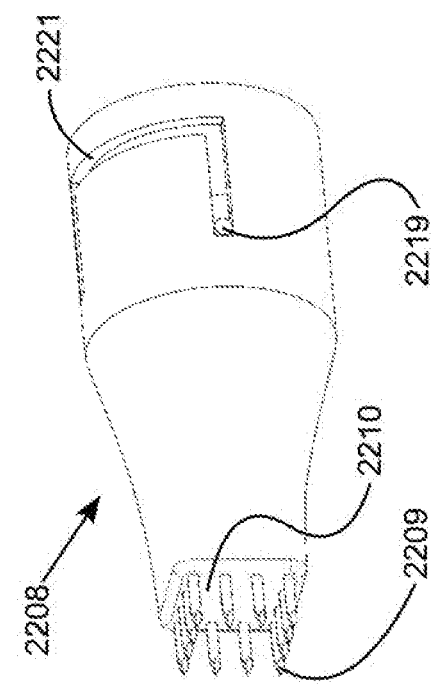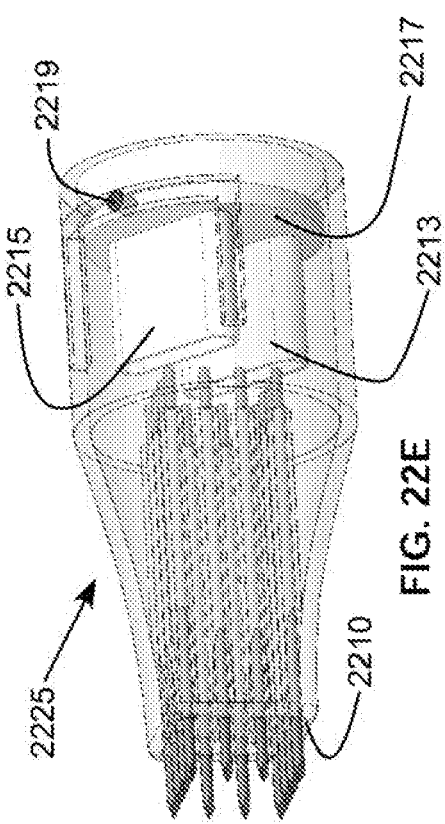

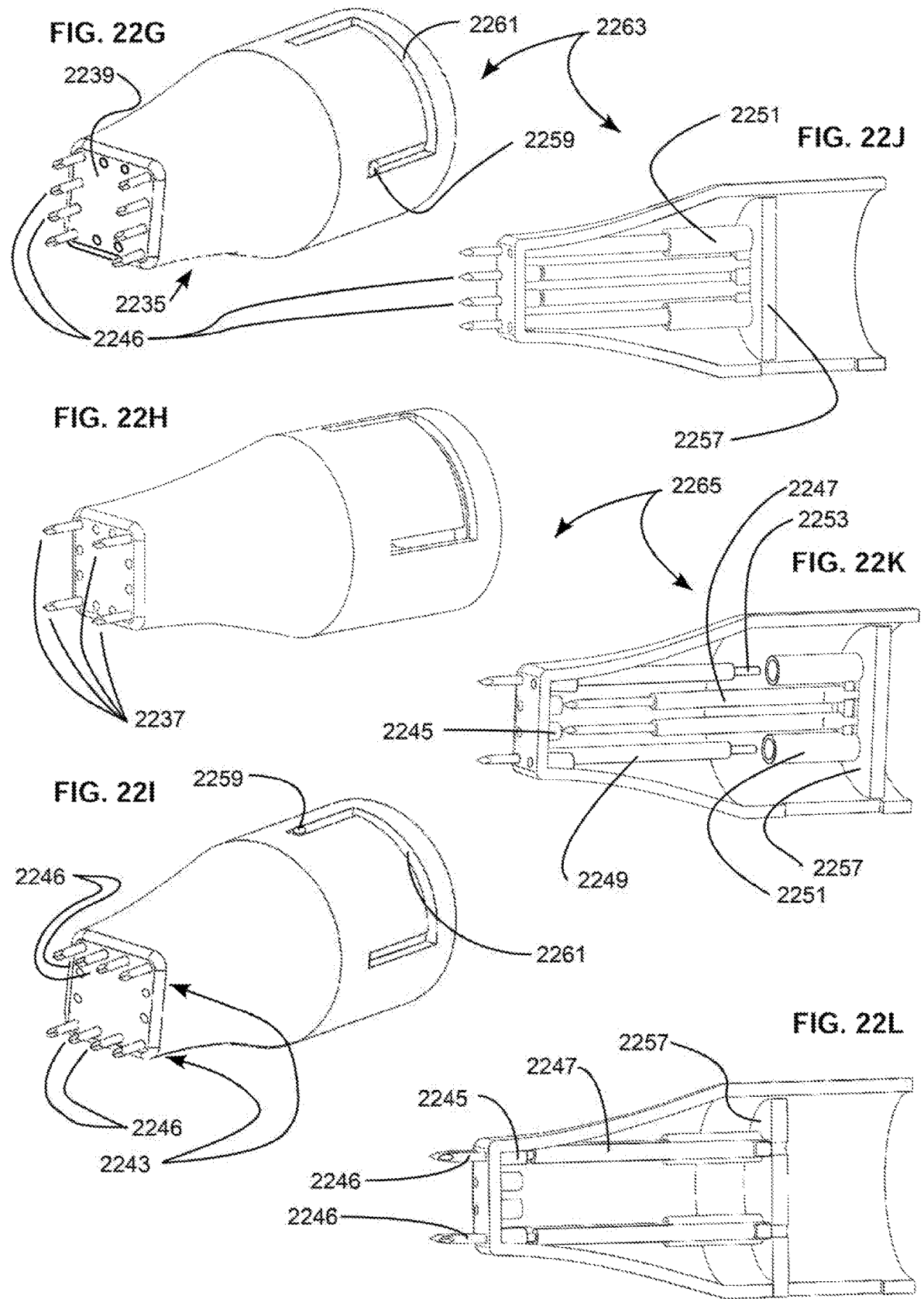

TREATMENT OF TISSUE BY THE APPLICATION OF ENERGY

CROSS REFERENCE TO RELATED APPLICATIONS

This patent application claims priority to U.S. Provisional Patent Application No. 62/542,711, filed on Aug. 8, 2017 (titled "TREATMENT OF SKIN BY SELECTIVE ANUCLEATION OF EPIDERMAL CELLS") and to U.S. Utility patent application Ser. No. 15/973,254, filed on May 7, 2018 (titled "TREATMENT OF TISSUE BY THE APPLICATION OF ENERGY", all herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

Specifically incorporate by reference in their entirety are each of: U.S. patent application Ser. No. 15/484,550, filed Apr. 11, 2017, U.S. patent application Ser. No. 13/631,618 filed Sep. 28, 2012 (now U.S. Pat. No. 9,656,055), and U.S. patent application Ser. No. 13/710,077, filed Dec. 12, 2011.

FIELD

This disclosure relates to treatment of tissue by the application of pulsed electric fields, such as nanosecond electrical pulses. The treatment may selectively and specifically destroy the nuclei of treated cells (e.g., epithelial cells) without provoking a significant inflammatory response, and while sparing the adjacent non-cellular tissue.

BACKGROUND

The application of destructive modalities for the treatment of tissue is well known. For example, many skin treatments, including treatment of skin disorders, by the application of thermal modalities is well known in dermatology. Thermal treatments in particular, including the use of liquid nitrogen (e.g., −196° to −210° C.) to treat or remove affected skin, are well known, but may result in severe disruption and immediate necrosis of skin cells and bursting of the cell membrane, leading to an acute inflammation response, loss of melanocytes, and damage to the dermis, that can result in scar tissue formation and an abnormal appearance.

Other thermal treatment modalities that result in tissue destruction include tissue heating generated by laser or radio frequency devices which may effectively burn the tissue (including skin) and may cause immediate cell necrosis and destruction of cell membranes and may also provoke an inflammatory response and suffer from the same drawbacks as extreme cold. It would be beneficial to provide therapies, and in particular, non-thermal therapies, which produce a minimal, if any, local inflammatory response. As applied to dermal tissue, it would be particularly helpful to provide for the formation of new epidermal tissue with reduced or no significant scarring and a normal appearance after restoration of the epidermal surface after a normal healing period.

Ultra-short, high-field strength electric pulses have been described for electroperturbation of biological cells. For example, electric pulses may be used in treatment of human cells and tissue including tumor cells, such as basal cell carcinoma, squamous cell carcinoma, and melanoma. See, e.g., Garon et al. "In Vitro and In Vivo Evaluation and a Case Report of Intense Nanosecond Pulsed Electric Field as a Local Therapy for Human Malignancies", *Int. J. Cancer*, vol. 121, 2007, pages 675-682, incorporated herein by reference it its entirety.

The voltage induced across a cell membrane may depend on the pulse length and pulse amplitude. Pulses longer than about 1 microsecond may charge the outer cell membrane and lead to opening of pores. Permanent openings may result in instant or near instant cell death. Pulses shorter than about 1 microsecond may affect the cell interior without adversely or permanently affecting the outer cell membrane and result in a delayed cell death with intact cell membranes. Such shorter pulses with a field strength varying, for example, in the range of 10 kV/cm to 100 kV/cm may trigger apoptosis (i.e. programmed cell death) in some or all of the cells exposed to the described field strength and pulse duration. These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Application No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Application No. 2008/0231337; and Sanders et al. "Nanosecond Pulse Generator", U.S. Patent Application No. 2010/0038971. The entire content of these publications is incorporated herein by reference.

Described herein are methods and apparatuses for the treatment of tissues, including skin, an in particular the treatments of skin disorders, which may address the issues raised above. These methods and apparatuses may target the nuclei of epidermal cells specifically, including the use of ultra-short, high field strength electric pulses.

SUMMARY OF THE DISCLOSURE

The methods, systems and apparatuses described herein generally describe the application of electric energy treatment(s) to tissue to form a lesion in the tissue while permitting healing. Skin tissue in particular is described as a possible target of the methods and apparatuses described herein; however, it should be noted that these methods and apparatuses are not limited to the treatment of skin.

For example, in some variations, described herein are methods and apparatuses for applying a treatment to a tissue from a plurality of electrodes by dividing the treatment (e.g., treatment dose) into two or more parts, and rotating the applicator tip so that the electrodes apply the energy to the same portion of tissue from multiple different rotational orientations during the treatment. The inventors have surprisingly found that rotation of the applicator tip part way through the treatment (e.g., approximately halfway through the treatment) requires substantially fewer pulses, e.g., less energy, in order to get an equivalent treatment compared to treatments in which the applicator tip is not rotated, and it provides further benefits as disclosed herein. For example, rotating the treatment tip having a pattern of electrodes by 90 degrees during treatment results in similar sized treatment-induced lesions using fewer treatment pulses compared to treatments applied with more pulses but without rotating electrodes.

Thus, described herein are methods and apparatuses for rotating the treatment electrodes partway through a treatment. For example, described herein are methods of treating a tissue by applying pulsed electrical energy (in some examples comprising a plurality of nanosecond electrical pulses having a pulse duration of between 0.1 ns and 1000 ns), wherein the treatment is divided into a first portion and a second portion. In some implementations, the method may include: contacting the tissue with an applicator tip (e.g., treatment tip) having a pattern of electrodes; applying the first portion of the treatment to a region of the tissue through the pattern of electrodes with the pattern of electrodes contacting the region of the tissue in a first orientation; and applying the second portion of the treatment to the region of the tissue in the same pattern of electrodes a second orientation that is rotated relative to the first orientation. The rotation may be about a line of rotation through the plurality of electrodes (e.g., a midline through the treatment tip and/or though the plurality of electrodes). The same electrodes of the treatment tip may form the pattern of electrodes applied in the first orientation as in the second orientation; also, the pattern may be formed by all of the electrodes of the treatment tip.

The treatment tip (and therefore the pattern of electrodes) may be rotated any appropriate amount, including, e.g., between +/−1 degree and 359 degrees, between +/−1 degree and 179 degrees, between +/−5 degrees and +/−175 degrees, between +/−70 degrees and 110 degrees, etc. For example, applying the second portion may comprise applying the second portion of the pulsed electrical treatment through the electrodes in the second orientation that is rotated between 80 degrees and 100 degrees relative to the first orientation. Applying the second portion may comprise applying the second portion of the pulsed electrical treatment through the electrodes in the second orientation that is rotated 90 degrees relative to the first orientation. Also, a degree or amount of rotation from the first orientation to the second orientation may be user selected (for example, through a user interface) or automatically directed by a controller.

Generally, the treatment before and after rotation is applied to the same region of the tissue. For example, applying the second portion may comprise applying the second portion so that the second orientation overlaps with the first orientation on the first region of the tissue.

The treatment may be divided up into any number of portions (e.g., 2, 3, 4, 5, 6, etc.). In some variations the tissue may be divided up into two portions. In general, the first portion of the pulsed electrical treatment may be between 30% and 70% of the total treatment (e.g., treatment dose). For example, the first portion of the treatment may be between 40% and 60% of the pulsed electrical treatment. The first portion of the pulsed electrical treatment may be half of the treatment.

Any appropriate type of electrode may be used, including penetrating electrodes (e.g., needle electrodes, blade electrodes, etc.) or non-penetrating electrodes (e.g., surface electrodes). In some variations the treatment tip includes an array of needle electrodes. The electrodes may be fixed relative to the distal face of the treatment tip, or they may be configured to retract relative to the treatment tip (e.g., retract into the treatment tip).

Rotation of the electrodes (e.g., including rotation of the treatment tip holding the pattern of electrodes) may include removing the treatment tip and/or electrodes from the tissue before rotation. For example, the method may include removing the plurality of electrodes from the region of the tissue, rotating the applicator tip and re-applying the plurality of electrodes to the region of the tissue before applying the second portion of the pulsed electrical treatment.

In any of the methods described herein, the rotation of the electrodes may be performed manually, semi-manually, or automatically. The rotation of the electrodes (e.g., rotation of the applicator, applicator tip and/or the pattern of electrodes) between different portions of the treatment may be performed robotically. In addition, any or all of the steps of the methods disclosed herein, including removing, rotating and reapplying the electrodes, as well as coordinating application of the pulsed electrical energy, may be performed by a robotic system, for example, under computer control. It may be that the rotation of the pattern of electrodes is carried out by way of a mechanism, wherein the mechanism comprises an actuator operable to be manually actuated by a user causing rotation of the pattern of electrodes; or the mechanism comprises a processor having a set of instructions operable to be executed causing rotation of the pattern of electrodes.

According to another aspect, in some examples described herein, instead of rotating the applicator tip, a pattern of active electrodes may be rotated to achieve the benefits described above. In some variations the pattern of electrodes applying energy to the same region of tissue may be rotated by switching the electrodes (either mechanically and/or electrically). For example, the pattern of electrodes on the tip of the applicator may be formed from a sub-set of electrodes available on the treatment tip. The apparatus may electrically and/or mechanically switch which electrodes form the pattern, and therefore, the orientation of the pattern on the applicator tip. Thus, the methods may include rotating the pattern of electrodes of the applicator tip on or in the region of the tissue without removing the applicator tip from the region of the tissue. For example, the tissue may be contacted during treatment with an applicator tip having an array of electrodes in which the pattern of electrodes is formed of a first subset of active electrodes from the array of electrodes; further wherein applying the second portion of the pulsed electrical treatment may include forming the pattern from a second subset of active electrodes from the array of electrodes in which the pattern formed by the second subset is rotated relative to the first subset. In some examples, the method of treating a tissue with pulsed electrical energy comprising a plurality of electrical pulses is provided. The method comprises applying pulsed electrical energy from a subset of electrodes of an array of electrodes in a first pattern; and partway through the pulsed electrical treatment switching to a second subset of electrodes of the array of electrodes to apply electrical energy in a second pattern that is a rotated version of the first pattern. The switching may be electrical, e.g., switching which electrodes are active (applying energy) and which are not active. In some variations the switching may be mechanical, e.g., changing the mechanical connection of the different electrodes applying power. In some variations the electrodes may be switched by moving electrodes into or out of the tissue.

In general, applying the pulsed electrical treatment may include applying a pulsed electrical treatment that does not disrupt cell membranes within the tissue.

The treatment may include applying a plurality of pulses each having a duration of between 0.1 ns and 1000 ns and. For example, applying the first portion and/or second portion of the pulsed electrical treatment comprises applying a plurality of pulses each having a duration of between 0.1 ns and 1000 ns and a peak field strength of at least 1 kV/cm.

According to one example of general methodology, described herein is a method of treating a tissue with a pulsed electrical treatment comprising a plurality of electrical pulses, wherein the pulsed electrical treatment is divided into at least a first portion and a second portion. The method comprises: contacting the tissue with an applicator tip having a plurality of electrodes; applying the first portion of the pulsed electrical treatment to a region of the tissue in a pattern of electrodes from the plurality of electrodes, the pattern of electrodes contacting the region of the tissue in a first orientation; and applying the second portion of the pulsed electrical treatment to the region of the tissue in the pattern of electrodes contacting the region of the tissue in a second orientation that is rotated relative to the first orientation. The pattern of electrodes in the second orientation may be formed by the same electrodes as the first orientation or some or all of them may be different. Also, the pattern may be formed by all of the electrodes of the plurality or electrodes, or only by a portion of the plurality of electrodes. For example, in some examples, the second portion of the pulsed electrical treatment is applied through the same plurality of electrodes. In other examples, the applicator tip comprises an array of electrodes in which the plurality of electrodes is a first subset of active electrodes forming the pattern of electrodes and applying the second portion of the pulsed electric treatment comprises forming the pattern from a second subset of active electrodes from the array of electrodes in which the pattern formed by the second subset is rotated relative to the first subset. The treatment in any of the above methods may be any appropriate duration. For example, the treatment may be between 10 seconds and 20 minutes, between 10 seconds and 10 minutes, between 10 second and 5 minutes, less than 10 minutes, less than 7 minutes, less than 5 minutes, less than 4 minutes, etc. For example, applying the first and second portions of the pulsed electrical treatment may comprise applying for less than 5 minutes.

The second orientation may be rotated about a midline through the plurality of electrodes.

As mentioned, any appropriate tissue, e.g., skin, liver, kidney, lung, etc. including tumor (e.g., tumorous tissue) is within a scope of the present disclosure. For example, contacting the tissue may comprise contacting a skin tissue. Any of these methods may be methods of treating the tissue, including methods of selectively removing tissue. For example, the skin tissue treated may comprise one or more of: seborrheic keratosis, keloids, molluscum contagiosum, sebaceous hyperplasia, syringoma, congenital capillary malformation (port-wine stain), melasma, actinic keratoses, dermatosis papulosa nigra, angiofibroma, skin tumors, and warts. Contacting may comprise contacting a tumor tissue.

As will be described in greater detail below, applying the pulsed electrical treatment may increase a marker of inflammation within the first region of the tissue by less than 15%, wherein the marker of inflammation is one or of more of: fibroblast density, leukocyte density, Interleukin-6, Interleukin-8, Interleukin-18, Tumor necrosis factor-alpha, and C-reactive protein.

According to further examples, described herein are methods of treating a tissue with a pulsed electrical treatment comprising a plurality of nanosecond electrical pulses having a pulse duration of between 0.1 ns and 1000 ns, wherein the treatment is divided into a first portion and a second portion. The first portion may be between 30% and 70% of the pulsed electrical treatment (e.g., treatment duration). The method may include: contacting the tissue with an applicator tip having a plurality of electrodes in a pattern of electrodes; applying the first portion of the pulsed electrical treatment to a region of the tissue through the plurality of electrodes with the pattern of electrodes contacting the region of the tissue in a first orientation; removing the plurality of electrodes from the region of the tissue; rotating the applicator tip; re-applying the plurality of electrodes to the region of the tissue; and applying the second portion of the pulsed electrical treatment to the region of the tissue through the plurality of electrodes with the pattern of electrodes contacting the region of the tissue in a second orientation that is rotated relative to the first orientation.

A further method of treating a tissue with a pulsed electrical treatment, wherein the pulsed electrical treatment is divided into a first portion and a second portion, may include: contacting a region of the tissue with an applicator tip having a plurality of electrodes in a pattern of electrodes; applying the first portion of the pulsed electrical treatment to the region of the tissue through the plurality of electrodes with the pattern of electrodes contacting the region of the tissue in a first orientation; removing the plurality of electrodes from the region of the tissue; re-applying the plurality of electrodes to the region of the tissue with the pattern of electrodes contacting the region of the tissue in a second orientation that is rotated relative to the first orientation; and applying the second portion of the pulsed electrical treatment to the first region of the tissue through the plurality of electrodes. In some variations, the second orientation may be rotated between 40 degrees and 100 degrees relative to the first orientation, for example, 90 degrees. According to some embodiments, applying the first portion of the pulsed electrical treatment and applying the second portion of the electrical treatment each comprises applying electrical pulses to the region to de-nucleate cells within the region without provoking a substantial inflammatory response, so that after the treatment the tissue forms a necrotic crust over the region so that when the necrotic crust is removed new tissue is exposed.

Also described herein are apparatuses (e.g., systems and devices) configured to perform any of these methods, including methods of treating the tissue with pulsed electrical energy and rotating the pattern of electrodes partway through the treatment. For example, a system may comprise a pulse generator; an applicator tip having a plurality of electrodes in a pattern of electrodes, the applicator tip configured to apply energy from the pulse generator to the plurality of electrodes; a controller configured to control, at least partially, operation of the pulse generator to: apply a first portion of a pulsed electrical treatment to a region of tissue through the plurality of electrodes with the pattern of electrodes contacting the region in a first orientation and apply a second portion of the pulsed electrical treatment to the region with the pattern in a second orientation that is rotated relative to the first orientation; and a mechanism configured to cause rotation of the pattern between the first and the second configuration. It may be that the mechanism comprises an actuator operable to be manually actuated causing rotation of the pattern of electrodes; or the mechanism comprises a processor having a set of instructions operable to be executed causing rotation of the pattern of electrodes. In some implementations, the second portion of the pulsed electrical treatment may be applied through the same plurality of electrodes and wherein the second orientation is rotated about a midline through the plurality of electrodes. In other implementations, the applicator tip may comprise an array of electrodes in which the plurality of electrodes is a first subset of active electrodes forming the pattern, and wherein applying the second portion of the pulsed electrical treatment comprises forming the pattern from a second subset of active electrodes of the array of electrodes in which the pattern formed by the second subset is rotated relative to the first subset.

According to some examples a system for treating tissue may include: a pulse generator; an applicator configured to apply energy from the pulse generator to a plurality of electrodes at a treatment tip of the applicator, wherein the plurality of electrodes is arranged about a line of rotation through the treatment tip; and a controller configured to control, at least partially, operation of the pulse generator and/or the applicator. The controller may comprises a processor operable to cause the controller to: apply a first portion of the pulsed electrical treatment from a first pattern of electrodes of the plurality of electrodes at the treatment tip; and apply a second portion of the pulsed electrical treatment through the plurality of electrodes in a second pattern of electrodes wherein the second pattern of electrodes is the first pattern of electrodes rotated about the line of rotation. The processor may have a set of instructions operable to be executed by the processor.

The set of instructions may further cause the processor and/or controller to rotate the treatment tip to form a second pattern of electrodes of the plurality of electrodes at the treatment tip. In some variations, the set of instructions further causes the processor to switch electrical or mechanical connections of at least some of the electrodes in the plurality of electrodes to form the second pattern of electrodes of the plurality of electrodes at the treatment tip.

In some examples, the path for energy may be through mechanical connections, for example, through at least two connectors, each having plugs and jacks to facilitate a first connection orientation establishing a first pattern of active electrodes and a second connection orientation establishing a second pattern of active electrodes.

In one configuration the plurality of electrodes are needles positioned substantially along polygonal (e.g., square, triangular, rectangular, multi-sided) or curved perimeter sides of an applicator tip end wall holding needles fixed relative to the applicator tip (also referred to as a treatment tip). Curved perimeter comprises shapes such as round or oval, for example. In such example, at least two connectors (e.g., banks of connectors) connect to parallel perimeter rows of needle electrodes, for example, the rows on opposite sides of the applicator tip end wall. The needle electrodes to which there is no connection remain electrically floating and inactive.

In further examples, a pattern of active electrodes is rotated using mechanical connections and an array of electrodes, where some of the electrodes may be stationary or fixed in place and other electrodes may be movable, for example, to retract and extend. The system may include a path for energy through mechanical connections, for example, through at least two pairs of connectors, each may have a plug and jack to facilitate a first connection orientation establishing a first energized electrode pattern and a second connection orientation establishing a second energized electrode pattern.

For example, the plurality of electrodes may include needles that may be fixed substantially at polygonal perimeter side corners of an applicator tip end wall, which for convenience may be referred to as "fixed or stationary electrodes". The plurality of electrodes may also include movable needle electrodes that may be disposed between the stationary electrodes and attached such that they can be moved, for example, retract and extend, relative to the end wall of the applicator tip. The applicator or treatment tip may also include at least two pairs of connectors, which electrically connect to parallel perimeter rows and/or columns of needle electrodes, for example, on opposite sides of the applicator tip end wall.

The at least two pairs of connectors may be fixed to a movable switch plate. By retracting the movable electrodes of the respective parallel or opposite sides of the polygonal or curved perimeter (for example, a square, rectangular or round perimeter) and rotating the switch plate, a pattern of the active electrodes may be rotated, for example, from the active columns to the active rows, or the other way around.

The line of rotation may be a midline through the plurality of electrodes.

The pulse generator may be configured to deliver pulses having a pulse duration of between 0.1 ns and 1000 ns. In some variations, the pulse generator is configured to deliver a plurality of pulses each having a duration of less than 1 microsecond and a peak field strength of at least 1 kV/cm.

Any of these apparatuses may include an actuator (e.g., motor, driver, impeller, etc.) configured to rotate an applicator or at least a portion of the distal tip of the applicator. In some implementations it can be done under the control of the controller and/or processor, in other implementations an actuator may be actuated manually by a user, for example, medical professional. It may be that the actuator forms part of a mechanism, in which the actuator is operable to be manually actuated causing rotation of the pattern of electrodes. Alternatively, the mechanism may comprise a processor having a set of instructions operable to be executed causing rotation of the pattern of the electrodes.

The system may include an electrical switching module configured to switch between the first pattern and the second pattern of the electrodes, for example, between a first and a second subset of active electrodes. Alternatively or additionally, the system may include mechanical switches for controlling which electrodes are active or inactive.

The second pattern may be identical to the first pattern but rotated any amount (e.g., between 40 degrees and 100 degrees, between 20 and 180 degrees, between 30 and 80 degrees, etc.) relative to the first pattern. The degree or amount of rotation from the first orientation to the second orientation may be user selected (for example, through a user interface) or automatically directed by a controller, for example, through the set of instructions.

Any of these systems may be robotic systems wherein the applicator comprising a treatment tip with an array of electrodes is coupled to a moveable arm. For example, the robotic system may receive instructions from the controller and rotate one or both of the applicator and the treatment tip to change orientation of the pattern or electrodes.

For example, a system for applying pulsed electrical treatment to a tissue may include: a movable arm (e.g., robotic arm); an applicator operatively coupled to the movable arm, the applicator configured to apply pulsed electrical energy from a plurality of electrodes of the applicator; and a processor comprising a set of instructions for executing operations, the set of instructions including instructions for: moving the movable arm to contact a region of the tissue with the applicator; directing application of a first portion of the pulsed electrical treatment to the region of the tissue with a pattern of electrodes contacting the region of the tissue in a first orientation; and directing application of a second portion of the pulsed electrical treatment to the region of the tissue with the pattern of electrodes contacting the region of the tissue in a second orientation that is rotated relative to the first orientation.

In some examples, the robotic system may include a navigation interface comprising, for example, an image acquisition device and the navigation interface may be configured to receive imaging data. In general, the navigation interface may determine the distance between the tissue (as well as the location of the target treatment site on the tissue) and the plurality of electrodes/treatment tip, and/or the orientation of the plurality of electrodes/treatment tip and the tissue, to allow control and guidance of the treatment tip relative to the tissue.

The applicator may be operably connected to the movable arm, such as held by the movable (e.g., robotic) arm. Alternatively, the applicator may be integrated into the movable arm.

The set of instructions may comprise instructions for moving the applicator so that that the plurality of electrodes is moved to the second orientation. For example, the set of instructions may comprise instructions for withdrawing the applicator from the tissue, rotating the applicator so that that the plurality of electrodes is moved to the second orientation, and reapplying the applicator tip to the region of the patient tissue.

As mentioned, any of the methods and apparatuses (e.g., devices and systems, including applicators) described herein may be used to treat skin, including treating skin disorders, including but not limited to seborrheic keratosis, keloids, molluscum contagiosum, acrocordon, psoriasis, papilloma, human papilloma virus (HPV), melanoma, melasma, sebaceous hyperplasia, syringoma, congenital capillary malformation (port-wine stains), melasma, actinic keratosis, dermatosis papulosa nigra, angiofibroma, skin tumors, aged skin, wrinkled skin, and warts. These methods and apparatuses may also be used for cosmetic skin treatments, including tattoo removal, hair follicle destruction, scar reduction and wrinkle reduction.

Also described herein are methods and apparatuses for treating a skin lesion of a mammal (including human and non-human mammals) that may generally include the application of pulsed electrical energy to a defined region of a patient's skin in which pattern of electrodes applying the treatment to the defined region are rotated partway through the treatment. In general, these treatments make targeted cells within the epidermal or dermal region non-viable, typically within 2-48 hours following treatment. For example, the methods described herein may de-nucleate cells (and particularly epidermal cells), forming "ghost cells" that may have intact cell membranes, but may lack a distinct cell nucleus. Furthermore, the application of the treatment may be configured (e.g., titrated, limited, arranged, etc.) so that the de-nucleation does not result in a substantial inflammatory response. For example, in skin, as a result of the targeted de-nucleation of the epidermal cells in the target region, the skin in that region may form a necrotic crust, and new epidermis may form below this necrotic crust so that when the necrotic crust is removed, the new epidermis is exposed. Rotating the pattern of the electrodes applying the energy to the skin in the target region may result a higher efficiency treatment, as less energy may be needed to treat an equivalent-sized (or larger) region. This new epidermis may include epidermal cells (e.g., newly formed epidermal cells) that have healthy nuclei, including a normal (as compared to other adjacent skin regions) distribution of melanocytes, and normal elastin distribution and density. Thus, unlike other methods of treating skin, e.g., to remove skin lesions, the resulting skin region may have little or no scarring and/or discoloration.

In some variations, the pattern of electrodes applying the electrical energy to a target skin region is not rotated during treatment. For example, also described herein are methods of treatment of a skin lesion of a mammal (including human and non-human mammals) that may generally include the application of pulsed electrical energy to a defined region of a patient's skin. In general, these treatments make targeted cells within the epidermal or dermal region non-viable, typically within 2-48 hours following treatment. The methods described herein may de-nucleate cells (and particularly epidermal cells), forming ghost cells. The application of the treatment may be configured (e.g., titrated, limited, arranged, etc.) so that the de-nucleation does not result in a substantial inflammatory response. For example, in skin, as a result of the targeted de-nucleation of the epidermal cells, the skin in the region may form a necrotic crust, and new epidermis may form below this necrotic crust so that when the necrotic crust is removed, the new epidermis is exposed. This new epidermis may include epidermal cells (e.g., newly formed epidermal cells) that have healthy nuclei, including a normal (as compared to other adjacent skin regions) distribution of melanocytes, and normal elastin distribution and density, with little or no scarring and/or discoloration.

For example, described herein are methods of treating a skin disorder, the methods including: applying a pulsed electrical treatment to a region of the skin to de-nucleate epidermal cells within the region without provoking a substantial inflammatory response, so that the skin forms a necrotic crust over the region of the skin and forms new epidermis below the necrotic crust so that when the necrotic crust is removed the new epidermis is exposed. The methods may comprise restoring elastin integrity of the skin. Any of these methods of treating a skin disorder may include the steps of rotating the pattern of the electrodes applying the pulsed electrical treatment partway through the applying of the treatment. This may include diving the treatment up into a first part and a second part and rotating the pattern of electrodes used in the first part of the treatment and applying the rotated pattern to the same region of the skin during the second part of the treatment.

Any appropriate pulsed electrical treatment may be used. In some variations, a treatment that specifically de-nucleates epidermal cells without provoking a substantial inflammatory response may be used. In particular, the treatment may include the use of nano-pulse stimulation (NPS), e.g., the application of nanosecond electrical pulses having a pulse duration of between 0.1 ns and 1000 ns and a high field density, e.g., a field strength of at least 1 kV/cm or greater to the epidermal cells or other tissue cells. However, other treatments for specifically de-nucleating epidermal cells may include optical therapies (e.g., the use of photosensitive nuclear stains in conjunction with optical stimulation), and the like. Generally, the treatment according to the present disclosure may include any treatment that does not disrupt the cell membrane of the epidermal cells.

For example, applying the treatment may include inserting a pair of electrodes (or a plurality of electrodes) into the region of the skin and applying a plurality of high voltage nanosecond electrical pulses between the electrodes. Alternatively or additionally, applying the treatment may comprise applying a pair of electrodes against the region of the skin (e.g., non-invasively) and applying a plurality of high voltage nanosecond electrical pulses from the electrodes. A non-conductive gel or other material may be used, and/or may be integrated into the electrodes and/or applicator.

As mentioned, applying the treatment (e.g., pulsed electrical energy treatment) may comprise applying a plurality of pulses each having a duration of between 0.1 ns and 1000 ns and a peak field strength of at least 1 kV/cm. Applying the treatment may include applying the treatment for less than 10 minutes (e.g., less than 1 second, less than 2 seconds, less than 5 seconds, less than 10 seconds, less than 15 seconds, less than 30 seconds, less than 45 seconds, less than 1 minute, less than 2 minutes, less than 3 minutes, less than 4 minutes, less than 5 minutes, etc.).

In general, applying the treatment does not provoke a substantial increase in inflammation. For example, applying the treatment may increase a marker of inflammation within the region of the skin by less than a predefined percentage (e.g., 5% or less, 10% or less, 15% or less, 20% or less, etc.). The marker of inflammation may be one or of more of: leukocyte density, Interleukin-6, Interleukin-8, Interleukin-18, Tumor necrosis factor-alpha, and C-reactive protein. In particular, a marker of acute inflammation such as the leukocyte density, may be increased by less than a predefined percentage (e.g., 15%) compared prior to treatment.

As mentioned above, the methods and apparatuses described herein may be used to treat a skin disorder, including but not limited to one or more of: seborrheic keratosis, keloids, molluscum contagiosum, sebaceous hyperplasia, syringoma, congenital capillary malformation (port-wine stains), melasma, actinic keratosis, dermatosis papulosa nigra, angiofibroma, skin tumors, and warts. Any of these methods may also be used to treat otherwise healthy skin including cosmetic blemishes, such as tattoos, wrinkles, and scars.

For example, described herein are methods of treating a patient's skin, the method comprising: positioning a set of electrodes in communication with a region of a patient's skin; applying a plurality of high-field strength, ultra-short electrical pulses to the region from the set of electrodes to de-nucleate epidermal cells, such that the skin forms a necrotic crust over the region of the skin and forms new epidermis below the necrotic crust so that when the necrotic crust is removed the new epidermis is exposed; wherein the high-field strength, ultra-short electrical pulses comprise a plurality of pulses each having a duration of between 0.1 ns and 1000 ns and a peak field strength of at least 1 kV/cm.

Any of these methods may include inserting a pair of electrodes into the patient's skin before applying the plurality of high-field strength, ultra-short electrical pulses. For example, the electrodes may be inserted into the outer layers of skin to a depth of less than 5 mm, less than 4 mm, less than 3 mm, less than 2 mm, etc. The skin may be prepared ahead of time, e.g., washed, shaved, roughened, etc. Alternatively or additionally, the high-field strength, ultra-short electrical pulses may be applied transdermally, without puncturing the skin. For example, any of these methods may include applying the set of electrodes on the surface of the patient's skin before applying the plurality of high-field strength, ultra-short electrical pulses. In such variations one or more conductive or non-conductive gels or other materials may be applied to the skin, including to the electrode contact points and/or the region between them. For example, a non-conductive or lower-conductance gel may be used. Alternatively or additionally, a gel (low-conductance or non-conductive gels) may be used with needle electrodes.

While in some variations a pair of electrodes may be used, in other variations more than two electrodes (e.g., two or more active electrodes and two or more ground electrodes) may be used. The active electrodes may be coupled together; the ground electrodes may be coupled together.

Applying the plurality of high-field strength, ultra-short electrical pulses may include applying the high-field strength, ultra-short electrical pulses for less than a predetermined time (e.g., 1 second or less, 2 seconds or less, 5 seconds or less, 10 seconds or less, 15 seconds or less, 30 seconds or less, 45 seconds or less, 1 minute or less, 2 minutes or less, 3 minutes or less, 4 minutes or less, 5 minutes or less, 10 minutes or less, 15 minutes or less, etc.) and/or for a predetermined number of pulses (e.g., between 2 and 30 pulses, between 2 and 60 pulses, between 2 and 120 pulses, between 2 and 240 pulses, between 2 and 680 pulses, etc.). The pulses may be applied at any appropriate frequency. For example, the plurality of high-field strength, ultra-short electrical pulses may be applied between 0.05 Hz and 100 Hz (e.g., between 0.05 Hz and 20 Hz, between 0.05 Hz and 10 Hz, etc.).

As mentioned above, applying the plurality of high-field strength, ultra-short electrical pulses may increase a marker of inflammation within the region of the skin by less than a predetermined amount (e.g., less than 5%, less than 10%, less than 15%, etc.), wherein the marker of inflammation is one or of more of: leukocyte density, Interleukin-6, Interleukin-8, Interleukin-18, Tumor necrosis factor-alpha, and C-reactive protein. In particular, the marker may be an acute inflammatory marker, such as (but not limited to) leukocyte density.

The step of positioning the pair of electrodes may comprise positioning the pair of electrodes in communication with a region of skin having one or more of: a seborrheic keratosis, a keloid, a molluscum contagiosum, a sebaceous hyperplasia, a syringoma, a congenital capillary malformation (port-wine stain), a melasma, an actinic keratosis, a dermatosis papulosa nigra, an angiofibroma, a wart, and a tattoo.

In general, when applying nano-pulse stimulation (NPS), the electrical energy applied to the skin lesion may be in the form of one or more electrical pulses. The pulse duration may be at least 0.01 nanoseconds (ns) at the full-width-half-maximum (FWHM). The pulse duration may also be at least 1 ns at FWHM, or the pulse duration may be at least 5 ns at FWHM. The pulse duration may be 1,000 ns or shorter.

The methods and apparatuses may be used to treat skin, including treating a skin lesion. As used herein, a skin lesion may refer to any deviation of skin from a healthy or a normal condition. Examples of skin lesions are skin diseases, conditions, injuries, defects, abnormalities or combinations thereof. For example, such skin lesions include malignancies (such as basal cell carcinomas, squamous cell carcinomas and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon), or combinations thereof. In one embodiment, the skin lesion is basal cell carcinoma (including papilloma), squamous cell carcinoma, actinic keratosis, warts, or combinations thereof. The skin lesion may also include aged skin, wrinkled skin or damaged skin. An example of the damaged skin is the skin damaged by sun radiation.

As mentioned, the duration of the pulse may be in the range of 0.01 ns to 1,000 ns. The duration of the pulse may also be in the range of 1 ns to 600 ns (e.g., 10 ns to 500 ns, 10 ns to 400 ns, etc.). In some implementations, the duration of the pulses may be in a picosecond ranges, or microsecond ranges, just to name a few. The applied electrical energy per volume of the skin lesion may be at least 10 mJ/mm$^3$ or at least 100 mJ/mm$^3$ or at least 1,000 mJ/mm$^3$. The applied electrical energy per volume of the skin lesion may also be in the range of 0.1 mJ/mm$^3$ to 10,000 mJ/mm$^3$.

The electrical field produced by each pulse may be at least 1 kV/cm at the peak amplitude of the pulse. The electrical field produced by each pulse may also be at least 10 kV/cm at the peak amplitude of the pulse. The electrical field produced by each pulse may be in the range of 1 kV/cm to 1,000 kV/cm at the peak amplitude of the pulse (e.g., the electrical field produced by each pulse may be in the range of 10 kV/cm to 100 kV/cm, 15 kV/cm to 50 kV/cm, 20 kV/cm to 30 kV/cm, etc.).

The number of electrical pulses during a single treatment may be at least 1. The number of pulses may also be at least 100. The number of pulses may be at least 1,000. The number of pulses may be less than 10,000. For example, the number of pulses may be between 20 and 200, between 30 and 150, between 30 and 100, etc. Pulses may be applied at a frequency of between 1 and 100 Hz, e.g., between 1 and 50 Hz, between 1 and 25 Hz, between 1 and 20 Hz, between 1 and 10 Hz, between 2 and 6 Hz, etc. The treatment time per session may be between 1 second and 60 seconds, between 5 seconds and 30 seconds, between 5 seconds and 20 seconds, etc.

The treatment may be an in vivo treatment of a skin lesion of a human comprising at least one treatment session, i.e. administration of the electrical energy to the skin lesion by physician at an office visit. The at least one treatment session may comprise applying electrical energy to the skin lesion of the human comprising delivering at least one electrical pulse with a pulse duration in the range of 0.01 ns to 1,000 ns, forming an electrical field in the lesion, and thereby at least preventing growth of the lesion. This pulse duration may also be in the range of 1 ns to 600 ns (e.g., 1 ns to 300 ns, 1 ns to 200 ns, etc.).

The treatment of a lesion may also comprise a plurality of treatment sessions. For example, it may comprise at least two treatment sessions or at least three treatment sessions. As used herein, the term skin lesion may also be referred to as a skin disorder, and/or lesions may be formed on or in the skin as part of a skin disorder. The methods described herein may be used to treat either the skin disorder and/or a lesion of a skin disorder.

Also described herein are apparatuses (e.g., systems and devices) for use in therapy, for use in treating tissue, or for performing any of these methods, including the methods of treating a skin disorder. For example, according to one aspect of the present disclosure a system for treating tissue is provided. The system comprises a pulse generator; a set of electrodes; and a controller configured to control, at least partially, operation of the pulse generator. The controller is operable to cause the pulse generator to generate and apply through the set of electrodes a pulsed electrical treatment to a region of tissue to de-nucleate cells within the region without provoking a substantial inflammatory response, so that the tissue forms a necrotic crust and forms new tissue below the necrotic crust so that when the necrotic crust is removed the new tissue is exposed.

The system for treating tissue may be a system for treating a skin disorder or skin lesion. Thus, the system used for the treatment of the skin lesion may include an applicator tip that comprises at least one delivery electrode and at least one ground electrode. The applicator (e.g., applicator tip) may be any of the applicator tips described herein, including arrays of electrodes and/or applicator tips having a pattern of electrodes that may be rotated.

The pulse generator may be configured to provide pulses (including but not limited to nanopulses) to be delivered by the applicator. The pulse generator and/or tip may be controlled by the controller. The controller may include one or more processors that may be configured to perform any of the treatment methods described herein. The one or more processors may be incorporated into the controller or may be a separate part. The controller and/or processor may include one or more memories, datastores, or the like that may be operationally connected to the processor(s).

The set of instructions executable by the processor(s) of the controller may be configured to perform any of the methods described herein. For example, the set of instructions may be configured to apply the pulsed electrical treatment to de-nucleate cells within the tissue (e.g., skin tissue). Thus, the set of instructions may control the timing (frequency, rate, duty cycle, etc.) of the applied electrical stimulation and/or the contact with the tissue.

For example, described herein are methods of treating a skin disorder generally comprising: applying a treatment to a region of the skin to make epidermal cells within the region non-viable (e.g., by destroying or degrading their nuclei and/or other internal organelles, typically without disrupting their cell membranes), without provoking a substantial inflammatory response, so that the skin forms a necrotic crust over the treated region of the skin and forms new epidermis below the necrotic crust so that when the necrotic crust is removed the new epidermis is exposed, while sparing the adjacent dermal tissue. Described herein are also systems configured to apply a treatment to a region of the skin to make epidermal cells within the region non-viable (e.g., by destroying or degrading their nuclei and/or other internal organelles, typically without disrupting their cell membranes), without provoking a substantial inflammatory response, such that the skin forms a necrotic crust over the treated region of the skin and forms new epidermis below the necrotic crust so that when the necrotic crust is removed the new epidermis is exposed, while sparing the adjacent dermal tissue. Alternatively, in some variations, the treatments described herein may be configured to provoke an immune response, particularly in non-dermal applications. All or some (e.g., greater than 60%, greater than 70%, greater than 80%, greater than 90%, greater than 95%, etc.) of the epidermal cells within the region may be made non-viable. The region typically includes a region around and/or between the electrodes applying the energy. For example, the region may include a region approximately 0.5 mm$^3$ around the electrodes, approximately 1 mm$^3$, approximately 1.5 mm$^3$, approximately 2 mm$^3$, approximately 3 mm$^3$, approximately 4 mm$^3$, approximately 5 mm$^3$, approximately 10 mm$^3$, etc. The size of the region may depend at least in part on the size and spacing of the electrodes, as well as the power applied.

Applying the treatment may comprise applying nanosecond electrical pulses having a pulse duration of between 0.1 ns and 1000 ns to the epidermal cells (e.g., 10 to 500 ns, 100 to 350 ns, 150 to 300 ns, etc.). As mentioned, applying the treatment may include applying a non-thermal treatment that does not disrupt the cell membrane of the epidermal cells.

The electrodes may be surface electrodes or penetrating electrodes. Either surface or inserted electrodes may be applied with a gel on the skin region, including a non-conductive or low-conductance gel; alternatively, a conductive gel may be used in some variations. Applying the treatment may comprise inserting a pair of electrodes into the region of the skin and applying a plurality of high voltage nanosecond electrical pulses between the electrodes. Alternatively or additionally, applying the treatment may comprise applying a pair of electrodes against the region of the skin and applying a plurality of high voltage nanosecond electrical pulses from the electrodes.

As mentioned above, applying the pulsed electrical treatment may comprises applying a plurality of pulses each having a duration of between 0.1 ns and 1000 ns and a peak field strength of at least 1 kV/cm (e.g., duration of between 10 to 500 ns, 100 to 350 ns, 150 to 300 ns, etc., and a field strength of between 1 kV/cm and 50 kV/cm, e.g., between 10 kV/cm and 40 kV/cm, between 20 kV/cm and 30 kV/cm, etc.). The treatment may be applied for less than 5 minutes (e.g., less than 1 minute, less than 30 seconds, less than 20 seconds, etc.).

Applying the treatment typically does not result in substantial inflammation. In other words, applying the treatment as described herein typically increases a marker of inflammation within the region of the skin by less than 15% (e.g., less than 14%, less than 13%, less than 12%, less than 11%, less than 10%, less than 9%, less than 8%, less than 7%, less than 5%, etc.), wherein the marker of inflammation is one or more of: fibroblast density, leukocyte density, Interleukin-6, Interleukin-8, Interleukin-18, Tumor necrosis factor-alpha, and C-reactive protein.

The skin disorder may be one or more of: seborrheic keratosis, keloids, molluscum contagiosum, sebaceous hyperplasia, syringoma, congenital capillary malformation (port-wine stain), melasma, actinic keratoses, dermatosis papulosa nigra, angiofibroma, and warts.

For example, a method of treating a patient's skin may include: positioning a pair of electrodes in communication with a region of a patient's skin; non-thermally destroying the viability of epidermal cells within the region of the patient's skin by applying a plurality of high-field strength, ultra-short electrical pulses to the region of the patient's skin from the pair of electrodes, without provoking a substantial inflammatory response within the region, so that the skin forms a necrotic crust over the region of the skin and forms new epidermis below the necrotic crust so that when the necrotic crust is removed the new epidermis is exposed; wherein the high-field strength, ultra-short electrical pulses comprise a plurality of pulses each having a duration of between 0.1 ns and 1000 ns and a peak field strength of at least 1 kV/cm. As mentioned, non-thermally destroying the viability of epidermal cells within the region of the patient's skin may comprise disrupting the viability of greater than 90% of the epidermal cells within the region of the patient's skin, wherein the region comprises at least a 1 mm$^3$ volume around the portion of the patient's skin in contact with the electrodes.

Positioning the pair of electrodes may comprise positioning the pair of electrodes in communication with a region of skin having one or more of: a seborrheic keratosis, a keloid, a molluscum contagiosum, a sebaceous hyperplasia, a syringoma, a congenital capillary malformation (port-wine stain), a melasma, an actinic keratosis, a dermatosis papulosa nigra, an angiofibroma, a wart, and a tattoo. Other and further features and advantages of the present disclosure will become apparent from the following detailed description when read in view of the accompanying figures.

BRIEF DESCRIPTION OF THE DRAWINGS

The novel features of the apparatuses and methods described herein are set forth with particularity in the claims that follow. A better understanding of the features and advantages of these apparatuses and methods will be obtained by reference to the following detailed description that sets forth illustrative embodiments, in which the principles of the invention are utilized, and the accompanying drawings of which:

In FIG. 6B, the treated epidermal cells appear as "ghost cells" in which the nuclei are missing; this image is taken one day post treatment. The tissue is human skin (abdominal skin) tissue.

In FIG. 7A, a histological section of treated human skin is shown fifteen (15) days after treatment, showing an initial lack of melanocytes. Melanocytes rapidly recover within 60 days post treatment, as shown in FIG. 7B (showing 9 distinct melanocytes, similar to nearby untreated/control skin). The rapid recovery of melanocytes is highly predictive of normal melanin production and full recovery of skin tone. The lack of a robust inflammatory response following treatment may enhance melanocyte recovery. Typically, injuries with a high amount of inflammation create a higher risk of long-term melanocyte suppression.

As shown in FIG. 8A, initially (e.g., 15 days post-treatment) there is some change in elastin near the surface of the skin, however, as shown in FIG. 8B, by 60 days post-treatment the elastin orientation and density is normal compared to nearby (e.g., control) tissue.

FIGS. 9A-9E illustrate a time course of human skin treated as described, de-nucleating epidermal cells within the region shown, without provoking a substantial inflammatory response. FIG. 9A shows skin one day following treatment. In FIG. 9B, the same region of skin is shown seven days post-treatment, showing a necrotic crust formed over the region of the treated skin. By 15 days post-treatment (FIG. 9C) the outward appearance of the skin is improving. FIG. 9D shows the same region of skin 30 days post treatment. By 60 days post-treatment (FIG. 9E), the skin has recovered and the exposed new epidermis appears nearly identical to the nearby untreated normal skin.

FIG. 10A shows a section through a control (untreated) region of the skin. FIG. 10B shows a section through the treated region of the skin one day after treatment, showing the de-nucleated epidermal cells within the region and no significant inflammation (e.g., no leukocytes or a leukocyte density comparable to that of control/untreated skin). FIG. 10C shows a section through treated skin seven days following treatment, showing the necrotic crust over the newly formed epidermal cells having healthy nuclei.

FIG. 11B show a section through a region of skin including a lesion. FIGS. 11C and 11D prophetically illustrate the removal of the lesion by treating the skin as described herein. In FIG. 11C the lesion is shown as part of the treated skin, in which the epithelial cells are regionally and specifically de-nucleated without invoking a substantial immune response and/or swelling. In FIG. 11D the lesion is separating from the skin as part of the necrotic crust, revealing newly formed epithelial cells beneath the necrotic crust that does not include the lesion.

FIGS. 12A-12H illustrate a method for treating skin (using a pulsed electrical treatment such as nano-pulse stimulation) to treat a region of the skin having a seborrheic keratosis. The skin in this example is treated using an applicator such as the one shown in FIG. 12I having a plurality of needle-like electrodes extending from a base region so that the ultra-short, high-field strength electric pulses may be delivered between the electrodes. FIG. 12A shows the region of the human skin including the seborrheic keratosis prior to treatment. FIG. 12B shows the lesion immediately following delivery of the nano-pulse stimulation (in this example, 100 pulses of ultra-short, e.g., 100 ns, high-field strength, e.g., 30 kV/cm, electric pulses were delivered over 50 seconds) in order to de-nucleate the epithelial cells in the region. FIG. 12C shows the same region of skin one hour after treatment. By 18 hours post treatment the necrotic crust has begun forming, which is also visible in FIG. 12E. One week following treatment (FIG. 12F), the necrotic lesion has fallen off (or otherwise been removed), exposing the new skin forming. FIGS. 12F and 12G show the resulting skin after two weeks and three weeks, respectively.

FIG. 13A shows the untreated skin, while FIG. 13B shows the treated skin following 90 days post treatment, showing discoloration and visible marking.

FIG. 14A shows the skin 15 days after treatment. In contrast, FIG. 14B shows the same region of skin 60 days post-treatment after removal. In contrast to the thermal method shown in FIGS. 13A and 13B, the non-thermal treatment shown in FIGS. 14A and 14B result in significantly more normal-looking skin, having less discoloration and scarring.

FIGS. 15A-15D illustrate an applicator hand piece (FIG. 15A) and exemplary electrode tips (FIGS. 15B-15D) for an apparatus for treating skin by delivering nano-pulse stimulation as described herein. The tips shown in FIGS. 15B-15D may be attached to the end of the applicator of FIG. 15A. FIGS. 15B and 15C show needle electrodes, while FIG. 15D shows an example of a non-penetrating (plate) electrode. The hand piece shown in FIG. 15A may plug into a generator.

In FIG. 16B, the graph illustrates available data from eight patients with all treatment levels of the varying settings and tips.

In FIG. 20A the applicator including the tip is shown with the electrodes (needle electrodes) arranged in a first configuration; FIG. 20B shows a front view of the device, showing the first position of the electrodes. The electrodes may be rotated by a predetermined amount, as shown in FIGS. 20C and 20D, showing side and front views, respectively. FIGS. 20E and 20F show side and front views, respectively, of the electrical applicator of FIGS. 20A-20D after the tip has been rotated 90 degrees.

FIG. 21A is another example of an applicator hand piece and exemplary electrode tips (FIGS. 21B-21C) for an apparatus for treating tissue by delivering nano-pulse stimulation and that rotates the electrodes relative to the tissue by a predetermined amount partway through the treatment, as described herein. The tips shown in FIGS. 21B-21C may be attached to the end of the applicator of FIG. 21A.

FIGS. 22A and 22B illustrate an example of an applicator having an array of needle electrodes that is configured to be activated to achieve the benefits of the rotation without actually requiring movement of the electrodes. As shown by example, a pattern of active electrodes is changed partway through a treatment from the pattern shown in FIG. 22A to the pattern shown in FIG. 22B, for example. FIGS. 22C, 22D, 22E, and 22F illustrate an example of an applicator having an array of needle electrodes configured to be stationary while achieving the benefits of rotation without actually requiring movement of the needles. As shown by example, a pattern of active electrodes is changed partway through a treatment using a mechanical switching, for example, to alternate between activating the perimeter column electrodes or the top and bottom row electrodes. FIGS. 22G, 22H, 22I, 22J, 22K, and 22L illustrate another embodiment of rotating electrodes where some electrodes remain stationary and some electrodes are moved (e.g., retracted and extended). In this example, a pulse applicator tip includes 4 stationary electrodes at the 4 corners of the applicator tip while other electrodes (e.g., 2 sets of 2 electrodes on opposite sides) are retracted and rotated 90° along with connectors (jacks) to achieve an effect of electric field rotation.

FIGS. 23A and 23B illustrate another example of an applicator having an array of needle electrodes that is configured to be activated to achieve the benefits of the rotation without actually moving the electrodes.

DETAILED DESCRIPTION

Figure 1:
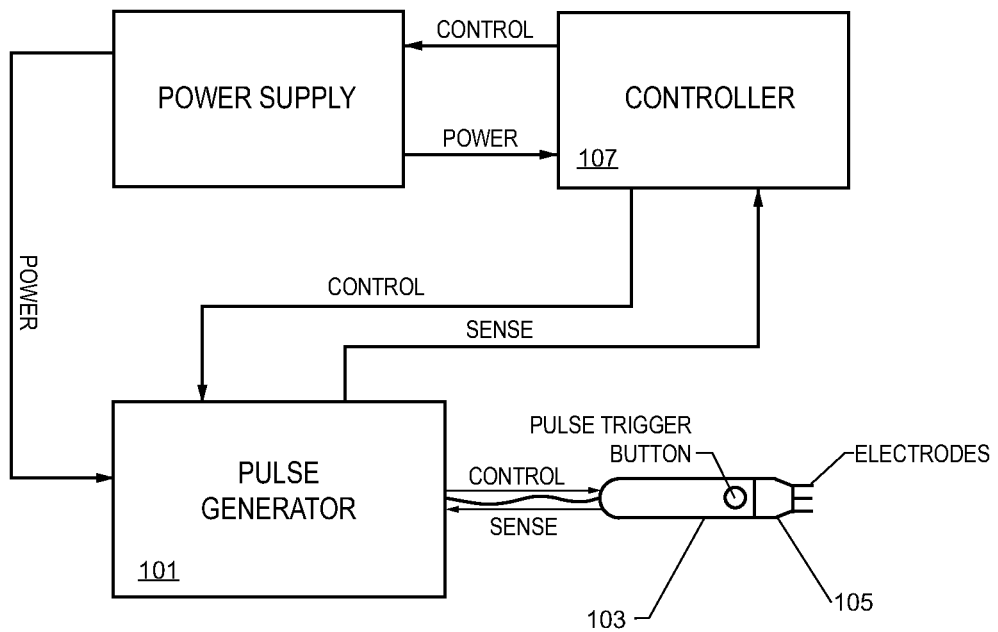
FIG. 1 is an example of a system for generation and delivering electrical nano-pulses to a skin lesion.

In general, described herein are methods and apparatuses for treating tissue (including, but not limited to skin and skin lesion, e.g., to remove or reduce the skin lesion) by applying pulsed electric treatment to a region of the tissue to make cells within the region non-viable (e.g., by destroying or degrading their nuclei and/or other internal organelles, typically without disrupting their cell membranes), without provoking a substantial inflammatory response.

The methods and apparatuses described herein may be used to treat tissue by generally applying a treatment, such as pulsed electrical treatment, to the tissue. In some implementations, these methods include performing the treatment (e.g., treatment dose) in two or more portions delivered by a plurality of electrodes arranged in a pattern and rotating the pattern of electrodes used to deliver the treatment between the different portions. Although the treatment may be performed or divided up in this manner, the treatment is still considered a single treatment (or treatment dose), as the second part of the treatment is typically applied immediately or nearly immediately (e.g., within 1 second, 10 seconds, 15 seconds, 20 seconds, 30 seconds, 1 minute, etc.) of the application of the first part of the treatment. In addition, the energy applied during the second portion is applied to the same portion of the tissue as the energy applied during the first portion.

The use of apparatuses and method in which the electrodes are rotated between different parts of the treatment are described in greater detail below, in reference to FIGS. 17-26.

Although in general, the methods and apparatuses described herein may be used to treat any tissue, many of the examples and illustrations described herein include skin tissue for convenience of description.

Skin Treatment

When applied to skin, epidermal cells may be destroyed by destroying their nucleus so that the skin forms a necrotic crust over the region of the skin and forms new epidermis below the necrotic crust so that when the necrotic crust is removed the new epidermis is exposed. Although the methods described herein are described in the context of non-thermal de-nucleating epidermal cells within the region, other methods of making the epidermal cells within the region non-viable may be used, including disrupting or destroying other organelles in the epidermal cells, such as the endoplasmic reticulum, mitochondria, etc. The non-thermal treatment may be nano-pulse stimulation (e.g., ultra-short, high-field strength electric pulses) adapted to de-nucleate epidermal cells without provoking an inflammatory response (e.g., without increasing the density of leukocytes and/or melanocytes above a threshold percentage compared to untreated skin).

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

In any of the methods described herein, the pulsed electrical treatment may be nano-pulse stimulation, which may include the application of electrical pulses with duration of 1,000 nanoseconds (ns) or less as measured, for example, at the full-width-at-half-maximum (FWHM) of the pulse wave.

A skin lesion that may be treated by the devices described herein may be any deviation of skin from a healthy or a normal condition. Examples of the skin lesions include skin diseases, conditions, injuries, defects, abnormalities or combinations of thereof. For example, such skin lesions may be malignancies (such as basal cell carcinomas, squamous cell carcinoma and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon) and combinations thereof. The skin lesion may also include aged skin, wrinkled skin or damaged skin. An example of the damaged skin is the skin damaged by sun radiation. In one embodiment, the skin lesions may be basal cell carcinoma (including papilloma), squamous cell carcinoma, actinic keratosis, warts, or combinations thereof. In one embodiment, the skin lesion may be a skin lesion of a human. In this embodiment, the skin lesion may comprise basal cell carcinoma, squamous cell carcinoma, actinic keratosis, warts, or combinations thereof In this embodiment, the skin lesion may also comprise common warts, actinic keratosis, or combinations thereof. The skin lesion may be a common wart of a human. The skin lesion may also be an actinic keratosis of a human.

The pulsed electrical treatment, such as a nano-pulse stimulation treatment, may be achieved by providing electrical energy to the skin lesion in a form of one or more electrical pulses. During this treatment, tissue removal may not be intentional and, if it happens, may not be substantial. Thus, the treatment may thereby be advantageous over current or other proposed treatment techniques since it may achieve its purpose with no substantial tissue removal. Further, these methods may be generally non-thermal, and may be configured to prevent substantial inflammatory response.

The treatment of the skin lesion may prevent growth of the lesion. The treatment may reduce the volume of the skin lesion. That is, the treatment induces at least shrinkage of the lesion. This shrinkage may be at least 10%, 20%, 30%, 60%, 70%, 80%, 90%, or more than 90%. The treatment may reduce the skin lesion volume to a negligible level (i.e., clearance of the lesion). The lesion growth prevention or the lesion volume reduction may be achieved in at least 10%, 20%, 30%, 40%, 50%, 60%, 70%, 80%, 90%, or more than 90% of cases.

When the lesion volume shrinks to a negligible size (i.e. about 100%), the lesion is "cleared". If the lesion growth or shrinkage is less than 10% after the treatment, the lesion growth is considered to have been "prevented" or that there is "no change". If the lesion shrinkage is in the range of >10% and <50%, it is concluded that there is lesion "shrinkage". If the lesion shrinkage is in the range of >50% and <100%, it is concluded that there is "substantial shrinkage". If the lesion growth is in the range of >10% to <100%, it is concluded that there is lesion "growth". And if the lesion growth is >100%, it is concluded that there is "substantial growth".

If the height (i.e. protrusion) of the lesion above the skin surface is negligibly small, i.e. about 0.00 mm, the lesion height is recorded as about 0.10 mm.

The treatment results may be permanent or temporary. In one embodiment, the growth prevention, or the shrinkage or the clearance may last for a duration of at least 7 days, at least 10 days, at least 20 days, at least 30 days, at least 40 days, at least 50 days, at least 60 days, at least 70 days, at least 80 days, at least 90 days, at least 100 days, or at least 110 days.

The treatment may comprise at least one treatment session. For example, the treatment session may comprise an administration of the electrical energy to the skin lesion of a human by physician at an office visit. The treatment of a human lesion may also comprise a plurality of treatments sessions. For example, it may comprise at least two treatment sessions or at least three treatment sessions. These treatments may be combined with any other treatment to increase efficacy of the lesion treatment. These other treatments may include over-the-counter treatments, treatments with prescription medicines, surgery, and destructive procedures. For example, these other lesion treatments may include curettage, electrodessication, cryotherapy, topical therapy, and combinations thereof.

When the pulsed electrical treatment is nano-pulse stimulation, any system suitable for delivery of electrical nano-pulses with a duration of 1,000 ns or less to the skin lesion may be used. The system may comprise a power supply, a controller, a pulse generator, and a pulse delivery device (e.g., a wand). An example of this system is schematically shown in FIG. 1.

The pulse generator 101 may be any pulse generator that is capable of generating pulses with a duration of 1,000 ns or less at FWHM. The pulse delivery device may be any device that can deliver electrical pulses to the skin lesion. This device may have an applicator tip that may comprise at least one delivery electrode. This applicator may further comprise at least one ground electrode. The delivery electrode and/or the ground electrode may penetrate into the skin lesion to deliver the electrical pulses. The delivery electrode and/or the ground electrode may deliver the electrical pulses without substantially or intentionally penetrating into the skin lesion. For example, the skin lesion may be constricted between the electrodes or the electrodes may only touch the lesion (or the region surrounding the lesion) during the delivery of the electrical pulses.

A system for treating tissue (e.g., skin) as described herein may include an applicator 103 having a treatment tip 105 with two or more (e.g., a plurality) of electrodes. The system may generally include a controller 107. The controller may control operation of the system, and may include one or more processors, one or more memories, and the like. The controller may include logic (e.g., hardware, software, firmware) including instructions that, when executed by the one or more processor(s), may control the system to apply the electrical therapy as described herein. For example, the set of instructions may operate a robotic actuator (e.g., robotic arm) to move the treatment electrodes to the target tissue region and control the application of pulsed electrical energy treatment to the tissue. The set of instructions may include instructions controlling the application of the pulses, rotation of the pattern of electrodes applying the energy and/or placement of the applicator on/off of the tissue.

For example, in some variations, the system may include a means for controlling the applicator and a means for applying the pulsed electrical energy. The system may also include a means for applying energy to denucleate cells within the target treatment tissue (e.g., skin). Any of these systems may also include a means for rotating the pattern of electrodes partway through the treatment.

Figure 4:
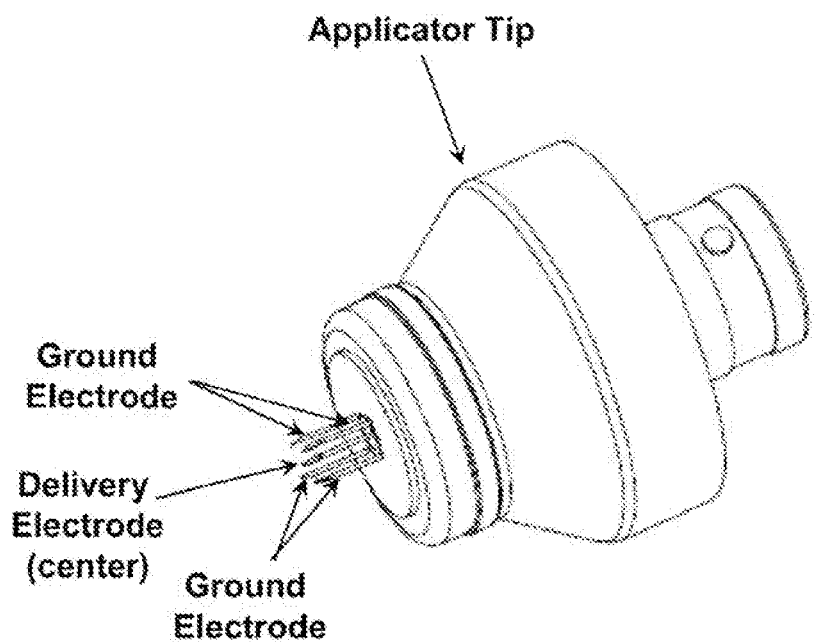
FIG. 4 is an example of an applicator tip with one delivery electrode and four ground electrodes.

An example of an applicator tip is illustrated in FIG. 4. In this example, the applicator tip has one delivery electrode placed at the center and four ground electrodes surrounding the delivery electrode. The base of the electrodes may be embedded in a solid insulating material to maintain separations between them.

The electrical energy may be applied to the skin lesion in the form of at least one electrical pulse. For example, between 30 and 150 pulses may be applied (e.g., between 33 and 100). In one embodiment, at least 10 pulses, at least 100 pulses or at least 2000 pulses (e.g., at least 1,000) pulses may be applied to treat the lesion during a single treatment. The duration of one or more of the pulses may be in the range of 0.01 ns to 1,000 ns. For example, the pulse width may be between 100 and 500 ns (e.g., between 200 and 300 ns). The duration of one or more of the pulses may be, for example, in sub-microsecond range, or in the range of 1 ns to 600 ns, or in the range of 1 ns to 300 ns.

The total electrical energy applied per volume of skin lesion may be at least 10 mJ/mm$^3$, at least 20 mJ/mm$^3$, at least 100 mJ/mm$^3$, at least 500 mJ/mm$^3$, or at least 1,000 mJ/mm$^3$. In another embodiment, the total applied electrical energy per volume of the skin lesion may be in the range of 10 mJ/mm$^3$ to 10,000 mJ/mm$^3$.

The electrical field produced by each pulse may be at least 1 kV/cm at the peak amplitude of the pulse. For example, the electrical field may be between 10 and 50 kV/cm (e.g., between 20 to 30 kV/cm). The electrical field produced by each pulse may also be at least 10 kV/cm at the peak amplitude of the pulse. In another embodiment, the electrical field produced by each pulse may be in the range of 1 kV/cm to 1,000 kV/cm at the peak amplitude of the pulse. Yet, in another embodiment, the electrical field produced by each pulse may be in the range of 10 kV/cm to 100 kV/cm at the peak amplitude of the pulse.

The treatment may comprise at least one treatment session, i.e. administration of the electrical energy to the skin lesion by physician at an office visit. This treatment session may comprise at least one application of the electric energy to a lesion. The electrical energy may be delivered to the skin lesion in any manner suitable for the skin lesion. For example, the electrical energy may be delivered after contacting the surface of the lesion by electrodes of the applicator tip. In this example, the electrodes don't penetrate into the lesion during the application of the electrical energy. In another example, the electric energy may also be delivered after insertion of the electrodes to the skin lesion. For example, one application may comprise first penetration of the skin lesion by the electrodes of the applicator tip and then delivery of a desirable number of pulses, for example, about 100 pulses, with a pulse duration of between about 200 to 300 ns. More than one application may be used per treatment session to treat the lesion. The number of applications may depend on the size and/or the type of the lesion. Larger lesions may require more than one application per treatment session, as discussed in detail below. Also, different types of lesions may require higher energies, and therefore more applications per treatment session may be needed to at least prevent the growth of the lesions. The treatment of a lesion may also comprise a plurality of treatment sessions. For example, it may comprise at least two treatment sessions or at least three treatment sessions. These treatment sessions may also be separated in time by 1 or more days (e.g., 2 days, 3 days, 4 days, 5 days, 6 days, 7 days, etc.).

Figure 2:
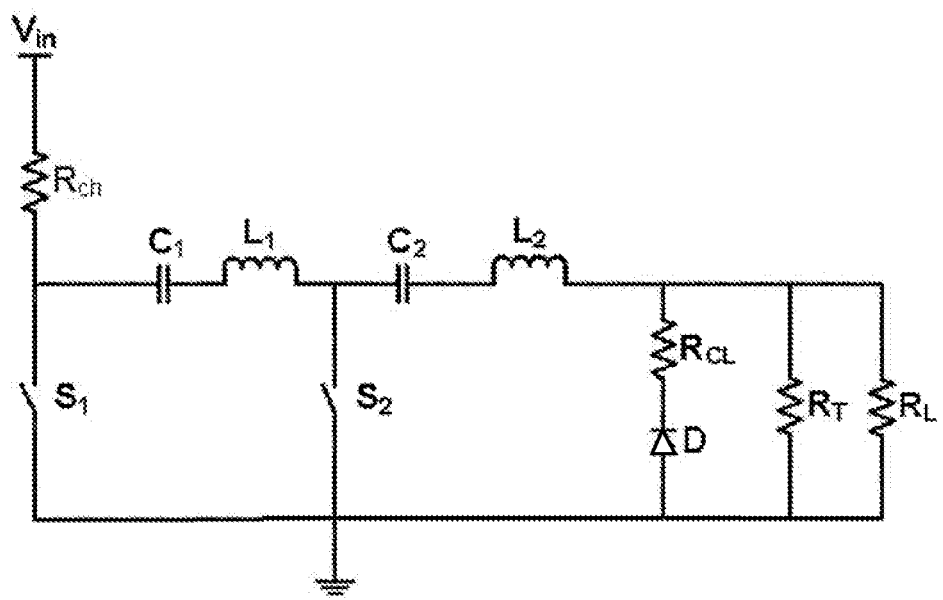
FIG. 2 is an example of a simplified diode pulse generator.

An electrical pulse generation and delivery system is schematically shown in FIG. 1 and includes a pulse generator 101. An example of the pulse generator is schematically shown in FIG. 2. As shown in FIG. 2, the diode pulse generator may include a tank circuit consisting of inductances L1 and L2 and capacitances C1 and C2. The tank circuit may be connected in series with a diode D across which a load RL to be driven may be connected. This load may be the resistance of the lesion or tissue. The pulse generator may include a switching system, such as switches S1 and S2, which may be electronic. A voltage supply $V_{in}$ may be connected to the diode pulse generator through a resistance $R_ch$. Other examples of pulse generators and systems that may be used with any of the methods of the present disclosure and/or may be modified to form any of the apparatuses described herein are shown and described in co-pending U.S. patent application Ser. Nos. 15/148,344, 15/269,273, 15/595,684, 15/347,729, 15/444,738, and 15/347,728; each of these patent application is herein incorporated by reference in its entirety.

Before the beginning of a pulse cycle, the switch S1 may be open and the switch S2 may be closed. This may cause the capacitance C1 to fully charge and the capacitance C2 to fully discharge. At the beginning of the pulse cycle, the switch S1 may be closed and the switch S2 may be opened. This may cause charge to transfer from the capacitance C1 to the capacitance C2. During this transfer, the current through the tank circuit may rise and fall in approximately a sinusoidal manner.

This current may cause the diode D to be forward-biased as it travels through it. During this process, charge may be stored in the depletion layer of the diode D. At the end of the half-cycle, switch S2 may be closed. During the next half-cycle, the current flow may reverse in direction, causing the diode D to be reverse-biased. During the first part of the second half-cycle, current may still flow through the diode D while charge in its depletion layer is being depleted. Once the charge is depleted, the current through the diode D stops, causing the diode to appear as an open switch. This may cause the current through the inductance L2 to commute from the diode D to the load RL. The diode D may thus be configured to act as an opening switch, interrupting the current in the inductance L2 and commuting it into the load RL. Current may now travel through the load RL until the energy stored in the tank circuit consisting of the capacitance C2 and the inductance L2 depletes, thus delivering a pulse into the load RL.

Figure 3:
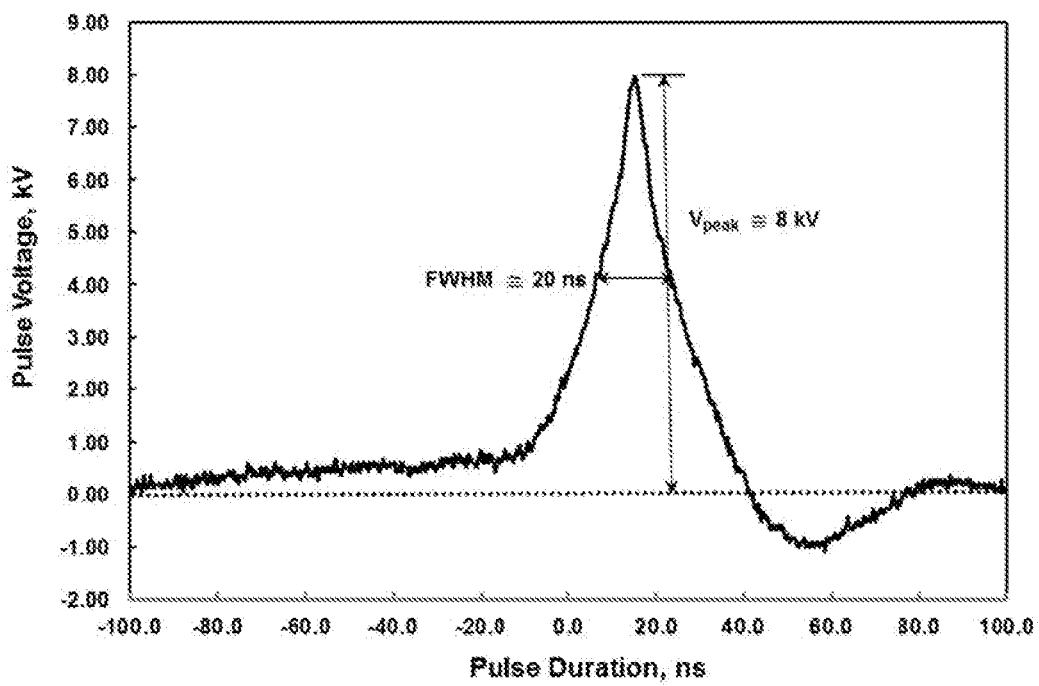
FIG. 3 is an example of an electrical pulse generated by the system, such as that shown in FIG. 1.

This pulse generator included a current limiting resistor, RCL configured to limit damage to the pulse generator. The value of this resistor was about 1 ohm. The pulse generator further included a terminating resistance, RT in parallel with the diode, wherein the terminating resistance was configured to protect the output stage of the pulse generator. The value of this resistor was about 100 ohms. The pulse generator disclosed above may provide at least one electrical pulse with a duration varying in the range of about 7 nanoseconds (ns) at FWHM to about 20 ns at FWHM. In one example, a pulse with duration of about 20 ns at FWHM was generated. The characteristics of this pulse were recorded. As shown in FIG. 3, this pulse had pulse duration of about 20 ns at FWHM and a peak amplitude of about 8.00 kV.

The electrical nano-pulses were delivered to a lesion by using applicator tips comprising one delivery electrode and four ground electrodes surrounding the delivery electrode. This applicator tip is shown in FIG. 4. Each electrode was constructed by using a 30 gauge needle (i.e. about 0.255 mm in diameter). The delivery and the ground electrodes have the same length for each applicator tip. This length varied in the range of about 2 millimeters (mm) to 5 mm. The electrodes were placed to form a square pattern. The ground electrodes were at the corners of this square and the delivery electrode was at its center. Center-to-center distance between the delivery electrode and each ground electrode was about 1.75 mm. This configuration provided a volume of about 30.625 cubic-millimeters (mm 3) within the boundary formed by the ground electrodes. The ground electrodes and the delivery electrode were electrically isolated from each other by embedding them in a Teflon insulation (not shown in FIG. 4).

The tip configuration may be different than illustrated. There may be other applicator tip configurations suitable for the treatment of the lesions. These configurations may include tips comprising at least one delivery electrode and at least one ground electrode. For example, as the system disclosed above is coaxial in nature, with the ground electrodes surrounding the delivery electrode, any number of needle configurations may be realized, including a circular arrangement with five or more ground electrodes, a triangular arrangement with three ground electrodes, wherein the delivery electrode may be placed at the geometrical center of such arrangements. A simple linear arrangement with just two opposing electrodes, i.e., one return electrode and one delivery electrode, may also be used for the delivery of the electrical pulses.

Still other tip configurations, for example those with different electrode spacing or length, may also be used for the treatment of the lesions. However, as the effect of these short pulses on cells is largely dependent upon the strength of electric field, an increase in return and active electrode spacing may have to be accompanied by a proportional increase in output voltage to maintain the required field for the effect on cells. Similarly, if the spacing is reduced, the voltage could be proportionally decreased.

Each pulse with a duration of about 7 ns at FWHM in this example may include a carrier frequency. For example, a pulse may contain significant frequency components centered at about 142.9 megahertz (MHz), and each pulse with a duration of about 14 ns at FHWM contained significant frequency components centered at about 71.4 MHz. Electrical nano-pulses with different amplitudes (e.g., peak amplitude of about 7.0 kilovolts (kV), peak amplitude of about 5.5 kV, etc.) may be used. In one example, the electrical field is about 40 kilovolts/centimeter (kV/cm) at the peak amplitude of about 7.0 kV and about 31 kV/cm at the peak amplitude of about 5.5 kV.

Values of the pulse durations and the peak amplitudes referred to herein may be average values unless specifically noted. These pulse durations and the peak amplitudes may vary with a standard deviation of 10% of their average values. For example, the pulse duration of about 7 ns at FWHM may be an average of pulse durations that vary within the range of 6.30 ns and 7.70 ns, or it is 7.00±0.70 ns. Similarly, the peak amplitude of about 7.00 kV may be an average of the peak amplitudes that vary within the range of 6.30 kV and 7.70 KV, or it is 7.00±0.70 kV. The lesion resistance may be expected to be about 100 ohms. In general, the skin impedance values may be related to the design of the electrode being used. For example, see the electrodes shown in FIGS. 15A-15D and described in detail below. Different electrode designs may register different tissue impedances, e.g., between about 100 Ohms and 1 KOhm (e.g., from 150 Ohms to 800 Ohms), depending on the quality of the electrode contact, which may be (in part) a function of the electrode design.

Figure 5:
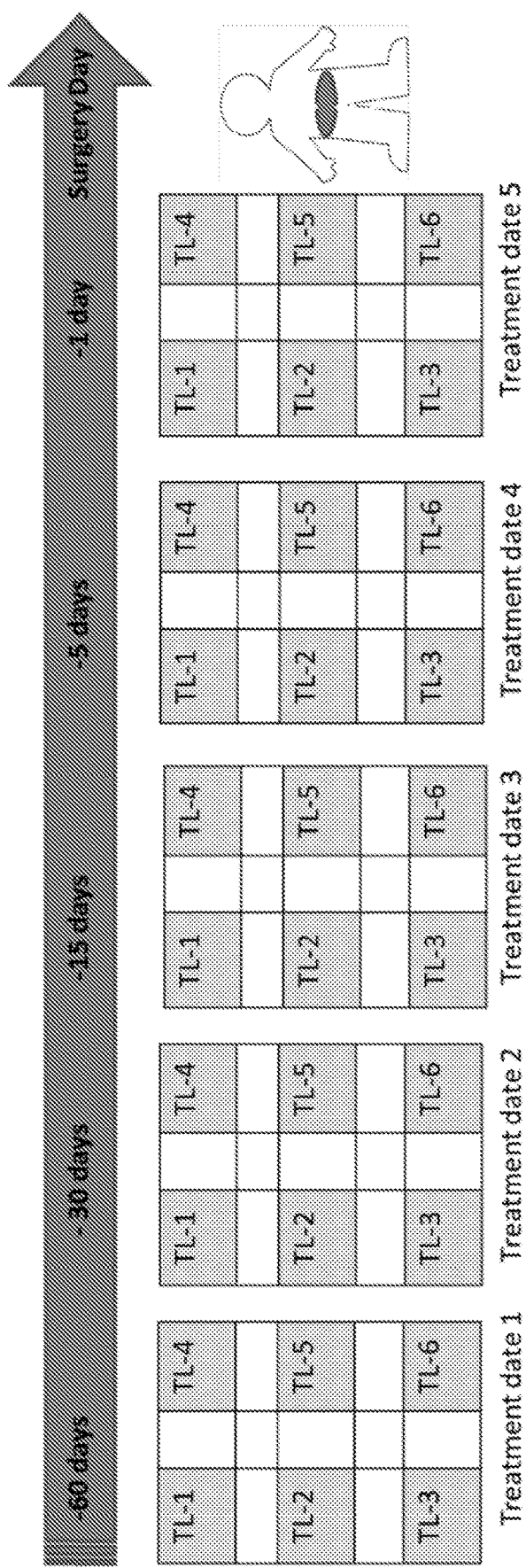
FIG. 5 is an example of a protocol illustrating the use the methods described herein to treat the skin of a patient. This study was used to illustrate dose ranging over a 60 day time course.

An abdominoplasty study was done on human subjects to evaluate six treatment levels (TLs, low to high) on human skin using different treatment applicators (treatment tips), including 5 mm×5 mm and 2.5 mm×2.5 mm tips (similar to those shown in FIGS. 15B and 15C). Abdominal skin was treated in five patients at 1, 5, 25, 30 and 60 days before the tissue was removed, and histological examination of the treated (and nearby control) sites was performed. FIG. 5 illustrates the pattern of stimulation applied to the abdominal skin during the trial on each patient. Treatment date 1 was performed 60 days before removal and analysis of the skin tissue. For each treatment date a 3×2 grid of treated tissue was treated, and each treatment site was treated with a different treatment level (TL1, TL2, TL3, TL4, TL5 and TL6, in increasing levels). This protocol provided a time course of healing of each of the six treatment levels from 1 to 60 days after exposure. 8 mm diameter discs of tissue including each treatment site was then biopsied and examined. These treatment levels were ranked from decreasing to increasing intensity levels. The treatment levels each had an electric field strength between 20 to 30 kV/cm, a pulse width between 200 to 300 ns, a frequency between 2 to 6 Hz, and between 33 to 100 pulses. Generally, the energy per pulse, as well as the total energy applied by the electrodes, for each treatment level increased from TL1 to TL6.

Based on the preliminary results from this work, treatment levels in which the skin was stimulated sufficiently so that dermal cells within the epidermal region being treated were de-nucleated and for which little or no inflammatory response was seen resulted in the formation of a necrotic crust over a region of new epidermis which, by 60 days, formed new skin with very little, if any, discoloration and/or scarring.

As part of the analysis of this study, various tissue staining techniques intended to identify specific cellular changes and tissue morphology were utilized in the histologic analysis to characterize the initial tissue responses and the subsequent recovery processes, and sequential findings for each of the six energy levels were compared to normal control punch biopsies in the same patient. This study found that the method of using low energy nano-pulse cellular stimulation on skin as described herein lead to a loss of viability of the epidermal layer of skin (at all energy levels examined for treatment) by at least the first day post-treatment. There was a lack of observed effect on dermal collagen, and little, if any inflammation given the amount of epidermal damage. This lack of inflammatory effect is consistent with preservation of fibroblasts, elastin, and melanocyte recovery. The transient effect on deeper cellular structures in the dermis suggest a surprising affinity for highly cellular tissue, and a sparing effect on the less cellular connective tissue of the collagen layer.

Figure 16A:
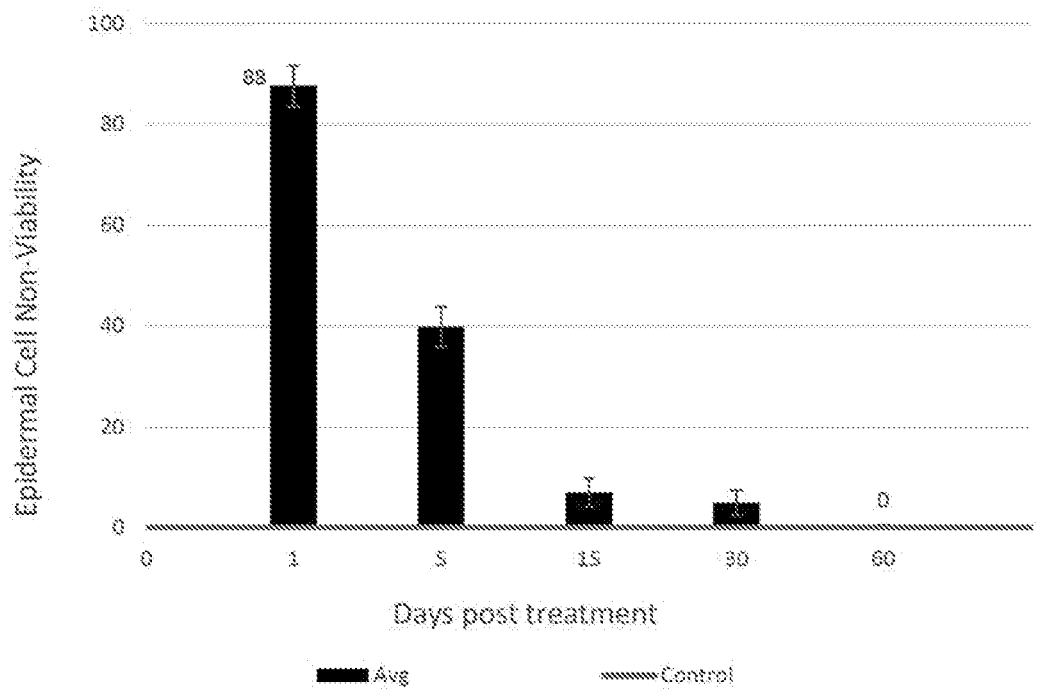
FIG. 16A is a graph illustrating the average epidermal cell non-viability across all energy treatment levels applied. Error bars indicate the standard error of the mean. The graph illustrates available data from eight patients with all treatment levels of the varying settings and tips as described herein.

FIG. 16A summarizes the effect of the stimulation across all of the energy levels tested above on epidermal cells. A review of the changes of the entire thickness of the epidermal/dermal layer and subcutaneous fat from day 1 through day 60 was performed. The primary changes due to the non-thermal energy exposure were observed in the treated skin within the epidermal layer of skin. At day one post-treatment, tissue samples from all subjects showed evidence of ghost cells in the epidermal layer characterized by intact cell membranes and absence of nuclei within those cells, which indicates a non-viability of those cells. The non-viability of epidermal cells was full-thickness and complete for all energy settings by 1 day post-treatment. In many patients, hair follicles and eccrine glands within the dermal layer of the skin were also visible for histologic review. In specimens in which hair follicles and eccrine ducts were visible, there was a partial (50%) to full necrosis of the upper portions of the hair follicles and eccrine ducts. Five (5) days post-treatment epidermal changes range from 50% to 90% healing (50%-10% non-viable epidermal cells), with the exception of 3 patients of the highest treatment energy. Hair follicles and eccrine ducts when visible in the tissue samples showed focal dyskeratotic cells within the hair follicles at 5 and 15 days consistent with partial healing at 5 days and complete recovery by 15 days. Eccrine ducts often showed focal squamous metaplasia, a sign of re-epithelialization. By 15 days post-treatment, the epidermis layer had returned to normal in almost all cases. By 60 days, the epidermis, hair follicles, and eccrine glands had all completely returned to normal. In two patients treated at the highest energy level, epidermal necrosis was followed by a formation of an inflammatory eschar. This formation healed by 60 days with some epidermal flattening and minimal papillary dermal fibrosis.

FIG. 16A shows a quantitative analysis performed on the epidermal layer of the skin based on a scale rating of the epidermal integrity. Different energy treatment levels were applied to the targeted normal abdominal tissue among the 8 patients treated. FIG. 16A shows the non-viability of the cells across all different treatment energy levels over the time period of 1 day to 60 days post treatment (post application of nano-pulse stimulation. A score of 100% indicates completely non-viable epidermis, a score of 10% indicates recovered epidermis with evidence of "flatness", and a score, and score of 0% indicates completely viable epidermal cells (complete epidermal recovery). Almost all energy levels showed complete non-viability of epidermal cells by 1 day post-treatment with an average of 88% completely non-viable cells. By 60 days the epidermis, hair follicles, and eccrine glands had all completely returned to normal, with the exception of 1 patient at the highest treatment level.

Minimal alterations in the dermal collagen were observed, with no evidence of thermal injury apparent. In several tissue samples exposed to the highest treatment levels, there was focal papillary dermal necrosis evident. This effect was observed at the 1 day and 5 day intervals but was not observed at the 15-60 day intervals. In two patients treated at the highest energy level, there was some parallel fibrosis of the dermal collagen bundles at 60 days.

Figure 16B:
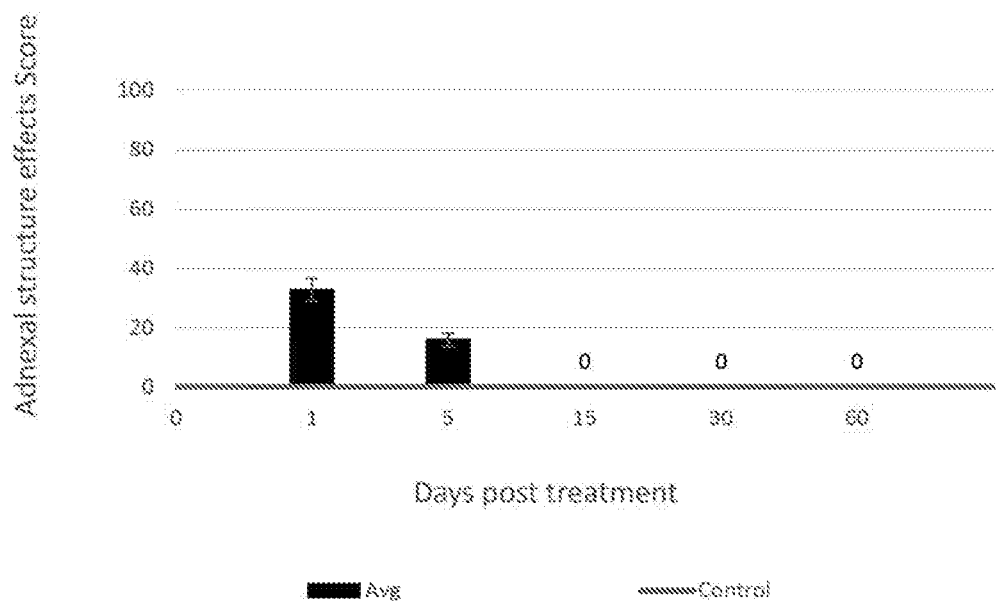
FIG. 16B shows the average adnexal (e.g., dermis) structure effects of different treatment levels applied. Error bars indicate the standard error of the mean.

FIG. 16B shows a quantitative analysis on the adnexal structure effects based on a scale rating. A score of 0% indicates there is no effect on adnexal structures, a score of 50% indicates that about half of observed adnexal cells are pink and glassy, and a score of 100% indicates necrosis of hair follicle. An average score of 33% and 16% was shown across all treatment levels applied for day 1 and day 5 respectively with no adnexal structure effect seen past day 15 for any energy level.

Elastic tissue remained intact in the vast majority of patients. In the higher treatment levels there was occasional slight decrease in elastic fiber at days 1, 5 and 15, with return of elastic fibers observed by days 30 and 60. Taken in summary with the results of the trichrome collagen stains, these findings indicate relative minimal effects on the dermis. This predicts a very low risk of scarring.

Figure 16C:
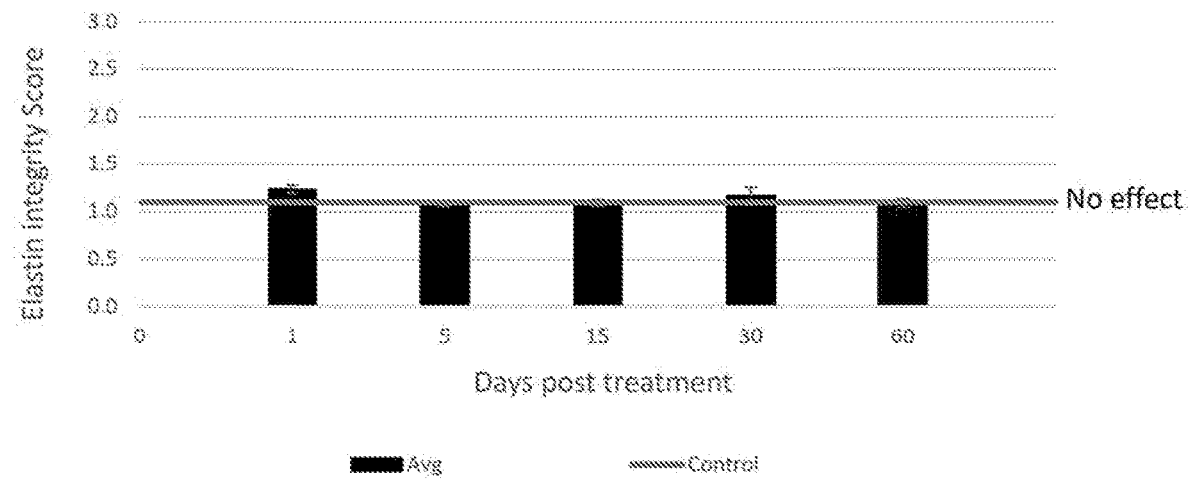
FIG. 16C illustrates the lack of effect on the average elastin integrity of all of the treatment levels examined. Error bars indicate the standard error of the mean.

A quantitative analysis was performed on the elastic integrity based on a scale rating shown in FIG. 16C. A score of 1 value indicates there is no effect on elastin fibers, a score of 2 indicates a mild effect on elastin fibers and loss of elastic fibers in papillary dermis, and a value of 3 indicates a moderate effect on elastin fibers and loss of fibers in reticular dermis. As seen in FIG. 16C there is no apparent effect on the elastin integrity at any time following treatment.

Figure 16D:
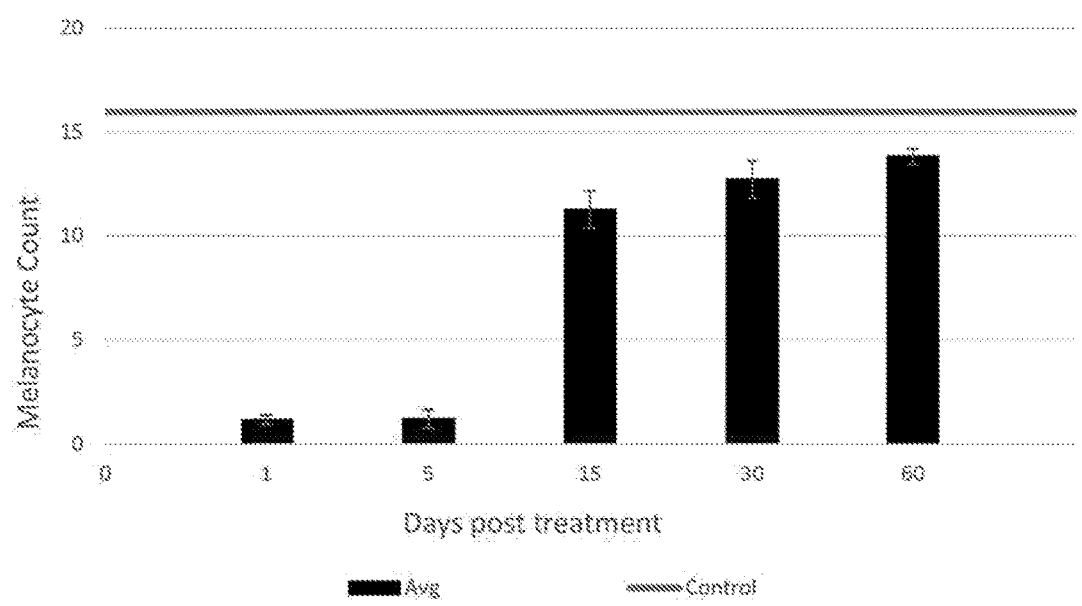
FIG. 16D illustrates average melanocyte count following nanosecond electrical puling as described herein across different treatment levels. Error bars indicate the standard error of the mean.

The number of melanocytes was observed using a MITF immunostain. Staining for melanocytes showed a marked loss of melanocytes in the treatment areas at day one, however by day 15 the number of melanocytes returned to normal density, comparable to the control specimens. This was observed through 60 days. The rapid return of the melanocytic density to levels comparable to control should be consistent with a relative normalization of skin pigmentation over time. The number of melanocytes was quantified throughout the time periods and depicted in FIG. 16D.

The number of dermal fibroblasts appeared to decrease at day 1 and day 5 following treatment. However, by day 15, 30 and 60 the number of dermal fibroblasts was equivalent to pretreatment samples. This suggests a temporary decrease in the number of dermal fibroblasts after treatment and possibly some loss of dermal fibroblasts secondary to the treatment. However, fibroblasts are recruited from normal surrounding skin and peripheral circulation and the population of fibroblasts returned to levels similar to the control in the 15-60 day time period. This finding suggests a recovery of fibroblasts and the associated normal capacity to rebuild connective tissue.

Epidermal staining was performed using immunohistochemical stains to active Caspase 3. This analysis shows no significant expression within the epidermis in the 1 and 5 day post-treatment time frames tested. These findings do not provide clear evidence of apoptotic cell death during the analyzed time frames. Therefore, the precise mechanism for the observation of ghost cells and associated cell death by 24 hours post-treatment was not identifiable by this method.

Most interestingly, the degree of dermal inflammation was minimal compared to other thermal or physical methods of intentionally damaging surface epidermal tissue. There was a small amount of inflammation seen at day 1 and day 5, however the amount of inflammation appears to be sparse and perivascular. Of note, there were several samples which showed focal perivascular inflammation with fibrin deposition suggestive of low grade vascular damage. This can be seen at day 5 through day 60 and appeared to have no clinical correlation to degree of epidermal necrosis or impact on healing.

Figure 16E:
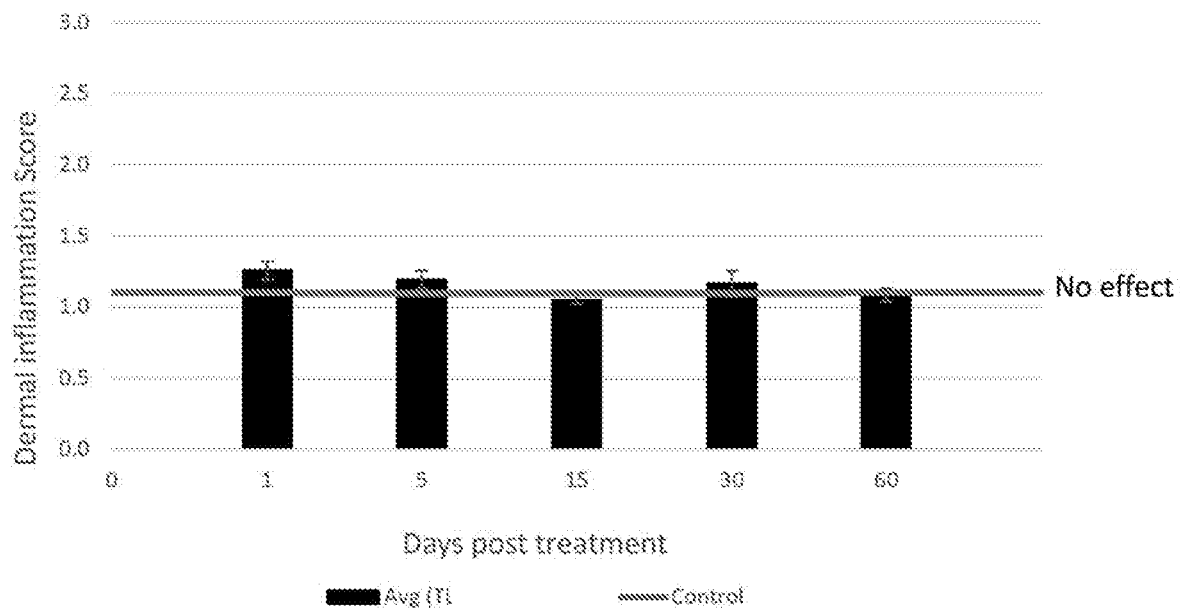
FIG. 16E is a graph showing the average dermal inflammation score at various post-treatment times, across all treatment levels examined. Error bars indicate the standard error of the mean.

A quantitative analysis was performed on the average dermal inflammation scores based on a scale rating shown in FIG. 16E. A score of 3 indicates evidence of fiberplasia and likely long term scar. A score of 2 indicates evidence of fibroplasia and unlikely long-term scar and a score of 1 indicates no evidence of fibroplasia.

In summary, the methods of using low energy nano-pulse cellular stimulation on skin as described herein led to a loss of the epidermal layer of skin by at least one day post-treatment (likely faster). These methods did not affect dermal collagen and resulted in a relatively low level of inflammation given the amount of epidermal damage. This lack of inflammatory effect is consistent with preservation of fibroblasts, elastin, and/or melanocyte recovery.

Figure 6A:
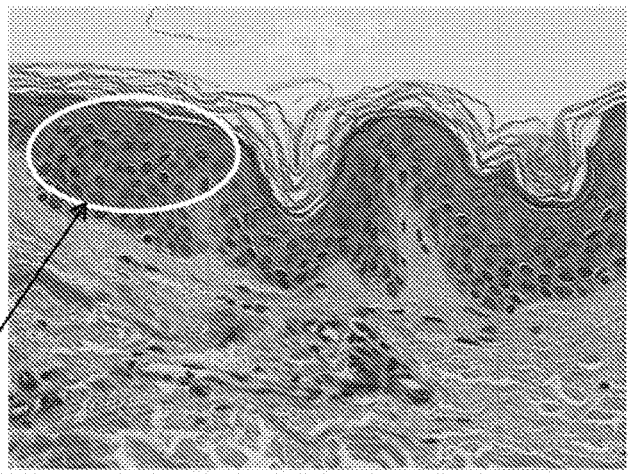
FIG. 6A is an example of untreated (control) skin showing epidermal cells stained to show nuclei.
Figure 6B:
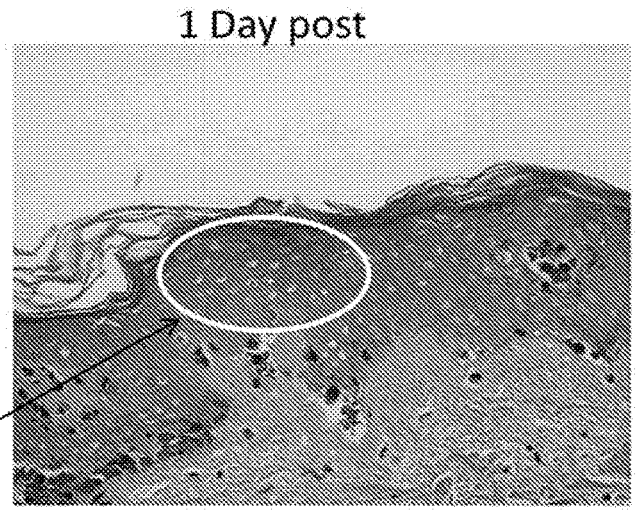
FIG. 6B is a histological example of rapid de-nucleation with minimal inflammation in the treated tissue.
Figure 6C:
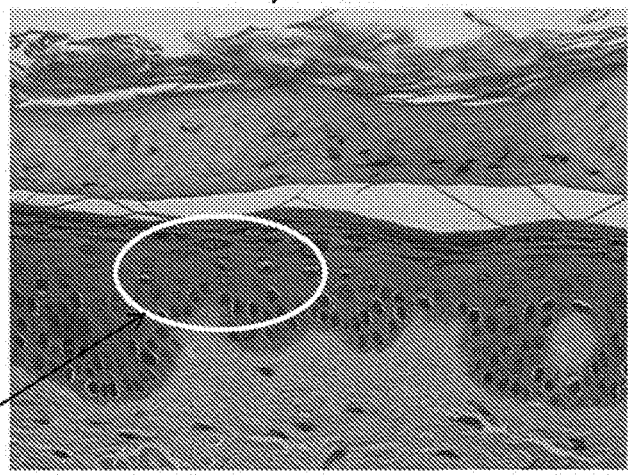
FIG. 6C shows treated skin seven days after treatment; the original epidermis, including the de-nucleated cells, has formed a necrotic crust that is peeling off of the newly formed epidermis.

For example, FIGS. 6A-6C illustrate histological sections of skin treated with an intermediate treatment level (TL4), showing rapid epidermal layer destruction by de-nucleation with minimal inflammation (e.g., a rise of than about 15% in acute inflammatory markers in the treated tissue) and rapid re-epithelization. For example, FIG. 6A shows a histological section through a control region of skin adjacent to the treated regions; the skin has been stained with a nuclear stain and shows dark nuclei in untreated epithelial cells.

FIG. 6B is a stained section though a region treated (TL4) one day prior to fixation and staining. In FIG. 6B the epithelial cells have lost their nuclei, becoming "ghost cells" in which the cell membrane appears intact, but the cells 603 are non-viable as their nucleus has been selectively destroyed by the treatment. It can be seen from the representative image in FIG. 6B that there are no cellular indicators of inflammation (e.g., leukocyte density is unchanged, compared to control regions). FIG. 6C shows an example of a tissue region seven days post treatment. By a few days following treatment at this moderate treatment level (TL4), the de-nucleated cell has formed a necrotic crust 605 and by day 7 post-treatment, have begun to peel away from the underlying region 609 in which new epidermal cells 607 have formed, showing healthy nuclei and little, if any, inflammation.

Figure 7A:
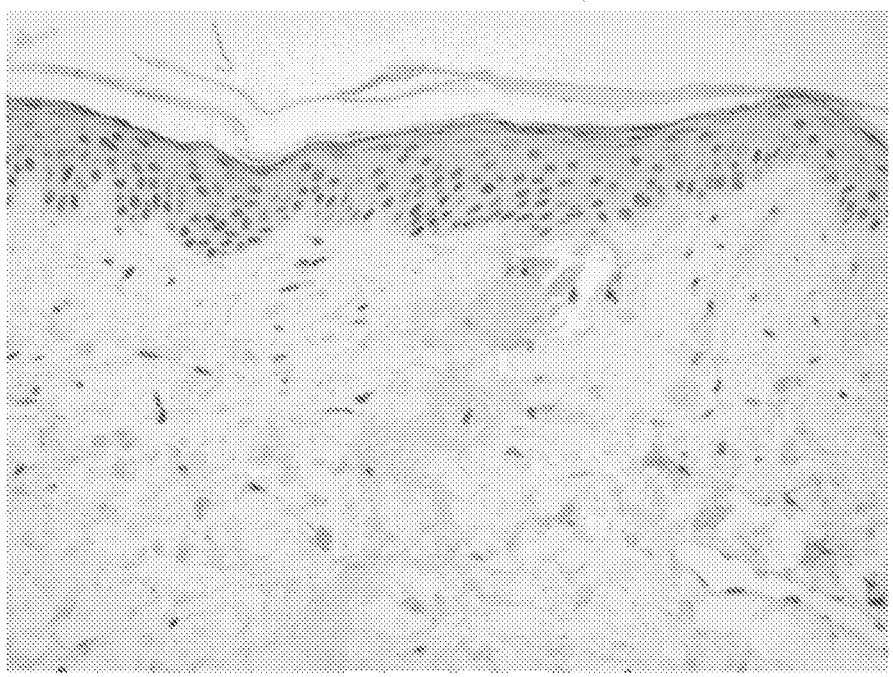
FIGS. 7A-7B illustrate the rapid recovery of melanocytes in the newly formed epidermis in treated skin.
Figure 7B:
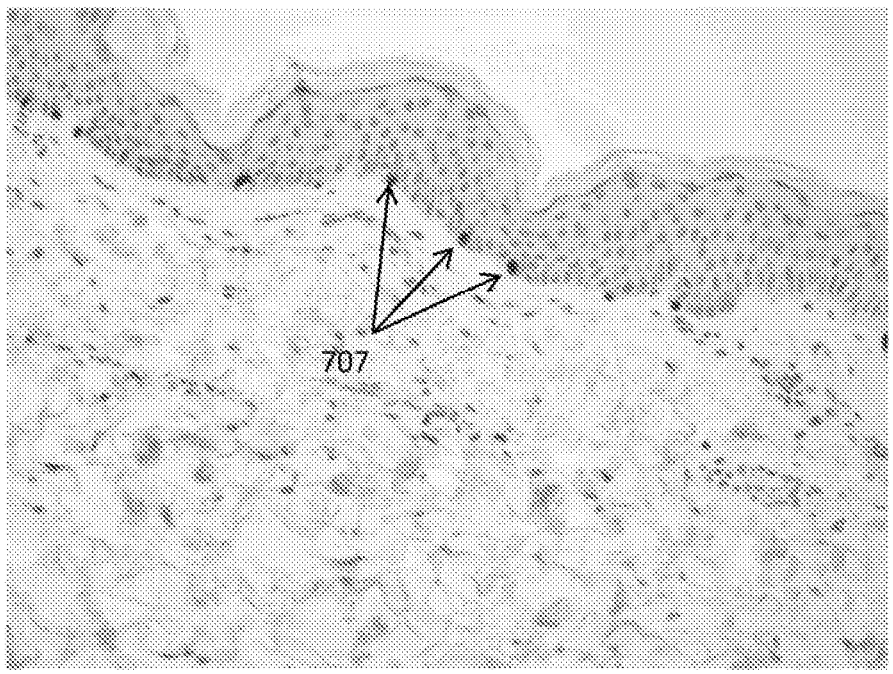

Any of the methods and apparatuses described herein may also be configured to provide for new epidermis having less scarring and discoloration by de-nucleating epidermal cells in a treatment zone without invoking an inflammatory response (unlike in thermal treatments) so that melanocytes and extracellular matrix are distributed in a manner that resembles or replicates nearby 'normal' untreated skin. For example, FIGS. 7A and 7B illustrate the recovery of melanocytes following a treatment similar to that shown in FIGS. 6B-6C. In FIG. 7A a treated region of skin is shown 15 days following treatment with a high to moderate (TL5) treatment level. As shown in FIG. 7A, shortly after treatment (e.g., by 15 days post treatment) there is initially an absence of melanocytes. FIG. 7B histologically shows that in the treated skin sixty (60) days following treatment there is an average distribution of melanocytes, similar to control skin. In FIG. 7B, the image shows nine distinct melanocytes 707, a similar density and distribution to what is shown by nearby control (untreated, lesion-free) tissue. Rapid recovery of melanocytes is highly predictive of normal melanin production and full recovery of skin tone; injuries with a high amount of inflammation typically create a higher risk of long-term melanocyte suppression.

Figure 8A:
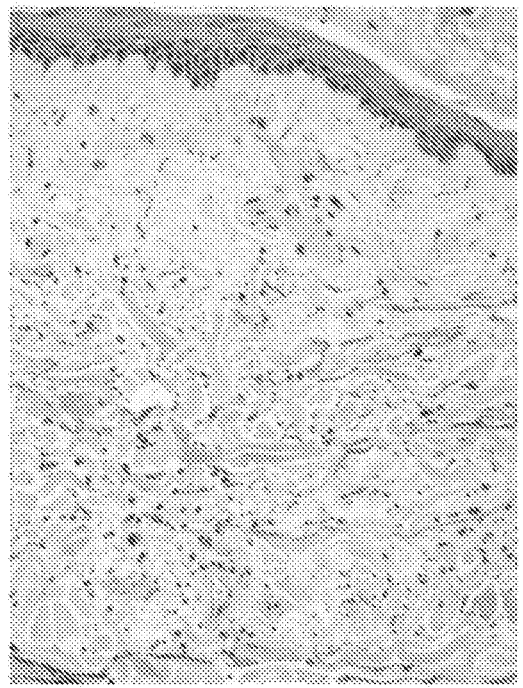
FIGS. 8A and 8B show the restoration of elastin distribution and orientation following treatment.
Figure 8B:
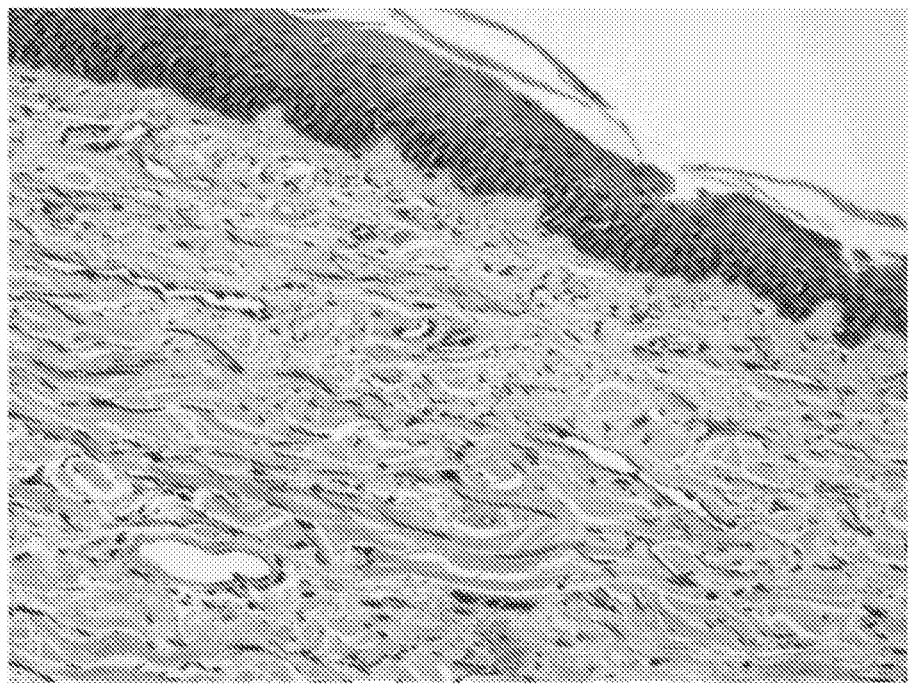

FIGS. 8A and 8B illustrate the effect of treatment as described herein on the distribution and density of elastin near the surface of the newly formed epidermal tissue. Typically, restoring the elastin to normal results in a reduction in scarring risk. In FIG. 8A, following a high treatment level (TL6), after 15 days from treatment, the treated skin shows some change in elastin near the surface of the tissue. However, by sixty days post-treatment, as shown in FIG. 8B, the elastin has been restored to a nearly normal orientation and density.

The overall appearance of the skin when treated to de-nucleate the epithelial cells, e.g., using a moderate level (TL4) of nano-pulse stimulation is illustrated in FIG. 9A-9E, showing representative images for different treatment times. In FIG. 9A, one day following treatment, the epithelial cells have de-nucleated without evoking a substantial immune response. Seven days after stimulation (FIG. 9B), a substantial necrotic crust 903 has formed on the tissue from the de-nucleated cells. This crust progressively recedes (e.g., is removed or simply falls off), as shown in FIGS. 9C-9E (at fifteen days, thirty days or sixty days, respectively). For side-by-side comparison with the histological sections, FIGS. 10A-10C show the sections of FIGS. 6A-6C.

Figure 11A:
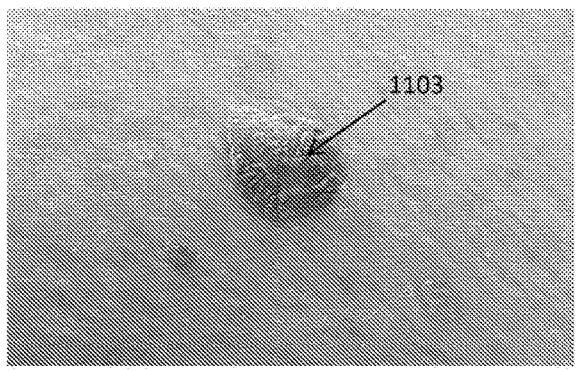
FIGS. 11A-11D illustrate a method of treating skin to remove a lesion, shown as a mole in FIG. 11A.
Figure 11B:
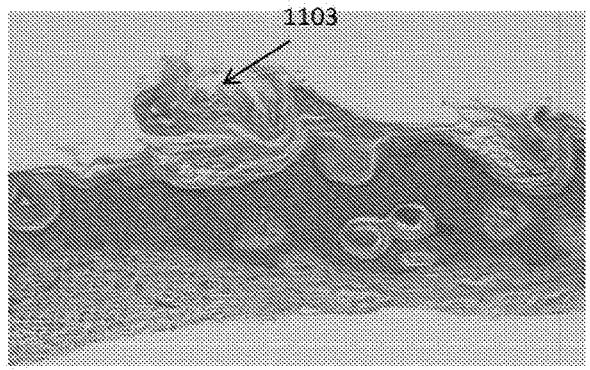
Figure 11C:
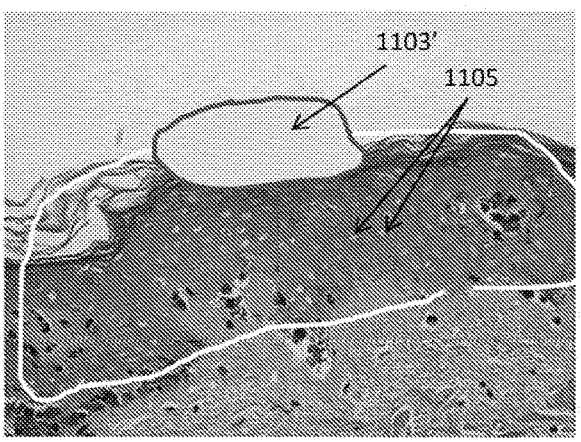
Figure 11D:
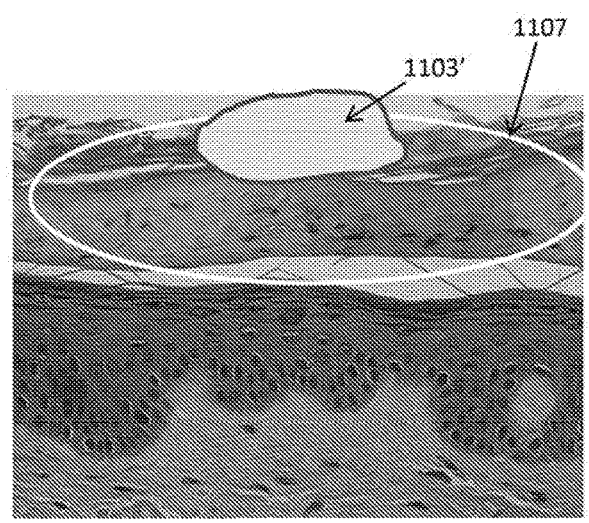

In general, any of the methods and apparatuses described herein may be used to treat skin having a lesion by de-nucleating the epidermal cells comprising, surrounding or underlying the lesion. For example, FIGS. 11A-11D illustrate one method of treating a seborrheic keratosis (SK). SKs are one of the most common noncancerous skin growths on older adults, appearing as small, rough bumps. FIG.11A illustrates an example of an SK 1103 on a patient's skin, and FIG. 11B is a histological section through a typical SK. The methods and systems described herein may be used to treat a lesion such as SK as shown in FIG. 11C, prophetically illustrating what treatment of a region of skin including a simulated SK 1103' in a region of tissue having epidermal cells has been de-nucleated 1105 as discussed above, forming "ghost" epidermal cells. FIG. 11D illustrates the exemplary section of FIG. 11C after seven days from treatment, in which the SK lesion 1103' forms part of the necrotic crust 1107 that will be removed from the tissue to expose new epidermis below the necrotic crust. In general, the longer the skin has to recover, the more like 'normal' skin it will resemble; the lesion may be partially or completely removed.

FIGS. 12A-12H illustrate a time course showing the surface of skin treated to remove an SK lesion 1203. In FIGS. 12A-12H, the skin is treated using an applicator such as the one shown in FIG. 12I having a plurality of needle-like electrodes 1207, 1211 extending from a base region 1209 so that the ultra-short, high-field strength electric pulses may be delivered between the electrodes. FIG. 12A shows the region of the human skin including the seborrheic keratosis 1203 prior to treatment. FIG. 12B shows the lesion immediately following delivery of the nano-pulse stimulation (in this example, 100 pulses of ultra-short, e.g., 100 ns, high-field strength, e.g., 30 kV/cm, electric pulses were delivered over 50 seconds) in order to de-nucleate the epithelial cells in the region. FIG. 12C shows the same region of skin one hour after treatment. By 18 hours post treatment the necrotic crust 1205 has begun forming, which is also visible in FIG. 12E. One week following treatment (FIG. 12F), the necrotic lesion has fallen off (or otherwise been removed), exposing the new skin forming. FIGS. 12F and 12G show the resulting skin after two weeks and three weeks, respectively.

Figure 13A:
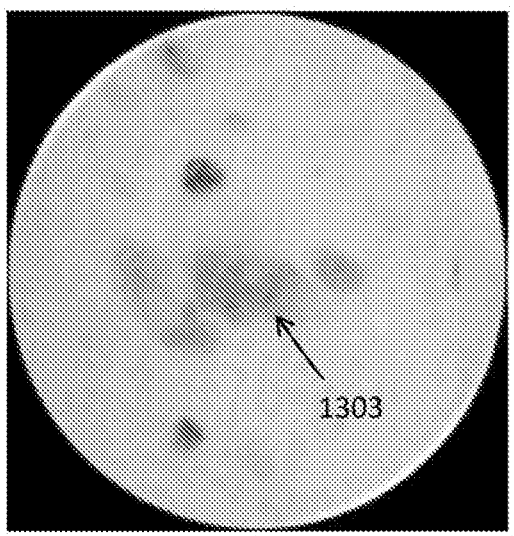
FIGS. 13A and 13B illustrate the skin appearance after healing in a thermally (e.g., cryosurgically) treated skin region.
Figure 13B:
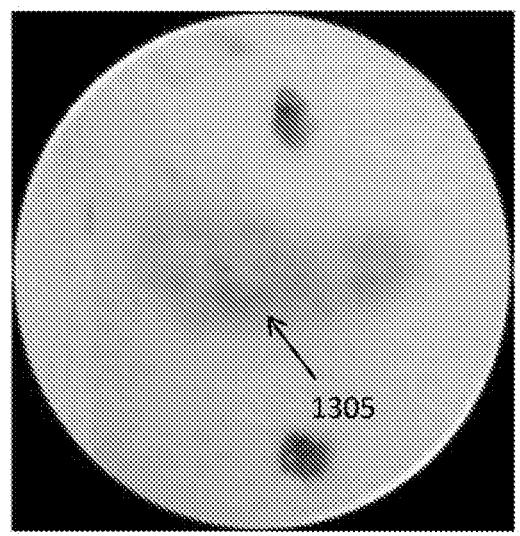
Figure 14A:
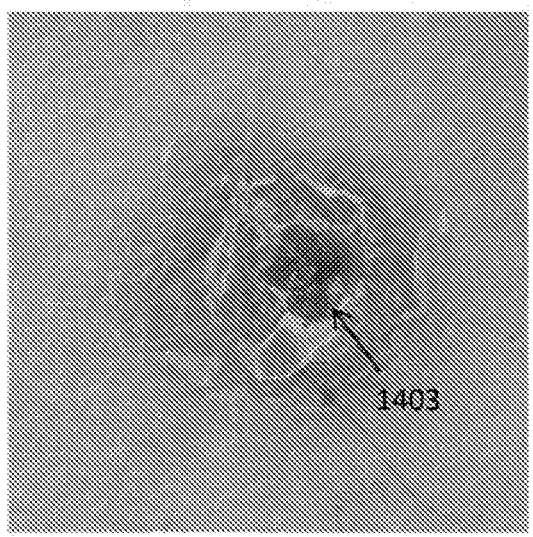
FIGS. 14A and 14B illustrate skin treated with a pulsed electrical treatment to de-nucleate epidermal cells within the region without provoking a substantial inflammatory response (e.g., using a nano-pulse stimulation, e.g., ultra-short, high-field strength electric pulses).
Figure 14B:
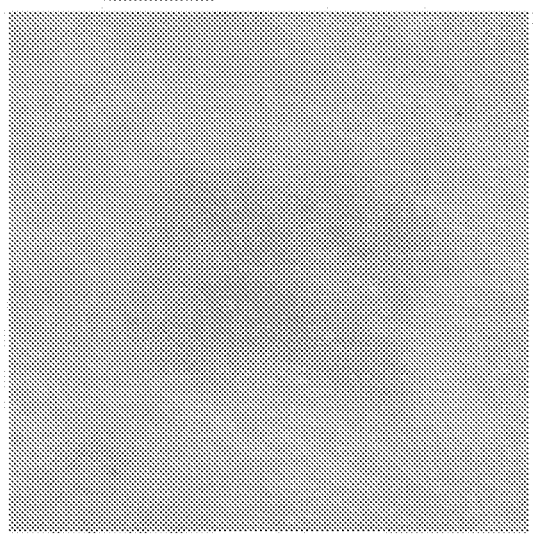

The methods and systems described herein may generally provide a superior appearance, e.g., more natural color and/or less scarring, compared to other, particularly thermal, skin treatment methods. For example, FIGS. 13A and 13B illustrate recovery following cryosurgical treatment of a skin region including a lesion. FIG. 13A shows a region of skin including a skin lesion 1303. Three months (90 days) following cryosurgical treatment of the lesion, the skin remains discolored 1305, as shown in FIG. 13B. By contrast the methods (including the use of nano-pulse stimulation as described herein) may provide therapies with less discoloration and scarring, as shown in FIGS. 14A-14B. in FIG. 14A, a (simulated) lesion may be removed by de-nucleating the epidermal cells without provoking a substantial inflammatory response; the skin showing the resulting necrotic crust 1403 is shown for 15 days post-treatment (e.g., following a moderately-high treatment level, TL5). By sixty days post-treatment, as shown in FIG. 14B, the lesion has been removed (along with the necrotic crust), leaving the skin reasonably clear and free of discoloration.

According to one aspect, an apparatus for treating tissue (e.g., skin disorders, skin abnormalities, skin lesions and tumors) is provided. The apparatus comprises a pulse generator; a set of electrodes; and a controller configured to control, at least partially, operation of the pulse generator. The controller may optionally comprise a processor having a set of instructions, the controller is operable to cause the pulse generator to generate and apply through the set of electrodes a pulsed electrical treatment to a region of tissue to de-nucleate cells within the region without provoking a substantial inflammatory response, so that the tissue forms a necrotic crust and forms new tissue below the necrotic crust so that when the necrotic crust is removed the new tissue is exposed. Any of the apparatuses described herein may include a hand-held applicator having a handpiece that plugs into an applicator. For example, FIG. 15A shows an example of a handpiece 1501 that may plug (via cord 1503) to a generator (not shown) for generating the nano-pulse stimulation. One or more different tips may couple with the handpiece; the tips may include the electrode(s) for delivering the energy to the skin, as described above. For example, FIGS. 15B-15D illustrate exemplary electrode tips for treating skin by delivering nano-pulse stimulation as described herein. In FIG. 15A, the tip fits over the distal end of the headpiece 1505, and snaps or locks in place once electrical contact is made with the projecting (needle-like) electrodes 1511. For example, the tip may be mechanically secured (e.g., by snap-fit, friction fit, etc.) onto the end of the handpiece. In FIG., 15B, two electrodes are provided, and each is sufficiently sharp so that it may penetrate the skin. One electrode may be the cathode and the other electrode the anode. The electrodes may be pointed and/or sharp, or otherwise configured to penetrate the tissue. The region between the electrodes may be adapted to fit over a skin lesion that projects from the skin. FIG. 15C shows a tip 1507 that includes two parallel rows of sharp, tissue penetrating electrodes that may all simultaneously penetrate the skin in the region including or surrounding the skin lesion. In this example, the electrodes (or electrode pairs) may be separately addressed by the apparatus, or they may be connected together. For example, in FIG. 15C, the left row of electrode may be electrically connected (e.g., acting as a cathode) and the right row of electrodes may be electrically connected (e.g., acting as an anode).

FIG. 15D illustrates an example of a non-penetrative (e.g., surface) tip 1509 including electrodes that are configured to deliver nano-pulse electrical energy as described herein. In FIG. 15D, an outer ring of electrode surrounds an inner electrode; these electrodes may act as an electrode pair for delivering energy (e.g., current) to the skin. The tips in FIGS. 15B-15D may be swapped.

Rotation of Electrode Pattern

Also described herein are methods and apparatuses/systems in which the electrodes applying the energy are rotated partway through the application of the treatment. These methods and apparatuses may be used to treat any tissue, including (but not limited to) skin. Surprisingly, when compared to an identical treatment in which the electrodes delivering the pulsed electrical treatment are not rotated, the amount of energy required to treat the tissue (e.g., to achieve a lesion of a predetermined size) is significantly less. The methods and systems disclosed herein may generally provide a more efficient treatment, for example, requiring less energy to be applied to the tissue (e.g., fewer pulses, lower energy pulses, shorter treatment times, etc.) in order to achieve therapeutically desirable treatments. These methods and apparatuses may allow to increase the treatment volume or size and improve targeting accuracy. The systems and methods of the present disclosure may provide, among other benefits, the improved increased treatment volume. For example, when the treatment comprises a plurality of pulses, such as sub-microsecond electrical pulses, the number of pulses required to achieve a predetermined lesion size when the electrodes are rotated partway through the treatment as disclosed herein may be substantially less than the number of pulses required if the electrodes are not rotated. For example, the number of pulses, required to form an equivalently-sized lesion by pulsed electrical treatment may be reduced by between about 40% and 20% when rotation (e.g., rotation by 90 degrees) is implemented, compared to treatment without rotation of the pattern of electrodes applying the pulsed electrical treatment. In addition, the methods and systems disclosed herein may provide not only for the larger volume but also for more consistent and uniform volume. Moreover, using in some implementations, automated, including computer controlled, systems may provide precise and accurate rotating and repositioning of the energy delivery device (e.g., rotation of the electrode pattern) in the same treatment region. Rotation, as used here, may refer to the rotation of the pattern of two or more electrodes, including (but not limited to) tissue penetrating electrodes, such as needle electrodes. Rotation of the pattern of electrodes may be relative to a target tissue region. In general, the rotated pattern may be rotated by any amount of rotation (e.g., between 0.5 degrees to 359.5 degrees, such as between 5 degrees and 355 degrees, between 10 degrees and 350 degrees, between 20 degrees and 340 degrees, between 30 degrees and 330 degrees, between 40 degrees and 320 degrees, approximately 90 degrees, etc.). The rotation may be clockwise and/or counterclockwise. As described in detail below, rotation may be physical rotation of the pattern of electrodes (e.g., the applicator) relative to the tissue, or rotation by changing the active electrodes of an array of electrodes so that the pattern of active electrodes is rotated relative to the target tissue. The pattern of electrodes may be rotated relative to a region of tissue (e.g., a target region of tissue) so that after rotation the same region of tissue is being modified. For example, the treatment tip may be positioned on the same region of the tissue before and after rotation.

Figure 17:
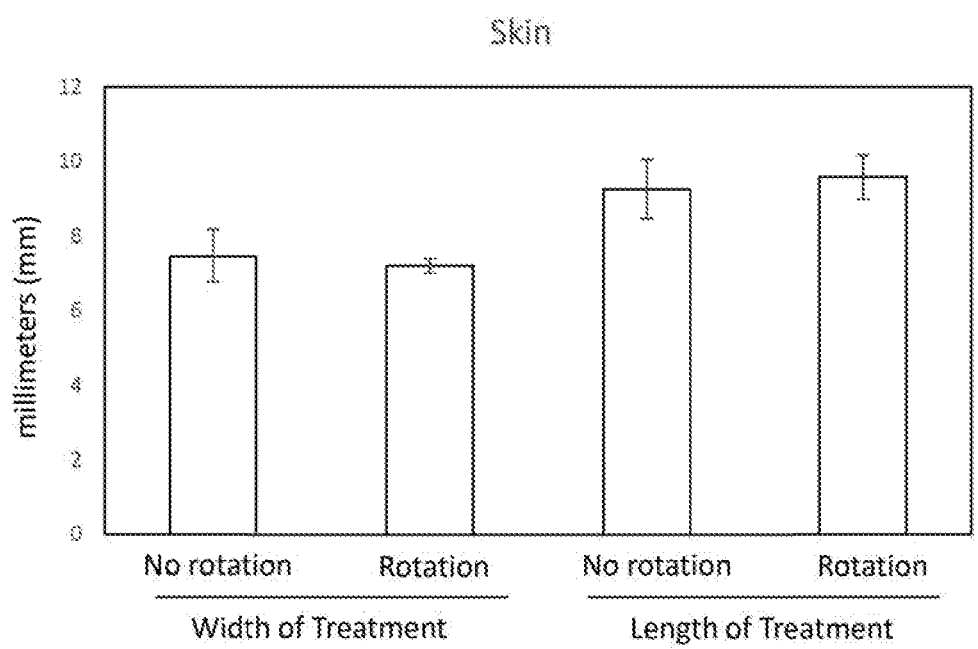
FIG. 17 is a graph illustrating an example of the efficacy of rotating the electrodes during treatment of skin, showing that rotating the electrodes during treatment resulted in similarly sized lesions (in width and length) while requiring substantially fewer pulses.

For example, FIG. 17 illustrates a graph showing that electrical stimulation when the electrodes are rotated halfway through treatment ("rotation") compared to lesions formed without rotating ("no rotation") results in a reduction of the number of pulses by about 25% while creating a nearly identically-sized lesions (mean width of the lesions +/−SEM is shown on the left, mean length +/−SEM is shown on the right). In FIG. 17, tissue (e.g., pig skin) was treated with 134 pulses during treatment without rotating the electrodes ("No rotation", n=4 animals) using a pattern of electrodes on the end of an applicator tp. A similar region of tissue was treated with 100 pulses, but halfway through the treatment (after 50 pulses), the treatment tip was rotated at the same tissue region, in this example by 90 degrees. Tissue was assessed after four days from the application of energy. Error bars on each column in FIG. 17 are +/−SEM. Both the width and length of the resulting lesions were comparable. The treatment was otherwise identical between the "rotation" and "no rotation" groups and was performed at the same nanosecond pulse conditions with a 3 mm long trocar tip, using 300 ns pulses. Tissue was assessed after four days from the application of energy.

Nearly identical results were seen with other tissue types as well. For example, FIG. 18 shows a similar trend for kidney tissue, using the same experimental protocol as in FIG. 17, and FIG. 19 shows the same trend with liver tissue, again using the same experimental protocol as in FIG. 17.

Figure 18:
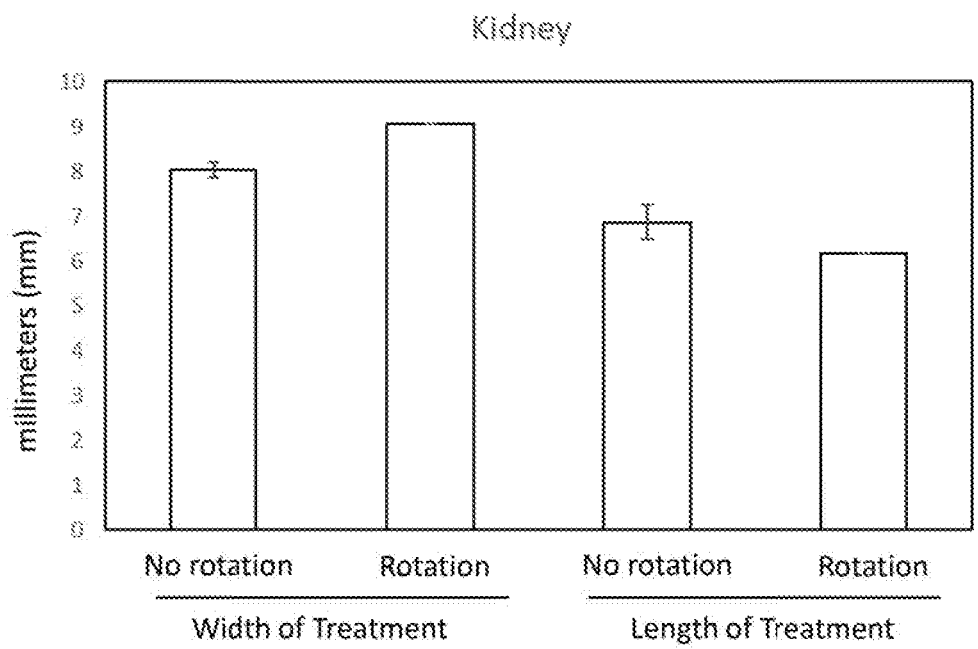
FIG. 18 is a graph illustrating the efficacy of rotating the electrodes during treatment of non-skin tissue, such as kidney tissue (e.g., pig kidney), also showing that rotating the electrodes at some point during treatment resulted in similarly sized lesions (in width and length) while requiring substantially fewer pulses.

In FIG. 18, tissue was stimulated with 134 pulses during treatment without rotating the electrodes ("No rotation", n=2 animals), while only 100 pulses were required to achieve a comparable lesion when the electrode was rotated halfway through treatment by, in this example, 90 degrees ("Rotation", n=1 animals). Both the width and length of these lesions were comparable. All pulsing was performed at the same nanosecond pulse conditions with a 3 mm long trocar tip, using 300 ns pulses. Tissue was assessed after four days from the application of energy. Error bars on each column in FIG. 18 are +/−SEM.

Figure 19:
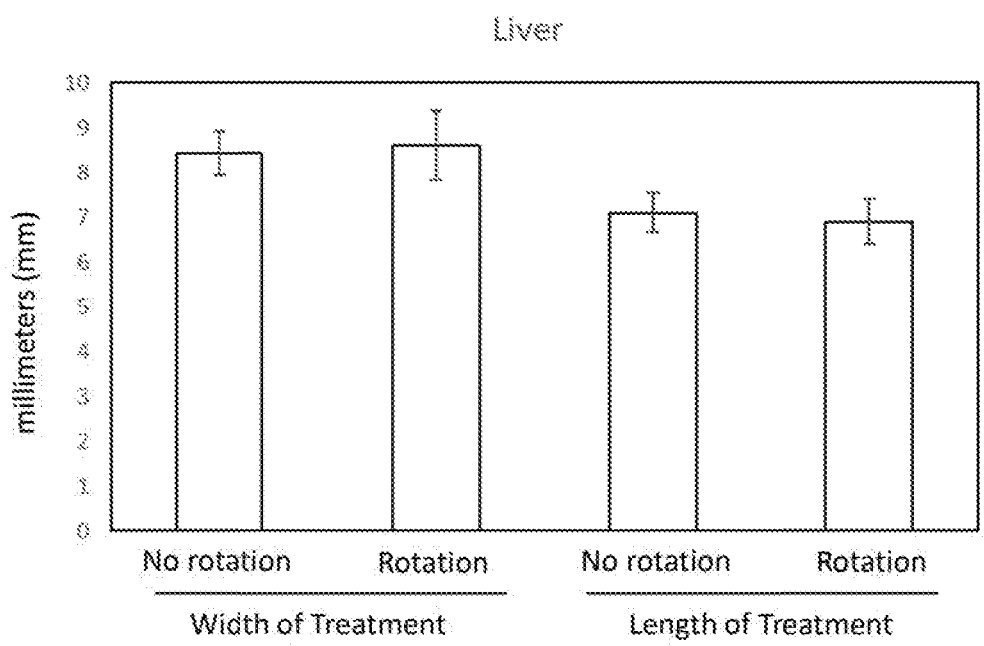
FIG. 19 is a graph illustrating the efficacy of rotating the electrodes during treatment of non-skin tissue, such as liver tissue (e.g., pig liver), also showing that rotating the electrodes at some point during treatment resulted in similarly sized lesions (in width and length) while requiring substantially fewer pulses.

In FIG. 19, tissue was stimulated with 134 pulses during treatment without rotating the electrodes ("No rotation", n=2 animals), while only 100 pulses were required to achieve a comparable lesion when the electrode was rotated halfway through treatment by, in this example, 90 degrees ("Rotation", n=2 animals). Both the width and length of these lesions were comparable, as shown. All pulsing was performed at the same nanosecond pulse conditions with a 3 mm long trocar tip, using 300 ns pulses. Tissue was assessed after four days from the application of energy. Error bars on each column in FIG. 19 are +/−SEM.

Thus, in general it may be beneficial when applying a treatment to a tissue to rotate the pattern of electrodes applying energy to the tissue partway through the treatment, since, in addition to other benefits identified above, it may require less energy, which may reduce any risks associated with the procedure, and may speed tissue recovery.

Figure 27:
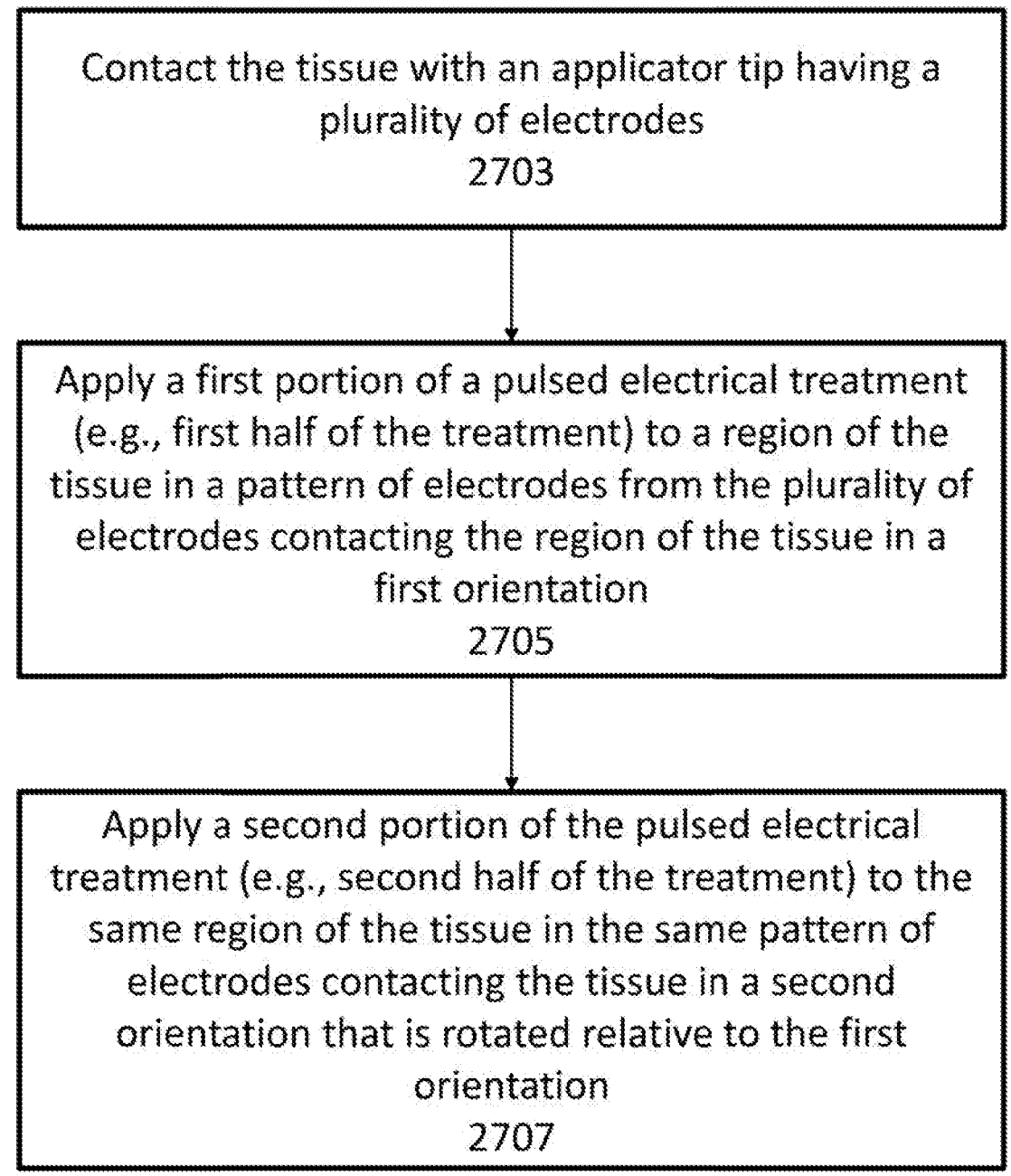
FIG. 27 is a flow chart illustrating one example of a general method of rotating a pattern of electrodes relative to a tissue region.

FIG. 27 describes a general method of treating a tissue according to some implementations of the present disclosure. The method may include contacting a tissue with an applicator tip having a plurality of electrodes in a pattern of electrodes (step 2703). The tissue may be any tissue, and the electrodes on the applicator tip may be inserted into the tissue, or, in some variations, placed against the tissue without penetrating the tissue. A first portion of the treatment may then be applied to a region of the tissue through a pattern of electrodes from the plurality of electrodes in a first orientation (step 2705). Before applying the second portion of the treatment, in some implementation of the method the pattern of electrodes may be rotated by some predetermined amount relative to the first orientation (e.g., between 5 degrees and 175 degrees (or in some variations between 1 degree and 359 degrees, etc.). In some variations the plurality of electrodes is rotated by 90 degrees. The rotation may be done manually, automatically, and/or semi-automatically. In some variations, the electrodes are rotated robotically, as discussed in greater detail below. Alternatively, rotation of the pattern of electrodes may be done by switching the active electrodes in an array of electrodes. For example, the applicator tip may comprise an array of electrodes in which the plurality of electrodes is a first subset of active electrodes forming the pattern of electrodes and a step of applying the second portion of the pulsed electric treatment comprises forming the pattern from a second subset of active electrodes from the array of electrodes in which the pattern formed by the second subset is the same pattern but rotated relative to the first subset. Once the pattern is rotated relative to the tissue, the second portion of the treatment may be applied to the same region of the tissue in a second orientation (step 2707).

Figure 28:
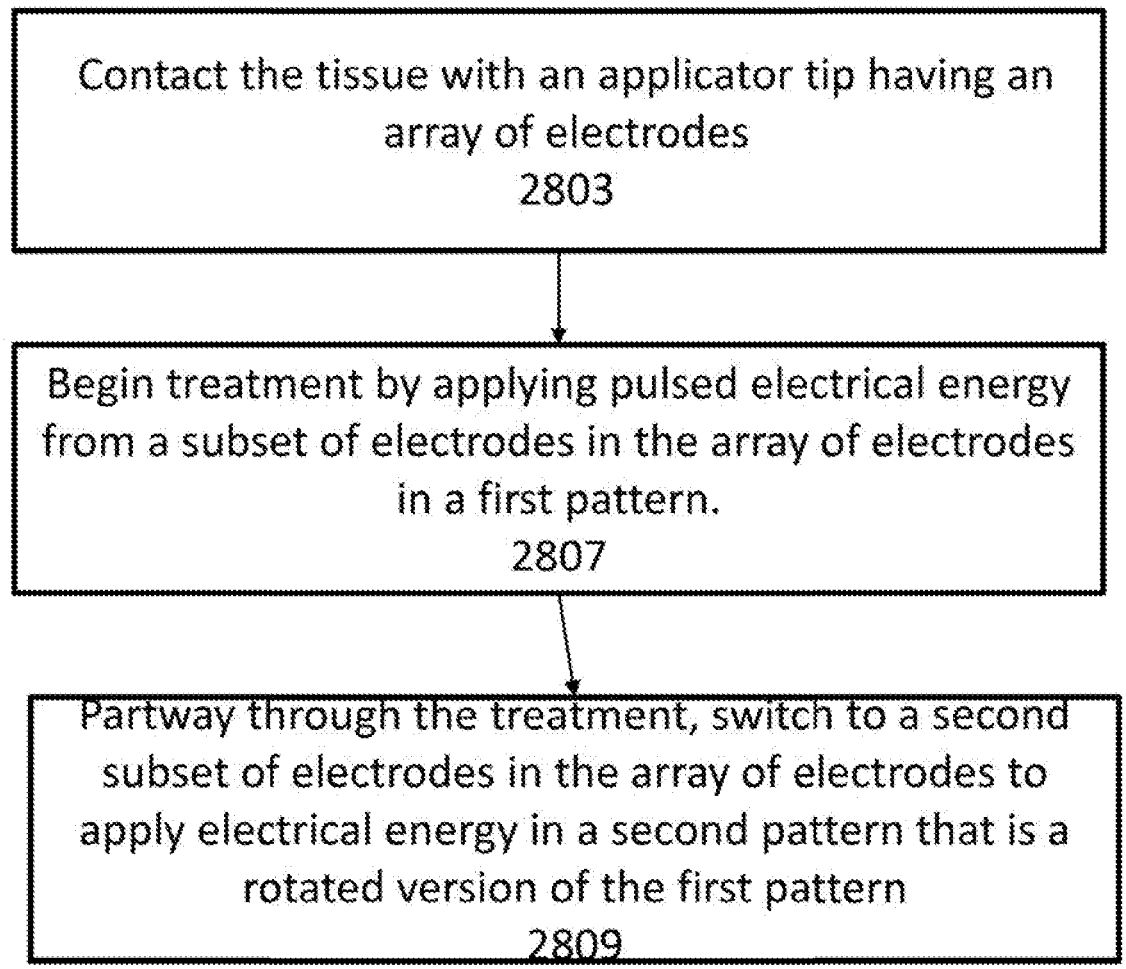
FIG. 28 is a flow chart illustrating one example of a method of rotating a pattern of electrodes relative to a tissue region, for example, without removing the electrodes from the tissue.

FIG. 28 describes an exemplary method in which the rotation of the pattern is achieved by changing a sub-set of active electrodes in an array of electrodes that are used to apply the pulsed electrical energy part way through the treatment so that the pattern is rotated relative to the initial subset of electrodes. For example, in FIG. 28, the applicator (e.g., applicator tip) having an array of electrodes may contact the tissue (step 2803). In some variations, the surface of the tissue may be contacted. In some variations, the electrodes may penetrate the tissue. A pulsed electrical treatment (including, but not limited to the application of nanosecond electrical pulses) may be delivered by a sub-set of the electrodes in the array that are arranged in a first pattern (step 2807). Partway through the treatment, and without removing the treatment tip from the tissue, switching to a different (e.g., second) sub-set of electrodes in the array arranged in a second pattern that is a rotated version of the first pattern (step 2809). In other words, the second pattern may be exactly the same as the first pattern, except that its orientation is rotated relative to the orientation of the first pattern. The rotated version maybe rotated by any amount, which may be determined by the arrangement of the array of electrodes.

For example, the pattern may be rotated by 25 degrees, by 45 degrees, by 90 degrees, etc. Switching to the second (rotated) pattern partway through treatment may be switching midway (e.g., approximately halfway) though the treatment, or switching after any appropriate fraction of the total treatment time (e.g., 30%, 40%, 50%, 60%, 70%, etc.). Switching to a different subset of electrodes may be accomplished without moving the applicator tip or the array of electrodes, for example, by simply activating different electrodes in the array of electrodes. Switching to a different subset of active electrodes may be done automatically under control of a controller and/or a processor.

According to some implementations, a method of treating a tissue is provided. The method comprises a treatment, such as a pulsed electrical treatment, comprising a plurality of nanosecond electrical pulses having a pulse duration of between 0.1 ns and 1000 ns, wherein the treatment is divided into a first portion and a second portion (for example, wherein the first portion is between 30% and 70% of the pulsed electrical treatment). The method comprising contacting the tissue with an applicator tip having a plurality of electrodes in a pattern of electrodes; applying the first portion of the treatment to a region of the tissue through the plurality of electrodes with the pattern of electrodes contacting the region of the tissue in a first orientation; removing the plurality of electrodes from the region of the tissue; rotating the applicator tip (for example, through a midline of the applicator tip or a midline of the plurality of electrodes); re-applying the plurality of electrodes to the region of the tissue; and applying the second portion of the treatment to the same region of the tissue through the plurality of electrodes with the pattern of electrodes contacting the region of the tissue in a second orientation that is rotated relative to the first orientation.

It will be apparent that the number of steps of the methods that are utilized are not limited to those described above. Also, the methods do not require that all the described steps are present. Although the methodology described above as discrete steps, one or more steps may be added, combined or even deleted, without departing from the intended functionality of the embodiments of the disclosure. The steps can be performed in a different order or have the steps shared between more than one processor, for example. It will also be apparent that the method described above may be performed in a partially or substantially automated fashion, including performed using robotic systems.

Figures 20A, 20B:
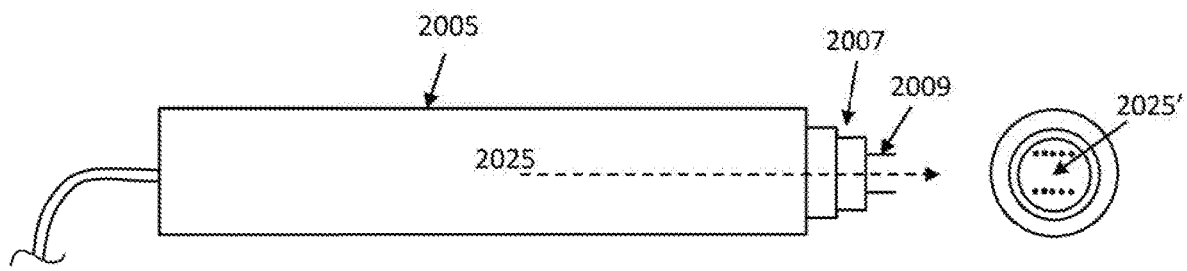
FIGS. 20A-20F schematically illustrate a first example of an electrical applicator (e.g., hand piece with tip) for delivering energy as described herein, including (but not limited to) the delivery of nano-pulse stimulation.

Any energy delivery device or applicator, or applicator hand piece may be used to apply the treatment and rotate the electrodes of such energy delivery device or applicator partway through the treatment. The rotation may be performed manually or automatically using a mechanism, for example, as described herein. In some variations the applicator is adapted to allow the pattern of electrodes at the distal tip to be rotated at the target tissue partway through a treatment. For example, FIGS. 20A-20F illustrate one example of an apparatus that is configured to rotate the electrodes relative to the tissue partway through a treatment to the tissue. In FIGS. 20A-20B a first configuration of an applicator is shown. FIG. 20A shows a side view of a handle portion 2005 and a treatment tip 2007. A plurality of electrodes, shown as needle electrodes, are included on the distal end of the treatment tip, and are arranged in a pattern of two parallel lines of needle electrodes 2009, shown in the front view of FIG. 20B, looking down onto the applicator tip.

Figures 20C, 20D:
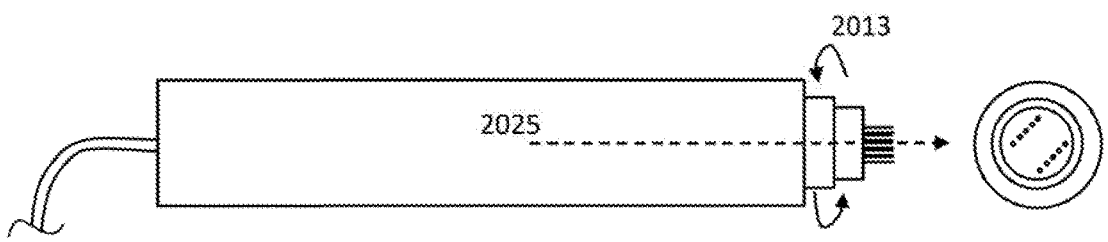

The apparatus shown in FIG. 20A-20B is configured so that the pattern of electrodes may be rotated or turned as shown in FIG. 20C by arrows 2013 either clockwise and/or counterclockwise partway through the treatment. As used herein, the term "partway" is not intended to require the exact one-half of the treatment but is intended to mean any desired or appropriate point during duration of the treatment. In FIG. 20C, the applicator distal tip 2007 can be separately rotated, as shown by arrows 2013. This rotation may be motorized, and may be controlled, for example, by a button, switch, actuator, or other controller (which collectively may be referred to as "a mechanism"), and may be automatically or semi-automatically controlled. In FIG. 20D the tip is shown rotating counterclockwise (an approximately 45 degrees rotation is shown by example). In some variations, as shown in FIGS. 20E and 20F, the pattern of electrodes at the distal tip of the applicator may be rotated 90 degrees (and/or other desired angles), as shown, and as is apparent in FIG. 20F.

Figures 20E, 20F:
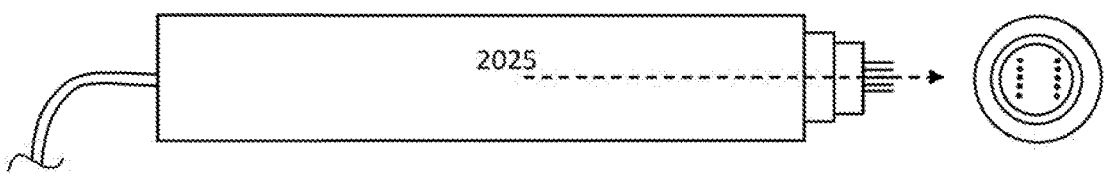

In FIGS. 20A-20F, the pattern of electrodes on the treatment tip are rotated about a line of rotation 2025 along the treatment tip (in the long axis of the applicator), and through a point of rotation in a plane of the pattern of electrodes. This line of rotation may, in some variations, be referred to as a midline, as it may pass through the point of rotation 2025' which may be in the middle (or center) of the pattern of electrodes in the plane of the electrodes. As shown in FIGS. 20D and 20F, the pattern of electrodes rotates about this line of rotation 2025.

Another variation, similar to the apparatus shown in FIGS. 15A-15D is shown in FIG. 21A. In this variation, the apparatus includes a handpiece 2101 that may plug (via cord 2105) to a generator (not shown) for generating electrical stimulation, for example, the nano-pulse stimulation. The handpiece 2101 may be an energy delivery device in a form configured for the attachment to a movable arm of the robotic system, or in a form to be held by human operators. The distal end region of the hand piece in this example is configured to be controllably rotated during the application of energy (e.g., partway through a treatment). In FIG. 21A, the hand piece may plug into a generator and/or controller, which may also control the rotation. One or more different tips (FIGS. 21B and 21C) may couple with the handpiece; the tips may include different patterns of electrodes for delivering the energy to the tissue, as described above. In addition, in the variation shown in FIG. 21A, the handpiece may be configured so that the applicator tip may controllably rotate, as shown by arrows 2104. This rotating region may include a turning joint and may be electrically driven and controlled by user input and/or by an applicator controller (not shown). FIGS. 21B-21C illustrate exemplary electrode tips for treating skin by delivering nano-pulse stimulation as described above. In FIG. 21A, the tip fits over the distal end of the headpiece 2101, and snaps or locks in place while electrical contact is made with the projecting (needle-like) electrodes 2111, 2111'. For example, the tip may be mechanically secured (e.g., by snap-fit, friction fit, etc.) onto the end of the handpiece. The handpiece may drive rotation of the distal tip.

In some variations, rather than a portion of the handpiece and/or applicator tip move (e.g., rotate), the entire handpiece may be rotated. As mentioned this may be done manually. For example, it may be manually rotated by an operator using a mechanism having an actuator to effect manual rotation thereof. In some variations it may be beneficial to rotate the handpiece robotically.

Alternatively or additionally, in some variations it may be desirable to avoid physical rotation of the electrodes. For example, in some of the manual implementation to avoid a possibility of targeting error and the possibility of untreated or over-treated tissue, the methods for treating tissue may be implemented without having to reposition or move the electrodes while still achieving the benefits of the increased treatment volume and/or providing treatment in multiple directions. Such implementations are illustrated in FIGS. 22A-22F, 23A-23B, 24A-24B and 25A-25H. In each of these examples, a front view looking down on the electrodes is shown. Each of these tips includes an array of electrodes that are either active (shown by shaded circles) or inactive (shown as open circles). Active electrodes may be in contact with the tissue and configured to apply energy through the electrode into the tissue. In contrast inactive electrodes may be insulated from the tissue, so as not to electrically interact with the tissue, and/or they may be withdrawn from the tissue, e.g., into the applicator tip. The inactive electrodes also may remain in the tissue but not connected so that they are floating. Thus, in variations in which the pattern of electrodes is rotated by switching between sets of active electrodes, the applicator tip does not need to rotate relative to the tissue but may remain on/in the tissue while rotating the pattern of electrodes by changing which electrodes are active or inactive partway through the treatment.

For example, FIG. 22A is an example of an applicator tip having a first pattern of active electrodes, showing two parallel lines of three electrodes each. The applicator tip in this example includes a total of 8 electrodes; in FIG. 22A, the two middle electrodes are inactive. FIG. 22B illustrates rotation of the pattern of electrodes shown in FIG. 22A by switching which electrodes are active; in this example, the six vertical electrodes are active so that the two parallel lines of active electrodes resulting are perpendicular (e.g., rotated by 90 degrees) relative to the orientation of the active electrodes in FIG. 22A. The first pattern of active electrodes may be rotated relative to tissue being treated by the electrodes by changing which electrodes of the tip of the applicator are active. The first pattern of active needle electrodes is shown in the front view of FIG. 22A by the shaded circles 2207; inactive needle electrodes are shown unshaded 2209. During use, partway through the treatment, the pattern of active electrodes may be switched to that shown in FIG. 22B. This effectively rotates the pattern of FIG. 22A by 90 degrees. In some variations, the electrodes may remain in the tissue. Alternatively or additionally, in some variations the inactive electrodes may be withdrawn from the tissue, including withdrawn axially into the applicator (e.g., into an insulated housing within the applicator). Thus, the applicator tip may remain in/on the tissue.

FIGS. 22C-22F show an alternate arrangement of an applicator tip having stationary needles arranged in rows and columns creating a perimeter pattern, for example, on a square or rectangular tip end wall 2210. Initially, for example, the right and left-hand perimeter columns of the needle electrodes may be electrically connected to the pulse generator and act as active electrodes during treatment. Then, in the alternate configurable arrangement, as shown, the top and bottom row perimeter needles can be energized or activated, for example, by manually or automatically manipulating a switch plate, such as a rotatable connector switch plate 2217. Manipulation of the switch plate causes connectors (e.g., banks of connector jacks) 2213, 2215 to engage with a respective row or column of needles. FIG. 22C shows an applicator tip 2208 with fixed needles 2209. The pulse applicator tip 2208 includes a cylindrical base portion having a housing groove 2221 in which switch plate tab 2219 (an example of an actuator operable to be either manually or automatically manipulated) is guided and moves. FIG. 22D shows a cutaway view of the internal configuration of the pulse applicator tip 2208 with the switch plate 2217 in a connected (e.g., forward engaged) position 2223. The needles 2209 are fixed to the applicator tip end wall 2210. For convenience of description we will discuss the electrical connections to the needle electrodes referring to either the top and bottom rows or to the left-hand and right-hand columns. By way of example, each perimeter side has 4 fixed needles distributed in a line along it. The switch plate 2217 includes a first connector 2213 and a second connector 2215. When the switch plate 2217 along with its connector banks 2213, 2215 are in their engaged or connected position, the switch plate tab or tab 2219 may be at its most forward lower position within the housing groove 2221. In this arrangement the electrical wiring connecting to the connectors is not shown. The first connector 2213 and the second connector 2215 are fully engaged with the electrically conductive exposed ends of the fixed needles inside the applicator housing. FIG. 22E shows the configuration of pieces in a transition position 2225 where the first connector 2213, the second connector 2215, and the switch plate 2217 all may be retracted and the switch plate tab 2219 is approximately in the middle of its circumferential travel along the groove 2221. The needles may be insulated to prevent arcing between oppositely charged needles inside the applicator tip. This figure shows the needles having needle insulation extending from the inside of the applicator tip end wall 2210 to leave exposed and bare electrode portion of the needle. The bare electrode portion of the needles allows for the connector 2229, such as spring connector 2229 shown in FIG. 22F to make an electrical connection to the needles. FIG. 22F shows a cross-section of the rotatable switch plate 2217 and a cross-section of the first connector 2213 and the second connector 2215 with the inside ends of the fixed needles 2209 being captured by individual spring connector jacks 2229 inside the first and second connectors 2213, 2215. In this example, mechanical switching is done between the left and right-hand perimeter columns of needles on the applicator tip end wall and the top and bottom rows of needles in the applicator tip end wall. When switched, those electrodes (e.g., middle) located between the energized or active electrodes are left electrically floating.

FIGS. 22G-22L illustrate a pulse applicator with field and mechanical rotation accomplished by using movable needles. FIGS. 22G and J show the pulse applicator 2235 having an end wall 2239 and an array of needles arranged along a perimeter of the end wall. FIG. 22G shows, by example, 2 columns of 4 needles each extending from the end wall. In this example, two middle needles or electrodes 2246 of each row are movable (e.g., retractable and extendable) while each of the top and bottom needle 2237 of each column (as seen in FIG. 22H) are stationary. The pulse applicator 2235 includes a switch plate 2257, a cylindrical base portion which may have a groove 2261 in which switch plate tab 2259 is guided and indicates relative position of the internal switch plate 2257. For example, the stationary needles may be connected to the housing. The movable needles may be connected, for example, to the plate 2257. FIGS. 22G and 22J show respectively external prospective and cross-sectional views of a first connected position 2263 where all electrodes/needles of the two columns of electrodes of the applicator tip are electrically connected and active. As can be seen in FIGS. 22H and 22K, the switch plate 2257, which may be a rotatable switch plate, is shown in a retracted position 2265 along with the retractable needles 2246 while stationary needles (in this example, corner needles 2237) remain in place and stay extended. This allows to maintain the tip position in the treatment site. Each needle electrode may include an insulation 2247 to present arcing inside the applicator tip. A series of needle guides 2245 guide the movable needles into position (through their respective open holes in the end wall 2239 as the rotatable switch plate 2257 moves forward along with the movable needles 2246. In the example of FIG. 22K, the four corner connectors 2251 along with the exposed ends 2253 of the fixed/stationary needles (which act as plugs to match the jacks of the connectors 2251) make the electrical connection to the respective needles. FIGS. 22I and 22L show a second switched position, where the plate 2257 is rotated such that the movable electrodes 2246 are now extended along the top and bottom rows 2243 and the switch plate tab 2259 is seen in the upper forward position of the groove 2261. FIG. 22L is a cross-section of the arrangement of FIG. 22I and shows the forward extended position of the rotatable plate 2257 and the movable needles 2246 along with their insulation 2247 extending through the applicator tip end wall as guided by needle guides 2245. In the example of FIGS. 22H-22L, no floating needles are needed to be left in the treatment site. This configuration also may be useful if it is desired to reduce the number of the mechanical connections.

FIGS. 23A-23B illustrate a similar example, in which the initial pattern of two parallel rows of five electrodes is rotated by inactivating some electrodes and activating others to achieve the rotated configuration shown in FIG. 23B. In this example, the pattern of active electrodes is formed by two parallel lines of five electrodes. In FIG. 23A the first pattern (two rows of five needle electrodes) is shown. In FIG. 23B, the same first pattern is shown rotated by 90 degrees, for example. The pattern of electrodes may be rotated by changing which electrodes are active in the array of electrodes. Active needle electrodes are shown by the shaded circles in the front views of FIGS. 23A and 23B; inactive needle electrodes are unshaded. Partway (e.g., halfway) through the treatment, the pattern of active electrodes may be switched to from the pattern shown in FIG. 23A to the pattern shown in FIG. 23B to rotate the electrodes relative to the tissue. In this example, the pattern is rotated by 90 degrees, while some of the electrodes remain in the tissue. Inactive electrodes may be withdrawn from the tissue, such as by being withdrawn axially into the applicator (e.g., into an insulated housing within the applicator). Thus, the applicator tip may remain in/on the tissue even during rotation partway through the treatment.

In any of the arrays of the treatment tips and/or arrays of electrodes described herein, the plurality of electrodes may be arranged about a line of rotation along the treatment tip and/or applicator that passes through a point of rotation of the plurality of electrodes. This line may pass through a center of the plurality of electrodes and may, in some variations, be referred to as a midline through the pattern of electrodes ("midline") passing through a point of rotation at the center of this pattern of electrodes (midpoint of the pattern of electrode in the plane of the electrodes). An example of a line of rotation 2125 through the electrodes is shown in the treatment tip of FIG. 21B. The pattern formed by the electrodes (in some variations, the pattern of active electrodes) may be rotated about this line of rotation. In this example, the line of rotation is a midline trough both the array of electrodes and the treatment tip. In the frontal view of the electrode array shown in FIGS. 22A-22B, the line of rotation is a midline that passes through a point of rotation 2225 that is in the center of the array. The pattern of the active electrodes in FIG. 22A is shown rotated about this midline by 90 degrees in FIG. 22B. Similarly, in FIGS. 23A-23B the line of rotation passes perpendicularly through the point 2325 (point of rotation). The pattern of the electrodes shown in FIG. 23A is rotated 90 degrees about this line of rotation, as shown in FIG. 23B. The point of rotation may be the geometric center (central point) of the pattern of electrodes in the plane of the electrodes shown in the frontal views. The point of rotation may be a center point determined by approximating the distance from the centroid of each electrode to every other electrode centroid in the array of electrodes. The point of rotation is typically within the shape bounded by the array of electrodes (e.g., between them). In some variations the point of rotation may be along one or more lines of symmetry in the plane of the electrodes.

Figure 24A:
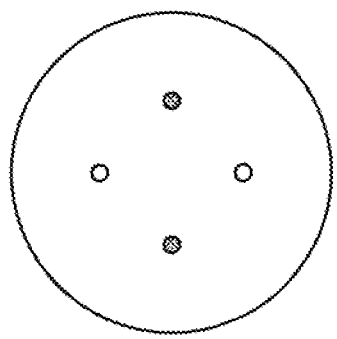
FIGS. 24A and 24B illustrate another example of an applicator having an array of needle electrodes that is configured to rotate the pattern of the electrodes on the tissue without having to move the electrodes by activating different subsets of the electrodes.
Figure 24B:
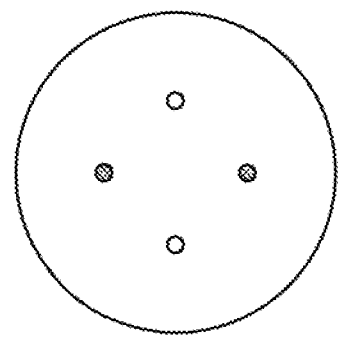

The electrode pattern shown in FIG. 24A shows a pair of electrodes that may be rotated by 90 degrees to achieve the pattern shown in FIG. 24B by switching the active and inactive electrodes in the array of four electrodes shown. In this example, the pattern of active electrodes is formed by two perpendicular lines of two electrodes. In FIG. 24A the first pattern (a line of two needle electrodes) is shown by the shaded circles, showing front views of the needle electrodes at the tip. In FIG. 24B, the same first pattern is shown rotated by 90 degrees. The pattern of electrodes may be rotated while on a target tissue region (and without moving from the target tissue region) by changing which electrodes are active in the array of electrodes. Partway (e.g., midway) through the treatment, the pattern of active electrodes may be switched to from the pattern shown in FIG. 24A to the pattern shown in FIG. 24B to rotate the electrodes relative to the tissue.

As discussed above, any appropriate rotation of the electrode patterns, e.g., by switching of the active electrode patterns, may be used. For example, FIGS. 25A-25D illustrate rotation of counterclockwise 45 degrees (between FIGS. 25A and 25B), rotation of 90 degrees (between FIGS. 25A and 25C) and rotation of clockwise 45 degrees (between FIGS. 25A and 25D). The applicator tip (not shown) may remain in the same position relative to the tissue, while different sub-sets of electrodes in the applicator tip are made active or inactive, as shown. In this example, it can be seen that the electrodes are arranged in a circular or round pattern (perhaps based on curved perimeter sides of an end wall of an applicator tip). The mechanical connections may be through at least two connectors configured to connect, for example, to opposite perimeter rows of electrodes as shown in FIGS. 25A-25D. It will be understood that curved comprises shapes such as round or oval, for example.

Figure 25A:
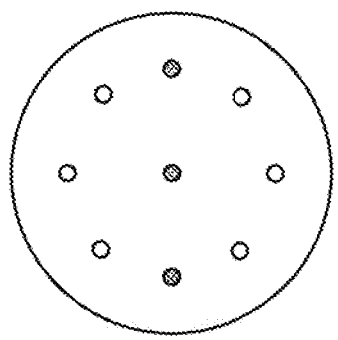
FIGS. 25A, 25B, 25C and 25D illustrate front views of a tip of an applicator that may rotate a pattern of electrodes by electrically or mechanically switching/activating different sub-sets of the electrodes to achieve an effect of rotation of the pattern relative to a tissue region by +/−45 degrees or 90 degrees, similar to FIGS. 22A-24B. The pattern of active electrodes shown in FIG. 25A is rotated by −45 degrees in FIG. 25B and by 90 degrees in FIG. 25C, and by 45 degrees in FIG. 25D.
Figure 25B:
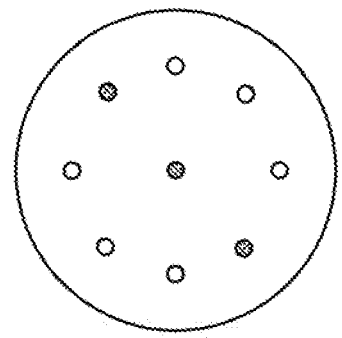
Figure 25C:
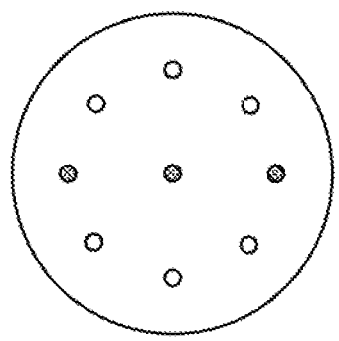
Figure 25D:
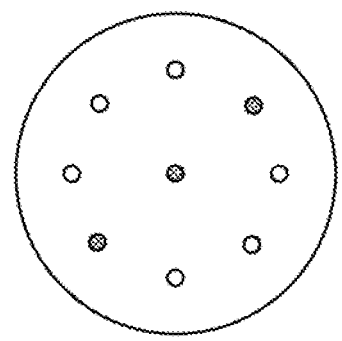
Figure 25E:
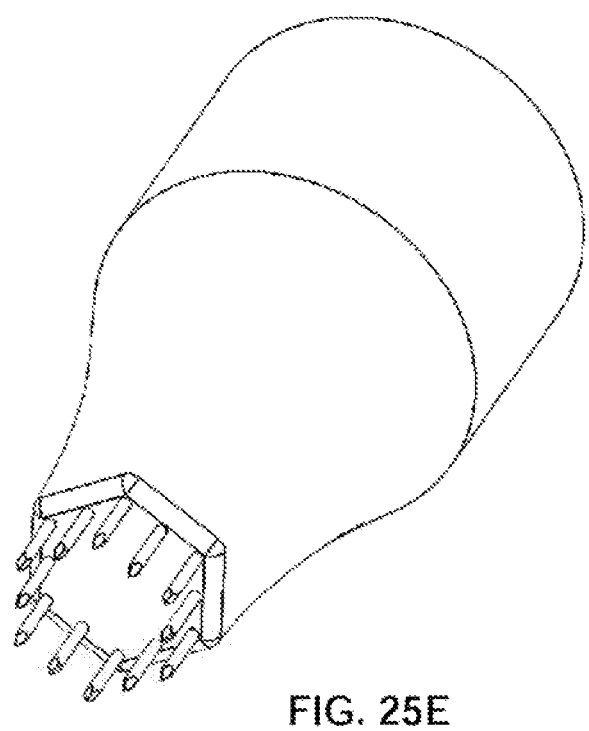
FIG. 25E-H illustrate an alternative tip shape with a hexagonal perimeter that may rotate a pattern of electrodes by electrically or mechanically switching/activating different sub-sets of the electrodes to achieve an effect of rotation of the pattern relative to a tissue region by +/−60 degrees.
Figure 25F:
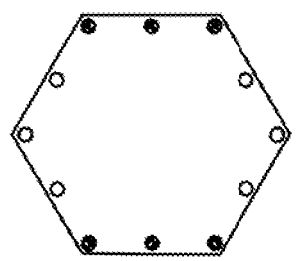
Figure 25G:
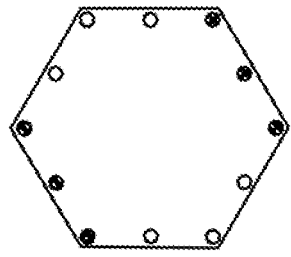
Figure 25H:
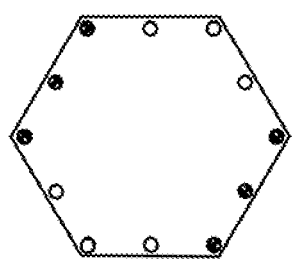

A further example shows a hexagonal perimeter applicator tip shape, in FIG. 25E. FIGS. 25F-25H illustrate rotation of the active electrode patterns (electric field rotation). A clockwise rotation of 60 degrees is illustrated between FIGS. 25F and 25G, and a further clockwise rotation of 60 degrees is illustrated between FIGS. 25G and 25H. The applicator tip is expected to remain in the same position relative to the tissue, while different sub-sets of electrodes in the applicator tip are made active or inactive, as shown.

As previously stated, a pattern of electrodes may be rotated by electrically switching/activating different sub-sets of the electrodes. For example, rotation of the electric field between different combinations of electrodes in an electrode array can be done by a controller sequentially selecting each combination of a sequence of selected combinations in a selected treatment protocol, by using one or more controllers or relays to electrically activate each combination, and then switch the activation to the next combination in the selected sequence until all combinations in the selected treatment protocol have been activated.

As discussed above, the methods described herein are especially suited for use with a robotic system, and/or other automated and/or computer-implemented applications. For example, the apparatuses (e.g., devices and systems) and methods described herein may be utilized in various ablation procedures (e.g. radiation-based), dermatological procedures (e.g., treating various dermatological conditions, such as skin cancers), etc.

Figure 26:
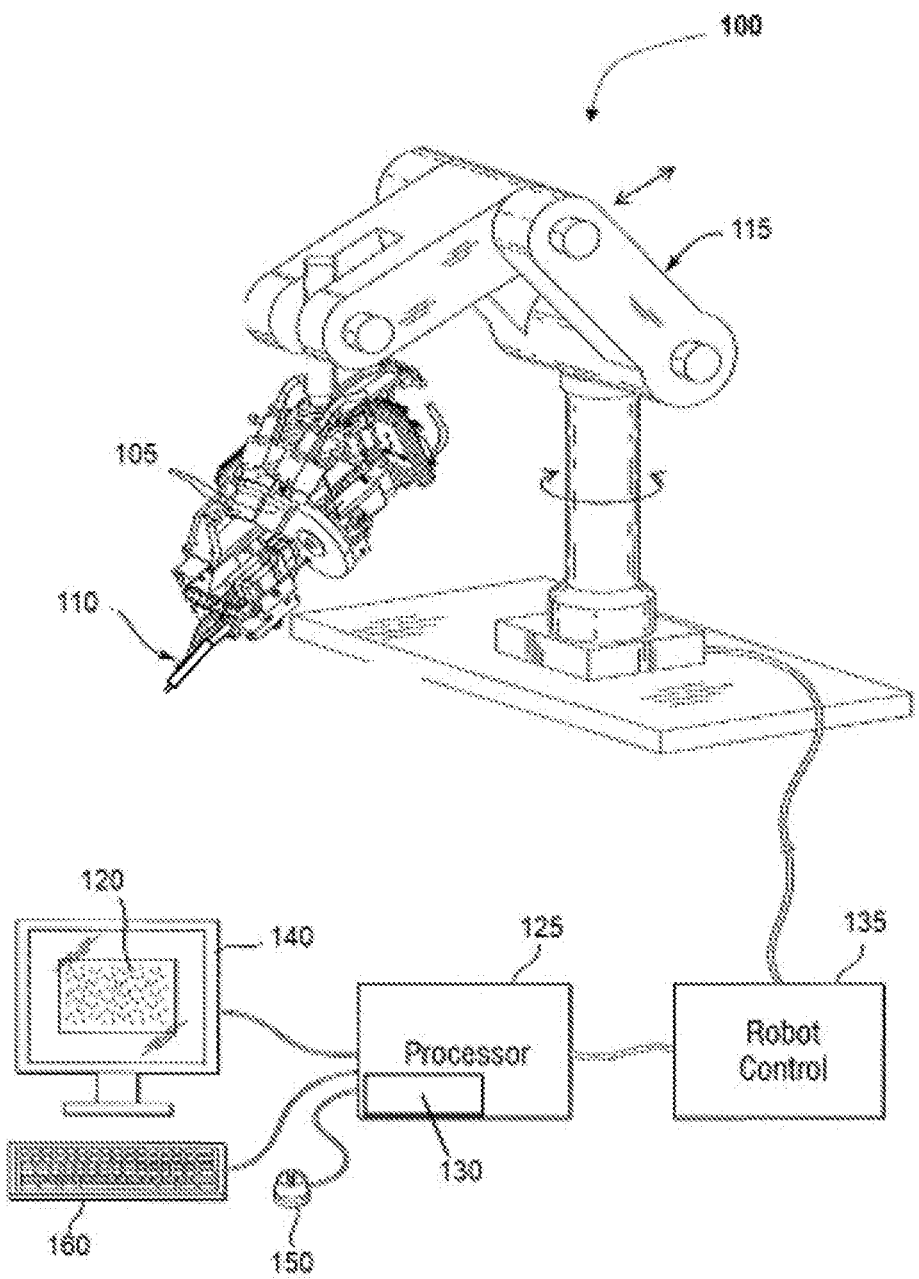
FIG. 26 illustrates an example of a robotic or semi-robotic system that may be used for rotating a pattern of electrodes partway through a treatment. The robotic system may accurately and precisely control rotation of the applicator tip during treatment, which may include inserting the electrode (e.g., needle electrode) pattern into the tissue, applying some portion (e.g., 20%, 30%, 40%, 45%, 50%, 55%, 60%, 70%, etc.) of the treatment, then withdrawal from the tissue, and re-insertion into the tissue to apply the remaining portion of the treatment.

FIG. 26 is a schematic perspective view of an example of a robotic system 100 that may be used to rotate the electrodes partway through a treatment. The system 100 may include a robotic arm 115 to which is coupled an applicator 110, such as an energy delivery device, having an applicator tip with a plurality of electrodes. Various motors and other movement devices may be incorporated to enable fine movements of an operating tip of the applicator 110 in multiple directions. The robotic system 100 may further include at least one (and preferably two for stereo vision, or more) image acquisition device 105 which may be mounted in a fixed position or coupled (directly or indirectly) to a robotic arm 115 or other controllable motion device. The operating tip of the applicator 110 may be positioned over a tissue (not shown).

The processor 125 of FIG. 26 may comprise, if applicable, an image processor 130 for processing images obtained from the image acquisition device 105. The image processor 130 may be a separate device or it may be incorporated as a part of the processor 125. The processor 125 may also instruct the various movement devices of the robotic arm 115, including the applicator 110, and act, for example, through a controller 135 as schematically shown in FIG. 26. The controller 135 may be operatively coupled to the robotic arm and configured to control the motion of the robotic arm, including the motion based on the images or data acquired by the image acquisition device. Alternatively, controller 135 may be incorporated as a part of the processor 125, so that all processing and controls of all movements of all the tools, the robotic arm and any other moveable parts of the assembly, including those based on the images or data acquired by the image acquisition device, are concentrated in one place. The system 100 may further comprise a monitor 140, mouse 150 and keyboard 160. In addition, the system 100 may comprise other tools, devices and components useful in treating a tissue, including with a pulsed electrical treatment. The system may further include an interface (not shown) adapted to receive an image data, various parts of the system allow an operator to monitor conditions and provide instructions, as needed. The processor 125 may interact with the imaging device 105 via the interface. The interface may include hardware ports, cables, leads, and other data transmission means, or it may comprise a computer program.

Some non-limiting examples of an image acquisition device 105 shown in FIG. 26 include one or more cameras, such as any commercially available cameras. The image acquisition or imaging device may be held, for example, by a robotic arm, or by any other mechanism or means. Various image acquisition devices or a combination of several devices could be used with any of the embodiments of the systems and methods described herein. The image acquisition device 105 may comprise a device that takes still images, it can also comprise a device capable of real time imaging (e.g., webcam capable of continuously streaming real time information), and/or it could also have a video recording capability (such as a camcorder, or smart phone or other mobile device). While stereo or multi-view imaging devices are very useful in the present disclosure, it is not necessary to employ such geometries or configurations, and the present disclosure is not so limited. The image acquisition device may be coupled to a processing system 125, shown incorporated in the image processor 130 in FIG. 26, to control the imaging operation and process image data.

Typically, the processor 125 operates as a data processing device, for example, it may be incorporated into a computer. The processor 125 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 125 may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor 130 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present disclosure is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the disclosure may be, at least partially, implemented on a card for a network device or a general-purpose computing device. The processor/image processor may also include memory, storage devices, and other components generally known in the art and, therefore, they do not need to be described in detail here. The image processor could be used in conjunction with various manual, partially automated and fully automated (including robotic) systems and devices.

The imaging display device 140 may comprise a high resolution computer monitor which may optionally be a touch screen. The imaging display may allow images, such as video or still images, to be readable and for follicular units, and parts thereof, to be visualized. Alternatively, the imaging display device 140 can be other touch sensitive devices, including tablet, pocket PC, and other plasma screens. The touch screen may be used to modify the parameters of the hair transplantation procedure, directly through the image display device.

Methods, and apparatuses of the present disclosure may be carried out by providing a modification interface, or user modification interface, including touch screen, clickable icons, selection buttons in a menu, dialog box, or a roll-down window of an interface that may be provided to feed into the computer. According to another embodiment, the imaging display device 140 may display the selection window and a stylus or keyboard for entering a selection, for example, directly on the display itself. According to one embodiment, commands may be input via the modification interface through a programmable stylus, keyboard, mouse, speech processing system, laser pointer, touch screen, tablet computer, personal digital assistant (PDA), a remote input device (such as a pendant), or other input mechanism. The remote input device may include clickable icons, selection buttons, dialog boxes, or roll-down windows which are the same as or similar to those found on the user modification interface, providing a convenient way for the user to control common user interface functions from their position at the patient's side. Alternatively, the remote input device may only accommodate, for example, a subset of such modification controls, making for a more compact pendant. In yet another embodiment, the remote input device may be configured to accommodate additional modification controls. Moreover, either the remote input device or any other input mechanism may have icons which allow the user to control the robotic arm, allowing the user to move the robotic arm away from the patient, or incorporate a STOP button, enabling the user to terminate operation of the robotic arm or the applicator in the event of an emergency. Alternatively, the modification interface may comprise a dedicated piece of hardware. In some embodiments the selections or adjustment made through the modification interface may be executed by code instructions that may be executed on the computer processor.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

The one or more processor for use in the present disclosure may comprise any suitable device programmed and configured to perform various methods described herein. In some embodiments modification may be accomplished through the modification interface. For example, the processor for use in the present disclosure may be a processor which may comprise a set of instructions for executing operations, the set of instructions including instructions for applying treatment via the applicator. The user may input how much of the treatment to perform before rotating the pattern, what energy to apply before and/or after rotating, the duration of the treatment, the location of the treatment, the tissue impedance change before each rotation, and any other appropriate parameter. A system for use according to the disclosures described herein may comprise in addition to a processor an image acquisition device. Thus, any of these apparatuses may include a user input device, the user input device configured to allow a user to interactively modify any of these parameters. In other embodiments, the processor is configured to automatically modify these parameters (e.g., input how much of the treatment to perform before rotating the pattern, what energy to apply, the duration of the treatment, the location of the treatment, etc.).

Certain embodiments relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. I may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform or control performing of any of the steps, including but not limited to: displaying, communicating with the user, analyzing, modifying parameters (including timing, frequency, intensity, etc.), determining, alerting, or the like. In some exemplary embodiments hardware may be used in combination with software instructions to implement the present disclosure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

The terms "comprises" and/or "comprising," when used in this specification (including the claims), specify the presence of stated features, steps, operations, elements, and/or components, but do not preclude the presence or addition of one or more other features, steps, operations, elements, components, and/or groups thereof. Unless the context requires otherwise, "comprise", and variations such as "comprises" and "comprising," means various components can be co-jointly employed in the methods and articles (e.g., compositions and apparatuses including device and methods). For example, the term "comprising" will be understood to imply the inclusion of any stated elements or steps but not the exclusion of any other elements or steps.

Any of the apparatuses and methods described herein may include all or a sub-set of the components and/or steps, and these components or steps may be either non-exclusive (e.g., may include additional components and/or steps) or in some variations may be exclusive, and therefore may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the apparatuses and methods as it is set forth in the claims.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

It will be understood that the following clauses form part of the disclosure of the invention defined herein. More particularly, the invention herein may be defined by the combination of the features of the clauses as detailed below and said clauses may be utilized to amend the combination of the features within the claims of this application.

1. A system comprising:
a pulse generator;
an applicator tip having a plurality of electrodes in a pattern of electrodes, the applicator tip configured to apply energy from the pulse generator to the plurality of electrodes;
a controller configured to control, at least partially, operation of the pulse generator to:
apply a first portion of a pulsed electrical treatment to a region of tissue through the plurality of electrodes with the pattern of electrodes contacting the region in a first orientation and apply a second portion of the pulsed electrical treatment to the region with the pattern in a second orientation that is rotated relative to the first orientation; and
a mechanism configured to cause rotation of the pattern between the first and the second configuration.

2. The system of clause 1, wherein the applicator tip comprises an array of electrodes in which the plurality of electrodes is a first subset of active electrodes forming the pattern, and wherein applying the second portion of the pulsed electrical treatment comprises forming the pattern from a second subset of active electrodes of the array of electrodes in which the pattern formed by the second subset is rotated relative to the first subset.

3. The system of clause 1 or clause 2, wherein the second orientation is rotated between 40 degrees and 100 degrees relative to the first orientation.

4. The system of any of clauses 1 to 3, wherein the second orientation is rotated about a midline through the plurality of electrodes.

5. The system of any preceding clause, wherein the mechanism comprises an actuator operable to be manually actuated causing rotation of the pattern; or the mechanism comprises a processor having a set of instructions operable to be executed causing rotation of the pattern.

6. The system of any of clauses 1 to 5, wherein the mechanism is operable to cause the applicator tip to rotate so that the pattern is rotated from the first to the second orientation.

7. The system of any of clauses 1 to 5, wherein the mechanism comprises a first mechanism operable to cause removal of the plurality of electrodes from the region, rotation of the applicator tip, and bringing the plurality of electrodes back in contact with the region before applying the second portion of the pulsed electrical treatment; or wherein the mechanism comprises a first and a second mechanism, the first mechanism is operable to cause rotation of the applicator tip, and the second mechanism is operable to cause removal of the plurality of electrodes from the region and bringing the plurality of electrodes back in contact with the region before applying the second portion of the pulsed electrical treatment.

8. The system of clause 7, wherein removal, rotation and bringing back in contact are performed by a robotic system.

9. The system of any preceding clause, wherein applying the first portion of the pulsed electrical treatment and applying the second portion of the pulsed electrical treatment each comprises applying electrical pulses to the region to de-nucleate cells within the region without provoking a substantial inflammatory response, so that after the treatment the tissue forms a necrotic crust over the region so that when the necrotic crust is removed new tissue is exposed.

10. The system of any preceding clause, wherein the region of tissue comprises one or more of: seborrheic keratosis, keloids, molluscum contagiosum, sebaceous hyperplasia, acrocordon, syringoma, psoriasis, papilloma, congenital capillary malformation (port-wine stain), human papilloma virus (HPV), melanoma, melasma, actinic keratoses, dermatosis papulosa nigra, angiofibroma, skin tumors, aged skin, wrinkled skin, or warts.

11. The system of any of clauses 2 to 10, wherein a path for energy from the first subset of active electrodes to the second subset of active electrodes is switched through electrical connections.

12. The system of any of clauses 2 to 10, wherein a path for energy from the first subset of active electrodes to the second subset of active electrodes is switched through mechanical connections.

13. The system of clause 12, wherein the plurality of electrodes is stationary positioned substantially along polygonal or curved perimeter sides of an end wall of the applicator tip and the mechanical connections are through at least two connectors configured to connect to parallel or opposite perimeter rows of electrodes.

14. The system of clause 12, wherein at least some electrodes of the first subset of active electrodes is movable.

15. The system of any preceding clause, wherein the pulse generator is configured to deliver pulses having a pulse duration of equal or less than 1 microsecond and a peak field strength of at least 1 kV/cm.

16. The system of any preceding clause, wherein the first portion of the treatment is between 30% and 70% of a duration of the pulsed electrical treatment.

17. A system comprising:
a movable arm;
an applicator operatively coupled to the movable arm, the applicator configured to apply pulsed electrical energy from a plurality of electrodes of the applicator; and
a processor comprising a set of instructions for executing operations, the set of instructions including instructions for:
moving the movable arm to place the applicator in contact with a region of tissue;
applying a first portion of the pulsed electrical treatment to the region through a pattern of electrodes contacting the region of the tissue in a first orientation; and
applying a second portion of the pulsed electrical treatment to the region through the pattern of electrodes contacting the region in a second orientation that is rotated relative to the first orientation.

18. The system of clause 17, the system comprising a navigation interface configured to receive imaging data.

19. The system of clause 17 or clause 18, wherein the set of instructions comprises instructions for removing the applicator from the region, rotating the applicator so that that the plurality of electrodes is moved to the second orientation, and reapplying the applicator tip to the region.

20. The system of any of clauses 17 to 19, wherein a degree or amount of rotation from the first orientation to the second orientation is user selected through a user interface or automatically directed by the processor through the set of instructions.

21. A system for use in a method of applying a pulsed electrical treatment comprising a plurality of electrical pulses, the system comprising an applicator tip having a plurality of electrodes,
wherein the pulsed electrical treatment is divided into at least a first portion and a second portion, the method comprising:
contacting a region with the applicator tip having the plurality of electrodes;
applying the first portion of the pulsed electrical treatment to the region in a pattern of electrodes from the plurality of electrodes, the pattern of electrodes contacting the region in a first orientation; and
applying the second portion of the pulsed electrical treatment to the region in the pattern of electrodes contacting the region in a second orientation that is rotated relative to the first orientation.

22. The system of clause 21, wherein the second portion of the pulsed electrical treatment is applied through the same electrodes of the plurality of electrodes that the first portion of the pulsed electrical treatment is applied through.

23. The system of clause 21, wherein the second portion of the pulsed electrical treatment is applied through different electrodes of the plurality of electrodes that the first portion of the pulsed electrical treatment is applied through.

24. The system of any of clauses 21 to 23, wherein applying the pulsed electrical treatment increases a marker of inflammation within the region by less than 15%, wherein the marker of inflammation is one or of more of: fibroblast density, leukocyte density, Interleukin-6, Interleukin-8, Interleukin-18, Tumor necrosis factor-alpha, and C-reactive protein.

25. The system of any of clauses 21 to 24, wherein a degree of rotation from the first orientation to the second orientation is user selected or automatically directed by a controller.

26. The system of any of clauses 21 to 25, wherein the method comprises selecting or allowing selection of one or more of the following: amount of energy to apply during the applying the first and/or the second portion of the pulsed electrical treatment, a percentage of one or both of the first portion and the second portion of the pulsed electrical treatment, a degree or amount of rotation of the pattern of electrodes, a duration of the pulsed electrical treatment, or a tissue impedance change before each rotation.

27. The system of any of clauses 21 to 26, wherein the method is at least partially automated, the method comprising automatically rotating the pattern of electrodes from the first orientation to the second orientation.

28. The system of any of clauses 21 to 27, wherein the applicator tip comprises an array of electrodes in which the plurality of electrodes is a first subset of active electrodes forming the pattern, and wherein applying the second portion of the pulsed electrical treatment comprises forming the pattern from a second subset of active electrodes of the array of electrodes in which the pattern formed by the second subset is rotated relative to the first subset.

29. A system comprising:
a pulse generator;
a set of electrodes; and
a controller configured to control, at least partially, operation of the pulse generator, the controller is operable to cause the pulse generator to generate and apply through the set of electrodes a pulsed electrical treatment to a region of tissue to de-nucleate cells within the region without provoking a substantial inflammatory response, so that the tissue forms a necrotic crust and forms new tissue below the necrotic crust so that when the necrotic crust is removed the new tissue is exposed.

30. The system of clause 29, wherein the system is a robotic system comprising a moveable arm.

31. The system of clause 29 or clause 30, wherein applying the pulsed electrical treatment comprises applying a non-thermal treatment that does not disrupt cell membranes within the tissue.

32. The system of any of clauses 29 to 31, wherein the tissue is a skin and applying the pulsed electrical field further comprises restoring the elastin integrity of the skin before the necrotic crust is removed.

33. The system of any of clauses 29 to 32, wherein the system is configured for treatment of one or more of: seborrheic keratosis, keloids, molluscum contagiosum, sebaceous hyperplasia, syringoma, congenital capillary malformation (port-wine stain), melasma, actinic keratoses, dermatosis papulosa nigra, angiofibroma, and warts.

34. The system of any of clauses 29 to 33, wherein the pulsed electrical treatment comprises applying between 2 and 120 of high-field strength pulses.

35. The system of any of clauses 29 to 33, wherein the pulse generator is configured to apply nanosecond electrical pulses having a pulse duration of between 0.1 ns and 1000 ns.

36. The system of clauses 1, 17 or 29 for use in therapy, optionally non-thermal therapy.

37. The system of clauses 1, 17 or 29 for use in treating tissue, optionally skin or tumorous tissue, and further optionally for use in treating tissue without disrupting cell membranes within the tissue.

38. The system of clauses 1, 17 or 29 for use in selectively removing tissue from a subject.

39. The system of clauses 1, 17 or 29 for use in selectively destroying the nuclei of treated cells, optionally epithelial cells, without provoking a significant inflammatory response, and optionally without affecting adjacent non-cellular tissue.

40. The system of clauses 1, 17 or 29 for use in formation of new epidermal tissue with reduced or no significant scarring and a normal appearance after restoration of the epidermal surface after a normal healing period.

41. The system of clause 40, wherein the normal appearance comprises normal distribution of melanocytes, normal elastin distribution and normal density of the epidermal tissue.

42. A method of applying a pulsed electrical treatment comprising a plurality of electrical pulses, wherein the pulsed electrical treatment is divided into at least a first portion and a second portion, the method comprising:
contacting a region with an applicator tip having a plurality of electrodes;
applying the first portion of the pulsed electrical treatment to the region in a pattern of electrodes from the plurality of electrodes, the pattern of electrodes contacting the region in a first orientation; and
applying the second portion of the pulsed electrical treatment to the region in the pattern of electrodes contacting the region in a second orientation that is rotated relative to the first orientation.

43. The method of clause 42, the method comprising removing the plurality of electrodes from a contact with the region prior to contracting the region in the second orientation.

44. A system comprising a set of electrodes for use in a method of treating skin, the method comprising:
positioning the set of electrodes in communication with a region of skin;
non-thermally destroying the viability of epidermal cells within the region of the skin by applying a plurality of high-field strength, ultra-short electrical pulses to the region of the skin from the set of electrodes, without provoking a substantial inflammatory response within the region, so that the skin forms a necrotic crust over the region of the skin and forms new epidermis below the necrotic crust so that when the necrotic crust is removed the new epidermis is exposed;
wherein the high-field strength, ultra-short electrical pulses comprise a plurality of pulses
each having a duration of between 0.1 ns and 1000 ns and a peak field strength of at least 1 kV/cm 45. The system of clause 44, wherein non-thermally destroying the viability of epidermal cells within the region of the skin comprises disrupting the viability of greater than 90% of the epidermal cells within the region.

46. The system of clause 44, wherein non-thermally destroying the viability of epidermal cells within the region comprises de-nucleating the epidermal cells within the region.

47. The system of any of clauses 44 to 46, wherein applying the plurality of high-field strength, ultra-short electrical pulses increases a marker of inflammation within the region of the skin by less than 15%, wherein the marker of inflammation is one or of more of: fibroblast density, leukocyte density, Interleukin-6, Interleukin-8, Interleukin-18, Tumor necrosis factor-alpha, and C-reactive protein.

48. The system of any of clauses 44 to 47, wherein applying the plurality of high-field strength, ultra-short electrical pulses comprises applying between 2 and 120 pulses at between 0.05 Hz and 20 Hz.

49. A method of treating skin, the method comprising:
positioning a set of electrodes in communication with a region of a skin;
non-thermally destroying the viability of epidermal cells within the region of the skin by applying a plurality of high-field strength, ultra-short electrical pulses to the region of the skin from the set of electrodes, without provoking a substantial inflammatory response within the region, so that the skin forms a necrotic crust over the region of the skin and forms new epidermis below the necrotic crust so that when the necrotic crust is removed the new epidermis is exposed;
wherein the high-field strength, ultra-short electrical pulses comprise a plurality of pulses each having a duration of between 0.1 ns and 1000 ns and a peak field strength of at least 1 kV/cm.

The invention claimed is:

1. A system comprising:
a pulse generator;
an applicator tip having a plurality of electrodes in a pattern of electrodes, wherein the applicator tip is configured to be removably coupled to a handpiece and to apply energy from the pulse generator to the plurality of electrodes and wherein the pattern of electrodes is configured to rotate about a midline through a center of the pattern of electrodes and relative to the handpiece to which the applicator tip is coupled; and
a controller configured to control, at least partially, operation of the pulse generator to:
apply a first portion of a pulsed electrical treatment to a region of tissue through the plurality of electrodes with the pattern of electrodes contacting the region in a first orientation, and
apply a second portion of the pulsed electrical treatment to the region with the pattern in a second orientation that is rotated relative to the first orientation.

2. The system of claim 1, wherein the applicator tip comprises an array of electrodes in which the plurality of electrodes is a first subset of active electrodes forming the pattern, and wherein applying the second portion of the pulsed electrical treatment comprises forming the pattern from a second subset of active electrodes of the array of electrodes in which the pattern formed by the second subset is rotated relative to the first subset.

3. The system of claim 2, wherein a path for energy from the first subset of active electrodes to the second subset of active electrodes is switched through electrical connections.

4. The system of claim 2, wherein a path for energy from the first subset of active electrodes to the second subset of active electrodes is switched through mechanical connections.

5. The system of claim 4, wherein the plurality of electrodes is stationary positioned along polygonal or curved perimeter sides of an end wall of the applicator tip and the mechanical connections are through at least two connectors configured to connect to parallel or opposite perimeter rows of electrodes.

6. The system of claim 4, wherein at least some electrodes of the first subset of active electrodes is movable.

7. The system of claim 1, wherein the second orientation is rotated between 40 degrees and 100 degrees relative to the first orientation.

8. The system of claim 1, further comprising a mechanism configured to cause rotation of the pattern between the first and the second configuration.

9. The system of claim 8, wherein the mechanism is operable to cause the applicator tip to rotate so that the pattern is rotated from the first to the second orientation.

10. The system of claim 8, wherein the mechanism comprises one or more mechanisms operable to cause removal of the plurality of electrodes from the region, rotation of the applicator tip, and bringing the plurality of electrodes back in contact with the region before applying the second portion of the pulsed electrical treatment.

11. The system of claim 10, wherein removal, rotation and bringing back in contact are performed by a robotic system.

12. The method of claim 8, wherein the mechanism comprises one or more switches or relays configured to switch circuits connecting alternative sets of electrodes of plurality of electrodes.

13. The system of claim 8, wherein the mechanism comprises an actuator operable to be manually actuated causing rotation of the pattern.

14. The system of claim 1, wherein applying the first portion of the pulsed electrical treatment and applying the second portion of the pulsed electrical treatment each comprises applying electrical pulses to the region to de-nucleate cells within the region without provoking an inflammatory response, so that after the treatment the tissue forms a necrotic crust over the region so that when the necrotic crust is removed new tissue is exposed.

15. The system of claim 1, wherein the pulse generator is configured to deliver pulses having a pulse duration of equal or less than 1 microsecond and a peak field strength of at least 1 kV/cm.

16. The system of claim 1, wherein the first portion of the pulsed electrical treatment is between 30% and 70% of a duration of an entire pulsed electrical treatment.

17. The system of claim 1, the system comprising a navigation interface configured to receive imaging data.

18. The system of claim 1, wherein a degree or amount of rotation from the first orientation to the second orientation is user selected through a user interface or automatically directed by a processor through a set of instructions.

19. The system of claim 1, wherein the second portion of the pulsed electrical treatment is applied through the same electrodes of the plurality of electrodes that the first portion of the pulsed electrical treatment is applied through.

20. The system of claim 1, wherein applying the pulsed electrical treatment increases a marker of inflammation within the region by less than 15%, wherein the marker of inflammation is one or of more of: fibroblast density, leukocyte density, Interleukin-6, Interleukin-8, Interleukin-18, Tumor necrosis factor-alpha, and C-reactive protein.

21. The system of claim 1, wherein the system is configured to select or allow selection of one or more of the following: amount of energy to apply during the applying the first and/or the second portion of the pulsed electrical treatment, a percentage of one or both of the first portion and the second portion of the pulsed electrical treatment, a degree or amount of rotation of the pattern of electrodes, a duration of the pulsed electrical treatment, or a tissue impedance change before each rotation.

22. The system of claim 1, wherein the pattern of electrodes is configured to rotate by rotating at least a portion of the applicator tip relative to the handpiece.

23. The system of claim 1, wherein the pattern of electrodes is configured to rotate by switching a switch plate between active columns and active rows of the plurality of electrodes.

24. The system of claim 1, wherein the plurality of electrodes includes a subset of stationary needle electrodes and a subset of movable needle electrodes disposed between the stationary needle electrodes and configured to retract and extend relative an end of the applicator tip.

25. The system of claim 1, the system configured such that rotation of the pattern of electrodes is achieved without movement of electrodes of the plurality of electrodes.

26. A system comprising:
a pulse generator;
an applicator tip having a plurality of electrodes in a pattern of electrodes, the applicator tip is configured to apply energy from the pulse generator to the plurality of electrodes, wherein the plurality of electrodes includes a subset of stationary needle electrodes and a subset of movable needle electrodes disposed between the stationary needle electrodes and configured to retract and extend relative to an end of the applicator tip; and
a controller configured to control, at least partially, operation of the pulse generator to:
apply a first portion of a pulsed electrical treatment to a region of tissue through the plurality of electrodes with the pattern of electrodes contacting the region in a first orientation, and
apply a second portion of the pulsed electrical treatment to the region with the pattern in a second orientation that is rotated relative to the first orientation,
wherein the pattern of electrodes is configured to rotate relative to the handpiece to which the applicator tip is coupled by retracting or extending the subset of movable needle electrodes.

27. A system comprising:
a pulse generator;
an applicator tip having a plurality of electrodes in a pattern of electrodes, wherein the applicator tip is configured to be removably coupled to a handpiece and to apply energy from the pulse generator to the plurality of electrodes and wherein the pattern of electrodes is configured to rotate relative to the handpiece to which the applicator tip is coupled; and
a controller configured to control, at least partially, operation of the pulse generator to:
apply a first portion of a pulsed electrical treatment to a region of tissue through the plurality of electrodes with the pattern of electrodes contacting the region in a first orientation, and
apply a second portion of the pulsed electrical treatment to the region with the pattern in a second orientation that is rotated relative to the first orientation,
wherein the applicator tip is configured to remain in the same position relative to the tissue while a first sub-set of electrodes delivers the first portion of a pulsed electrical treatment and while a second sub-set of electrodes delivers the second portion of the pulsed electrical treatment.

28. The system of claim 27, wherein the applicator tip comprises an array of electrodes in which the plurality of electrodes is the first subset of active electrodes forming the pattern, and wherein applying the second portion of the pulsed electrical treatment comprises forming the pattern from the second subset of active electrodes of the array of electrodes in which the pattern formed by the second subset is rotated relative to the first subset.

29. The system of claim 27, wherein the second orientation is rotated between 40 degrees and 100 degrees relative to the first orientation.

30. The system of claim 27, further comprising a mechanism configured to cause rotation of the pattern between the first and the second configuration.

31. The system of claim 30, wherein the mechanism comprises one or more mechanisms operable to cause removal of the plurality of electrodes from the region, rotation of the applicator tip, and bringing the plurality of electrodes back in contact with the region before applying the second portion of the pulsed electrical treatment.

32. The system of claim 31, wherein removal, rotation and bringing back in contact are performed by a robotic system.

33. The system of claim 27, the system comprising a navigation interface configured to receive imaging data.

34. A system comprising:
  a pulse generator;
  an applicator tip having a plurality of electrodes in a pattern of electrodes, wherein the applicator tip is configured to be removably coupled to a handpiece and to apply energy from the pulse generator to the plurality of electrodes and wherein the pattern of electrodes is configured to rotate relative to the handpiece to which the applicator tip is coupled; and
  a controller configured to control, at least partially, operation of the pulse generator to:
    apply a first portion of a pulsed electrical treatment to a region of tissue through the plurality of electrodes with the pattern of electrodes contacting the region in a first orientation, and
    apply a second portion of the pulsed electrical treatment to the region with the pattern in a second orientation that is rotated relative to the first orientation,
    wherein the second portion of the pulsed electrical treatment is applied through different electrodes of the plurality of electrodes than the first portion of the pulsed electrical treatment is applied through.

* * * * *